United States Patent
Nakano et al.

(10) Patent No.: US 9,978,952 B2
(45) Date of Patent: May 22, 2018

(54) FUSED HETEROCYCLIC AROMATIC DERIVATIVE, ORGANIC ELECTROLUMINESCENCE ELEMENT MATERIAL, AND ORGANIC ELECTROLUMINESCENCE ELEMENT USING SAME

(75) Inventors: Yuki Nakano, Sodegaura Chiba (JP); Kei Yoshida, Sodegaura Chiba (JP); Hideaki Nagashima, Sodegaura Chiba (JP); Ryohei Hashimoto, Sodegaura Chiba (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 380 days.

(21) Appl. No.: 14/234,533

(22) PCT Filed: Sep. 11, 2012

(86) PCT No.: PCT/JP2012/005734
§ 371 (c)(1),
(2), (4) Date: Jan. 23, 2014

(87) PCT Pub. No.: WO2013/038650
PCT Pub. Date: Mar. 21, 2013

(65) Prior Publication Data
US 2014/0175419 A1    Jun. 26, 2014

(30) Foreign Application Priority Data
Sep. 13, 2011    (JP) .................................. 2011-199735

(51) Int. Cl.
*H01L 51/50*    (2006.01)
*H01L 51/00*    (2006.01)
(Continued)

(52) U.S. Cl.
CPC ........ *H01L 51/0067* (2013.01); *C07D 307/91* (2013.01); *C07D 333/76* (2013.01);
(Continued)

(58) Field of Classification Search
None
See application file for complete search history.

(56) References Cited

U.S. PATENT DOCUMENTS

2007/0267970 A1* 11/2007 Yamamoto ........... C07D 235/08
                                                    313/506
2010/0084966 A1*  4/2010 Otsu ................... C07D 405/14
                                                    313/504

FOREIGN PATENT DOCUMENTS

JP    2007-214175 A    8/2007
JP    2010-021336 A    1/2010
(Continued)

OTHER PUBLICATIONS

Thiemann, T. et al. "Studies Towards Dibenzothiophene-S-Oxide Arrays and Their Photochemical Reactivity". The Reports of Institute of Advanced Material Study, Kyushu University, vol. 15 No. 1, 2001, pp. 63-71.
(Continued)

*Primary Examiner* — Gregory D Clark
(74) *Attorney, Agent, or Firm* — Foley & Lardner LLP

(57) ABSTRACT

A compound represented by the following formula (1). In the formula, $A_1$ is O, S, $Si(Ar_1)(Ar_2)$, $P(=O)(Ar_3)(Ar_4)$, a substituted or unsubstituted arylene group including 6 to 30 ring carbon atoms, or a substituted or unsubstituted heteroarylene group including 5 to 30 ring atoms.
(Continued)

(1)

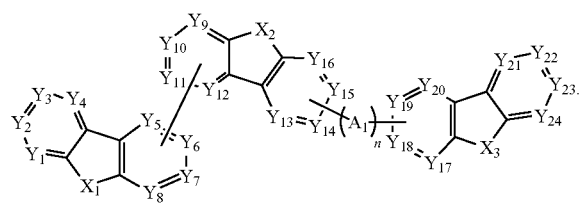

41 Claims, 1 Drawing Sheet

(51) Int. Cl.
C07D 333/76 (2006.01)
C07D 519/00 (2006.01)
C07D 307/91 (2006.01)
C09K 11/06 (2006.01)
H05B 33/10 (2006.01)
C09B 57/00 (2006.01)
C09B 69/00 (2006.01)

(52) U.S. Cl.
CPC ............ C07D 519/00 (2013.01); C09B 57/00 (2013.01); C09B 69/008 (2013.01); C09K 11/06 (2013.01); H01L 51/0071 (2013.01); H01L 51/0073 (2013.01); H01L 51/0074 (2013.01); H05B 33/10 (2013.01); C09K 2211/1007 (2013.01); C09K 2211/1011 (2013.01); C09K 2211/1029 (2013.01); C09K 2211/1044 (2013.01); C09K 2211/1059 (2013.01); C09K 2211/1088 (2013.01); C09K 2211/1092 (2013.01); H01L 51/0085 (2013.01); H01L 51/5016 (2013.01)

(56) References Cited

FOREIGN PATENT DOCUMENTS

| JP | 2011-084531 A | 4/2011 |
|----|---------------|--------|
| WO | WO 2007/077810 A1 | 7/2007 |
| WO | WO 2008/072596 A1 | 6/2008 |
| WO | WO 2009/060742 A1 | 5/2009 |
| WO | WO 2009/060780 A1 | 5/2009 |
| WO | WO 2010/004877 A1 | 1/2010 |

OTHER PUBLICATIONS

International Search Report dated Nov. 13, 2012 in International Appl. PCT/JP2012/005734 (4 pgs.).

* cited by examiner

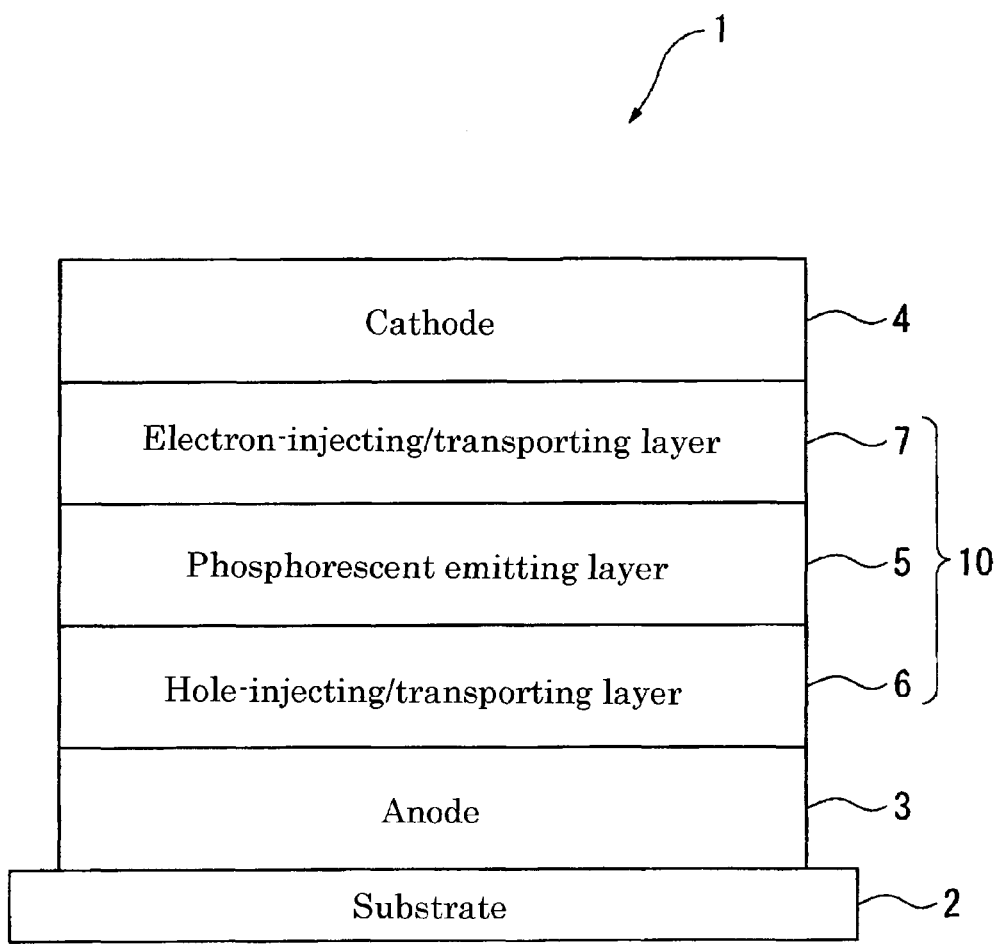

FUSED HETEROCYCLIC AROMATIC DERIVATIVE, ORGANIC ELECTROLUMINESCENCE ELEMENT MATERIAL, AND ORGANIC ELECTROLUMINESCENCE ELEMENT USING SAME

CROSS REFERENCE TO RELATED APPLICATIONS

This application is a national stage entry of PCT/JP2012/005734 filed Sep. 11, 2012, which claims priority from Japanese Patent Application No. 2011-199735, filed Sep. 13, 2011, the disclosures of which are hereby incorporated by reference in their entirety.

TECHNICAL FIELD

The invention relates to a fused heterocyclic aromatic derivative, a material for an organic electroluminescence device and an organic electroluminescence device using the same.

BACKGROUND ART

An organic electroluminescence (EL) device includes a fluorescent organic EL device or a phosphorescent organic EL device, and a device design optimum for the emission mechanism of each type of organic EL device has been studied. It is known that a highly efficient phosphorescent organic EL device cannot be obtained by merely applying fluorescent device technology due to the emission characteristics. The reasons therefor are generally considered to be as follows.

Specifically, since phosphorescence emission utilizes triplet excitons, a compound used for forming an emitting layer must have a large energy gap. This is because the energy gap (hereinafter often referred to as "singlet energy") of a compound is normally larger than the triplet energy (in the invention, the difference in energy between the lowest excited triplet state and the ground state) of the compound.

In order to confine the triplet energy of a phosphorescent dopant material efficiently in an emitting layer, it is required to use, in an emitting layer, a host material having a triplet energy larger than that of the phosphorescent dopant material. Further, an electron-transporting layer and a hole-transporting layer are required to be provided adjacent to the emitting layer, and a compound having a triplet energy larger than that of a phosphorescent dopant material is required to be used in an electron-transporting layer and a hole-transporting layer.

As mentioned above, if based on the conventional design concept of an organic EL device, it leads to the use of a compound having a larger energy gap as compared with a compound used in a fluorescent organic EL device in a phosphorescent organic EL device. As a result, the driving voltage of the entire organic EL device is increased.

Further, a hydrocarbon-based compound having a high resistance to oxidation or reduction, which has been useful in a fluorescent device, the π electron cloud spreads largely, and hence it has a small energy gap. Therefore, in a phosphorescent organic EL device, such a hydrocarbon-based compound is hardly selected. As a result, an organic compound including a hetero atom such as oxygen and nitrogen is selected, and hence a phosphorescent organic EL device has a problem that it has a short lifetime as compared with a fluorescent organic EL device.

In addition, a significantly long exciton relaxation speed of a triplet exciton of a phosphorescent dopant as compared with that of a singlet exciton greatly effects the device performance. That is, emission from the singlet exciton has a high relaxation speed that leads to emission, and hence, diffusion of excitons to peripheral layers (such as a hole-transporting layer and an electron-transporting layer) hardly occurs, whereby efficient emission is expected. On the other hand, in the case of emission from the triplet exciton, since it is spin-forbidden and has a slow relaxation speed, diffusion of excitons to peripheral layers tends to occur easily, and as a result, thermal energy deactivation occurs from other compounds than a specific phosphorescent emitting compound. That is, in a phosphorescent organic EL device, control of a recombination region of electrons and holes is more important than that of a fluorescent organic EL device.

For the reasons mentioned above, in order to improve the performance of a phosphorescent organic EL device, material selection and device design that are different from a fluorescent organic EL device have come to be required.

In particular, in the case of a phosphorescent organic EL device that emits blue color light, as compared with a phosphorescent organic EL device that emits green to red color light, it is preferable to use a compound having a high triplet energy in an emitting layer or peripheral layers thereof. In order to obtain a compound that not only has a high triplet energy but also has properties required for an organic EL device, it is required to conduct molecular design based on a new concept taking the electron state of π electrons into consideration, not to simply combine molecular parts having a high triplet energy such as a heterocyclic compound.

Patent Document 1 discloses a compound having at least two rings of dibenzothiophene and having an aromatic ring or a heterocyclic aromatic ring as a linker part of the two dibenzothiophenes. Further, this document shows that a device using a carbazole-containing compound as a host compound in this linker part has a long luminous life.

Patent Document 2 discloses a compound having four or more aromatic rings or heterocyclic aromatic rings, in which one of these rings is dibenzofurane or dibenzothiophene. This document shows that a device using a compound having carbazole as an aromatic heterocyclic ring as a host compound or an electron-transporting material is excellent in luminous efficiency and luminous life.

Patent Document 1: WO2010/004877
Patent Document 2: JP-A-2011-084531

SUMMARY OF THE INVENTION

The invention is aimed at providing an organic EL device which can be driven at a low voltage and has a long life, and a material for an organic EL device that realizes such an organic EL device.

The organic compound of the invention has three or more specific fused heterocyclic aromatic rings, and hence, the π electron cloud spreads largely. Accordingly, the carrier transporting properties of the device can be improved, and the device can be driven at a low voltage.

In addition, since no carbazole is contained in the specific fused heterocyclic aromatic ring, the entire compound has a large ionization potential. In this way, by using a compound having a large ionization potential as an electron-transporting (hole-blocking) layer, it is expected that holes can be retained in an emitting layer, thereby to prevent the luminous efficiency from lowering.

According to the invention, the following compound, the material for an organic EL device and an organic EL device are provided.

1. A compound represented by the following formula (1):

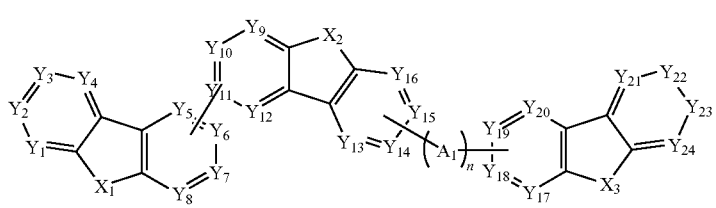

wherein in the formula (1), $X_1$ to $X_3$ are independently O or S;

$Y_1$ to $Y_4$ and $Y_{21}$ to $Y_{24}$ are independently $C(Ra_1)$ or N; of $Y_5$ to $Y_{12}$, one of $Y_5$ to $Y_8$ and one of $Y_9$ to $Y_{12}$ are carbon atoms which are bonded to each other, and the remaining $Y_5$ to $Y_{12}$ are independently $C(Ra_1)$ or N;

one of $Y_{13}$ to $Y_{16}$ which bonds to $A_1$ is a carbon atom, and the remaining $Y_{13}$ to $Y_{16}$ are independently $C(Ra_1)$ or N;

one of $Y_{17}$ to $Y_{20}$ which bonds to $A_1$ is a carbon atom, and the remaining $Y_{17}$ to $Y_{20}$ are independently $C(Ra_1)$ or N;

$A_1$ is O, S, $Si(Ar_1)(Ar_2)$, $P(=O)(Ar_3)(Ar_4)$, a substituted or unsubstituted arylene group including 6 to 30 carbon atoms that form a ring (hereinafter referred to as "ring carbon atoms"), or a substituted or unsubstituted heteroarylene group including 5 to 30 atoms that form a ring (hereinafter referred to as "ring atoms");

n is an integer of 1 to 4;

$Ar_1$ to $Ar_4$ are independently a substituted or unsubstituted aryl group including 6 to 30 ring carbon atoms, or a substituted or unsubstituted heteroaryl group including 5 to 30 ring atoms;

$Ra_1$ is a hydrogen atom, a substituted or unsubstituted aryl group including 6 to 30 ring carbon atoms, a substituted or unsubstituted heteroaryl group including 5 to 30 ring atoms, a substituted or unsubstituted alkyl group including 1 to 30 carbon atoms, a substituted or unsubstituted fluoroalkyl group including 1 to 30 carbon atoms, a substituted or unsubstituted cycloalkyl group including 3 to 30 carbon atoms, a silyl group which may be substituted by a substituted or unsubstituted alkyl group including 1 to 30 carbon atoms and/or an aryl group including 6 to 30 ring carbon atoms, a cyano group, a substituted or unsubstituted alkoxy group including 1 to 30 carbon atoms, a substituted or unsubstituted aryloxy group including 6 to 30 ring carbon atoms, a substituted or unsubstituted aralkyl group including 7 to 30 carbon atoms, a hydroxyl group, a nitro group, an amino group which may be substituted by a substituted or unsubstituted alkyl group including 1 to 30 carbon atoms and/or an unsubstituted aryl group including 6 to 30 ring carbon atoms, a carboxy group or $P(=O)(R_b)(R_c)$; and Rb and Rc are independently a hydrogen atom, a substituted or unsubstituted aryl group including 6 to 30 ring carbon atoms, a substituted or unsubstituted heteroaryl group including 5 to 30 ring atoms, a substituted or unsubstituted alkyl group including 1 to 30 carbon atoms, or a substituted or unsubstituted fluoroalkyl group including 1 to 30 carbon atoms.

2. The compound according to 1, which is represented by the following formula (2):

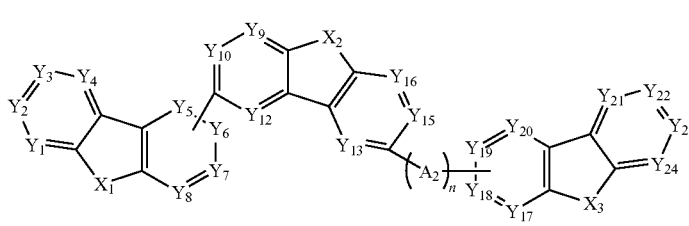

wherein in the formula (2), $X_1$ to $X_3$ are the same as $X_1$ to $X_3$ in the formula (1), respectively;

$Y_1$ to $Y_4$, $Y_9$, $Y_{10}$, $Y_{12}$, $Y_{13}$, $Y_{15}$, $Y_{16}$ and $Y_{21}$ to $Y_{24}$ are independently $C(Ra_2)$ or N;

one of $Y_5$ to $Y_8$ is a carbon atom being in a single bonded state, and the remaining $Y_5$ to $Y_8$ are independently $C(Ra_2)$ or N;

one of $Y_{17}$ to $Y_{20}$ which bonds to $A_2$ is a carbon atom, and the remaining $Y_{17}$ to $Y_{20}$ are independently $C(Ra_2)$ or N;

$A_2$ is O, S, $Si(Ar_1)(Ar_2)$, $P(=O)(Ar_3)(Ar_4)$, a substituted or unsubstituted arylene group including 6 to 30 ring carbon atoms, or a substituted or unsubstituted heteroarylene group including 5 to 30 ring atoms excluding a carbazolylene group;

n, and $Ar_1$ to $Ar_4$ are the same as n, and $Ar_1$ to $Ar_4$ in the formula (1), respectively;

$Ra_2$ is a hydrogen atom, a substituted or unsubstituted aryl group including 6 to 30 ring carbon atoms, a substituted or unsubstituted heteroaryl group including 5 to 30 ring atoms excluding a carbazole group, a substituted or unsubstituted alkyl group including 1 to 30 carbon atoms, a substituted or unsubstituted fluoroalkyl group including 1 to 30 carbon atoms, a substituted or unsubstituted cycloalkyl group including 3 to 30 carbon atoms, a silyl group which may be substituted by a substituted or unsubstituted alkyl group including 1 to 30 carbon atoms and/or an unsubstituted aryl group including 6 to 30 ring carbon atoms, a cyano group, a substituted or unsubstituted alkoxy group including 1 to 30 carbon atoms, a substituted or unsubstituted aryloxy group including 6 to 30 ring carbon atoms, a substituted or unsubstituted aralkyl group including 7 to 30 carbon atoms, a hydroxy group, a nitro group, an amino group which may be substituted by a substituted or unsubstituted alkyl group including 1 to 30 carbon atoms and/or an unsubstituted aryl group including 6 to 30 ring carbon atoms, a carboxy group or $P(=O)(R_b)(R_c)$; and Rb and Rc are the same as Rb and Rc in the formula (1), respectively.

3. The compound according to 2, which is represented by the following formula (3):

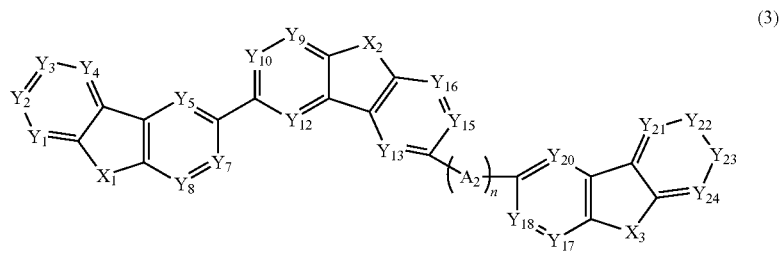

(3)

wherein in the formula (3), $Y_1$ to $Y_5$, $Y_7$ to $Y_{10}$, $Y_{12}$, $Y_{13}$, $Y_{15}$, $Y_{16}$ to $Y_{18}$ and $Y_{20}$ to $Y_{24}$ are independently $C(Ra_2)$ or N; and $X_1$ to $X_3$, $A_2$, n, $Ra_2$ are the same as $X_1$ to $X_3$, $A_2$, n, $Ra_2$ in the formula (2), respectively.

4. The compound according to 3, which is represented by the following formula (4):

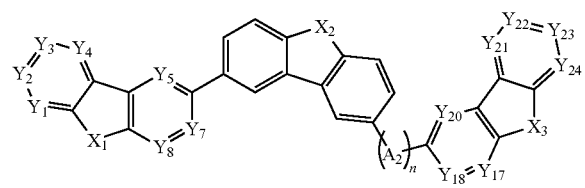

(4)

wherein in the formula (4), $X_1$ to $X_3$, $Y_1$ to $Y_5$, $Y_7$, $Y_8$, $Y_{17}$, $Y_{18}$, $Y_{20}$ to $Y_{24}$, $A_2$ and n are the same as $X_1$ to $X_3$, $Y_1$ to $Y_5$, $Y_7$, $Y_8$, $Y_{17}$, $Y_{18}$, $Y_{20}$ to $Y_{24}$, $A_2$ and n in the formula (3), respectively.

5. The compound according to any of 1 to 4, wherein the $A_1$ or $A_2$ are a substituted or unsubstituted arylene group including 6 to 30 ring carbon atoms.

6. The compound according to any of 1 to 4, wherein the $A_1$ or $A_2$ is a substituted or unsubstituted heteroarylene group including 5 to 20 ring atoms excluding a carbazolylene group.

7. The compound according to 4, which is represented by the following formula (5):

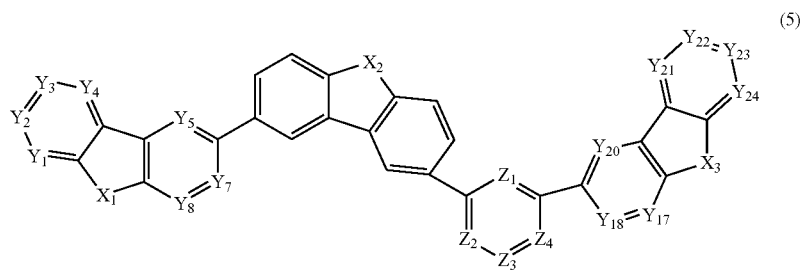

(5)

wherein in the formula (5), $Z_1$ to $Z_4$ are independently $C(Ra_2)$ or N;

$X_1$ to $X_3$, $Y_1$ to $Y_5$, $Y_7$, $Y_8$, $Y_{17}$, $Y_{18}$, and $Y_{20}$ to $Y_{24}$ are the same as $X_1$ to $X_3$, $Y_1$ to $Y_5$, $Y_7$, $Y_8$, $Y_{17}$, $Y_{18}$, and $Y_{20}$ to $Y_{24}$ in the formula (4), respectively; and $Ra_2$ is the same as $Ra_2$ in the formula (2).

8. A material for an organic electroluminescence device comprising the compound according to any of 1 to 7.

9. An organic electroluminescence device comprising one or more organic thin film layers including an emitting layer between a cathode and an anode, wherein at least one of the organic thin film layers comprises the material for an organic electroluminescence device according to 8.

10. The organic electroluminescence device according to 9, wherein the emitting layer comprises the material for an organic electroluminescence device.

11. The organic electroluminescence device according to 10, wherein the emitting layer comprises the material for an organic electroluminescence device as a host material for the emitting layer.

12. The organic electroluminescence device according to any of 9 to 11, wherein an electro-transporting region is provided between the emitting layer and the cathode, and the electro-transporting region comprises the material for an organic electroluminescence device.

13. The organic electroluminescence device according to any of 9 to 12, wherein the emitting layer comprises a phosphorescent material.

14. The organic electroluminescence device according to 13, wherein the phosphorescent material is a compound containing a metal selected from iridium (Ir), osmium (Os) and platinum (Pt).

15. The organic electroluminescence device according to 14, wherein the compound containing a metal is an ortho-metalized complex.

16. The organic electroluminescence device according to 9 to 15, wherein an electron-injecting layer is provided between the emitting layer and the cathode, and the electro-injecting layer comprises a nitrogen-containing heterocyclic derivative.

The compound of the invention has a structure in which two or more fused heterocyclic aromatic rings are bonded, and a fused heterocyclic aromatic ring is further bonded through an aromatic ring or a single atom. Due to the presence of three or more fused heterocyclic aromatic rings, carrier transporting properties are improved and a device can be driven at a low voltage. Further, due to such a configuration, advantageous effects are attained that crystallinity can be lowered while allowing the skeleton of the molecule to be strong, whereby a device suffering only a small amount of pixel defects and has a long life can be provided.

BRIEF DESCRIPTION OF THE DRAWINGS

FIG. 1 is a view showing a schematic configuration of one example of an organic EL device according to the embodiment of the invention.

MODE FOR CARRYING OUT THE INVENTION (Compound and Organic EL Device Material of the Invention)

The compound of the invention is a compound represented by the following formula (1):

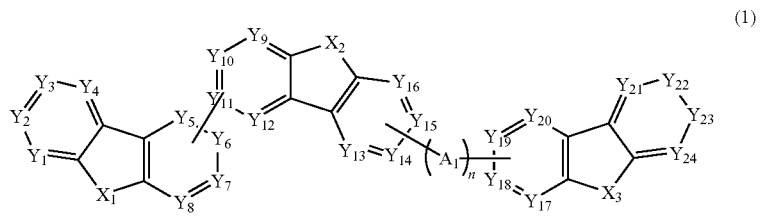

(1)

wherein in the formula (1), $Y_1$ to $Y_4$ and $Y_{21}$ to $Y_{24}$ are independently $C(Ra_1)$ or N;

of $Y_5$ to $Y_{12}$, one of $Y_5$ to $Y_8$ and one of $Y_9$ to $Y_{12}$ are carbon atoms which are bonded to each other, and the remaining $Y_5$ to $Y_{12}$ are independently $C(Ra_1)$ or N;

one of $Y_{13}$ to $Y_{16}$ which bonds to $A_1$ is a carbon atom, and the remaining $Y_{13}$ to $Y_{16}$ are independently $C(Ra_1)$ or N;

one of $Y_{17}$ to $Y_{20}$ which bonds to $A_1$ is a carbon atom, and the remaining $Y_{17}$ to $Y_{20}$ are independently $C(Ra_1)$ or N;

$A_1$ is O, S, $Si(Ar_1)(Ar_2)$, $P(=O)(Ar_3)(Ar_4)$, a substituted or unsubstituted arylene group including 6 to 30 carbon atoms that form a ring (hereinafter referred to as "ring carbon atoms"), or a substituted or unsubstituted heteroarylene group including 5 to 30 atoms that form a ring (hereinafter referred to as "ring atoms");

n is an integer of 1 to 4;

$Ar_1$ to $Ar_4$ are independently a substituted or unsubstituted aryl group including 6 to 30 ring carbon atoms, or a substituted or unsubstituted heteroaryl group including 5 to 30 ring atoms;

$Ra_1$ is a hydrogen atom, a substituted or unsubstituted aryl group including 6 to 30 ring carbon atoms, a substituted or unsubstituted heteroaryl group including 5 to 30 ring atoms, a substituted or unsubstituted alkyl group including 1 to 30 carbon atoms, a substituted or unsubstituted fluoroalkyl group including 1 to 30 carbon atoms, a substituted or unsubstituted cycloalkyl group including 3 to 30 carbon atoms, a silyl group which may be substituted by a substituted or unsubstituted alkyl group including 1 to 30 carbon atoms and/or an unsubstituted aryl group including 6 to 30 ring carbon atoms, a cyano group, a substituted or unsubstituted alkoxy group including 1 to 30 carbon atoms, a substituted or unsubstituted aryloxy group including 6 to 30 ring carbon atoms, a substituted or unsubstituted aralkyl group including 7 to 30 carbon atoms, a hydroxyl group, a nitro group, an amino group which may be substituted by a substituted or unsubstituted alkyl group including 1 to 30 carbon atoms and/or an unsubstituted aryl group including 6 to 30 ring carbon atoms, a carboxy group or $P(=O)(R_b)(R_c)$; and Rb and Rc are independently a hydrogen atom, a substituted or unsubstituted aryl group including 6 to 30 ring carbon atoms, a substituted or unsubstituted heteroaryl group including 5 to 30 ring atoms, a substituted or unsubstituted alkyl group including 1 to 30 carbon atoms, or a substituted or unsubstituted fluoroalkyl group including 1 to 30 carbon atoms.

It is preferred that the compound of the invention be a compound represented by the following formula (2):

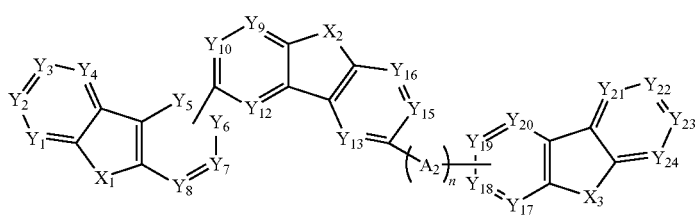

(2)

wherein in the formula (2), $X_1$ to $X_3$ are the same as $X_1$ to $X_3$ in the formula (1), respectively;

$Y_1$ to $Y_4$, $Y_9$, $Y_{10}$, $Y_{12}$, $Y_{13}$, $Y_{15}$, $Y_{16}$ and $Y_{21}$ to $Y_{24}$ are independently $C(Ra_2)$ or N;

one of $Y_5$ to $Y_8$ is a carbon atom being in a single bonded state, and the remaining $Y_5$ to $Y_8$ are independently $C(Ra_2)$ or N;

one of $Y_{17}$ to $Y_{20}$ which bonds to $A_2$ is a carbon atom, and the remaining $Y_{17}$ to $Y_{20}$ are independently $C(Ra_2)$ or N;

$A_2$ is O, S, $Si(Ar_1)(Ar_2)$, $P(=O)(Ar_3)(Ar_4)$, a substituted or unsubstituted arylene group including 6 to 30 ring carbon atoms, or a substituted or unsubstituted heteroarylene group including 5 to 30 ring atoms excluding a carbazolylene group;

$Ar_1$ to $Ar_4$ are the same as $Ar_1$ to $Ar_4$ in the formula (1), respectively;

$Ra_2$ is a hydrogen atom, a substituted or unsubstituted aryl group including 6 to 30 ring carbon atoms, a substituted or unsubstituted heteroaryl group including 5 to 30 ring atoms excluding a carbazole group, a substituted or unsubstituted alkyl group including 1 to 30 carbon atoms, a substituted or unsubstituted fluoroalkyl group including 1 to 30 carbon atoms, a substituted or unsubstituted cycloalkyl group including 3 to 30 carbon atoms, a silyl group which may be substituted by a substituted or unsubstituted alkyl group including 1 to 30 carbon atoms and/or an unsubstituted aryl group including 6 to 30 ring carbon atoms, a cyano group, a substituted or unsubstituted alkoxy group including 1 to 30 carbon atoms, a substituted or unsubstituted aryloxy group including 6 to 30 ring carbon atoms, a substituted or unsubstituted aralkyl group including 7 to 30 carbon atoms, a hydroxy group, a nitro group, an amino group which may be substituted by a substituted or unsubstituted alkyl group including 1 to 30 carbon atoms and/or an unsubstituted aryl group including 6 to 30 ring carbon atoms, a carboxy group or $P(=O)(R_b)(R_c)$; and Rb and Rc are the same as Rb and Rc in the formula (1), respectively.

It is more preferred that the compound of the invention be a compound represented by the following formula (3):

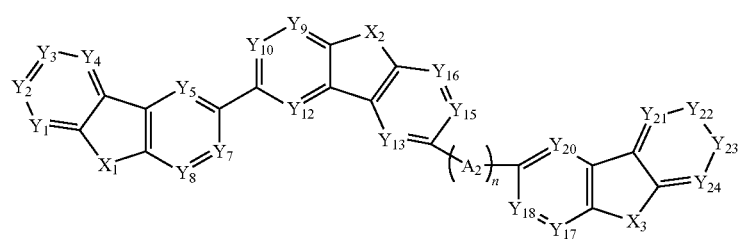

(3)

wherein in the formula (3), $Y_1$ to $Y_5$, $Y_7$ to $Y_{10}$, $Y_{12}$, $Y_{13}$, $Y_{15}$, $Y_{16}$ to $Y_{18}$ and $Y_{20}$ to $Y_{24}$ are independently $C(Ra_2)$ or N; and $X_1$ to $X_3$, $A_2$, n, $Ra_2$ are the same as $X_1$ to $X_3$, $A_2$, n, $Ra_2$ in the formula (2), respectively.

It is further preferred that the compound of the invention be a compound represented by the following formula (4):

By selecting appropriately the bonding position of the three fused aromatic rings, a high triplet energy that does not impair the luminous efficiency of a blue phosphorescent complex can be maintained, whereby a highly efficient organic EL device can be realized.

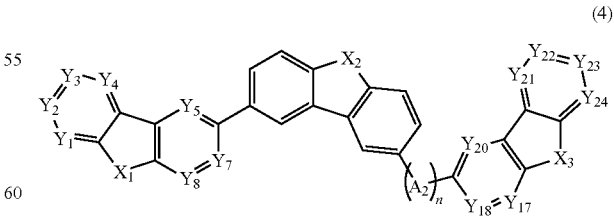

(4)

In the formula (4), $X_1$ to $X_3$, $Y_1$ to $Y_5$, $Y_7$, $Y_8$, $Y_{17}$, $Y_{18}$, $Y_{20}$ to $Y_{24}$, $A_2$ and n are as defined in the formula (3).

$A_1$ and $A_2$ in the above formulas (1) to (4) are preferably a substituted or unsubstituted arylene group having 6 to 30 ring carbon atoms.

Further, it is preferred that $A_1$ and $A_2$ in in the above formulas (1) to (4) be a substituted or unsubstituted heteroarylene group having 5 to 20 ring atoms excluding a carbazole group.

By incorporating three or more fused aromatic rings within the molecule, selecting the bonding positions thereof appropriately to keep the triplet energy at a high level that does not impair the luminous efficiency of a blue phosphorescent complex, and by allowing the molecules to take a linear structure, the orientation of the molecules can be improved. As a result, the transporting properties of carriers can be improved, and the device can be driven at a low voltage.

It is particularly preferred that the compound of the invention be a compound represented by the following formula (5):

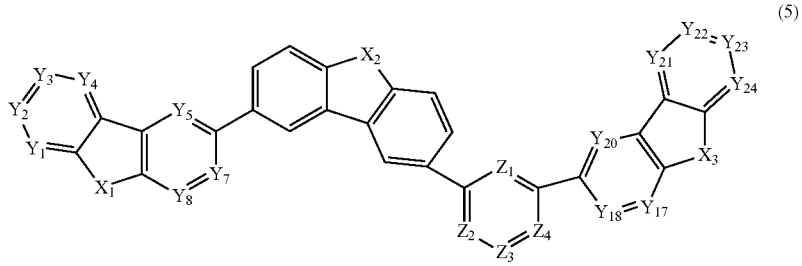

(5)

In the formula (5), $Z_1$ to $Z_4$ are independently $C(Ra_2)$ or N.

$X_1$ to $X_3$, $Y_1$ to $Y_5$, $Y_7$, $Y_8$, $Y_{17}$, $Y_{18}$, and $Y_{20}$ to $Y_{24}$ are as defined in the formula (4). $Ra_2$ is as defined in the formula (2).

A detailed explanation will be made on each group in the formulas (1) to (5) and a substituent when each group has a substituent.

As the aryl group or the arylene group having 6 to 30 ring carbon atoms, a monovalent group (aryl group) or a divalent group (arylene group) of a non-fused aromatic ring and a fused aromatic ring can be given. More specifically, a phenyl group, a naphthyl group, a phenanthryl group, a biphenylyl group, a terphenylyl group, a fluoranthenyl group, a triphenylenyl group, a phenanthrenyl group, a 9,9-dimethylfluorenyl group or the like can be given. It is preferred that the aryl group or the arylene group have 6 to 20, more preferably 6 to 18, ring carbon atoms.

The aryloxy group having 6 to 30 ring carbon atoms is represented by —OX, and as examples of X, examples of the above-mentioned aromatic hydrocarbon ring group of X can be given. The aryloxy group is a phenoxy group, for example.

As the heteroaryl group or the heteroarylene group having 5 to 30 ring atoms, a monovalent group (heteroaryl group) or a divalent group (heteroarylene group) of a non-fused heterocyclic aromatic ring and a fused heterocyclic aromatic ring can be given. More specifically, as the heteroaryl group, a pyrrolyl group, a pyrazinyl group, a pyridinyl group, a pyrimidinyl group, a pyridazinyl group, a triazinyl group, an indolyl group, an isoindolyl group, a fury group, a benzofuranyl group, an isobenzofuranyl group, a dibenzofuranyl group, a dibenzothiophenyl group, a quinolyl group, an isoquinolyl group, a quinoxalinyl group, a carbazolyl group, an azacarbazolyl group, a phenanthridinyl group, an acridinyl group, a phenanthrolinyl group, a thienyl group, a pyrrolidinyl group, dioxanyl group, a piperidinyl group, a morpholinyl group, a piperazinyl group, a carbazolyl group, a thiophenyl group, an oxazolyl group, an oxadiazolyl group, a benzoxazolyl group, a thiazolyl group, a thiadiazolyl group, a benzothiazolyl group, a triazolyl group, an imidazolyl group, a benzimidazolyl group, a pyranyl group, a benzo[c]dibenzofuranyl group or the like can be given. As the heteroarylene group, a divalent group of these can be given. It is preferred that the heteroaryl group or the heteroarylene group have 5 to 20 ring atoms, with 5 to 18 ring atoms being more preferable.

As the alkyl group having 1 to 30 carbon atoms, a linear or branched alkyl group can be given. Specific examples thereof include a methyl group, an ethyl group, a propyl group, an isopropyl group, an n-butyl group, an isobutyl group, a sec-butyl group, a tert-butyl group, an n-pentyl group, an n-hexyl group, an n-heptyl group, an n-octyl group, and a trifluoromethyl group. Of these, a methyl group, an ethyl group, a propyl group, an isopropyl group, an n-butyl group, an isobutyl group, a sec-butyl group and a tert-butyl group can preferably be given. A methyl group, an ethyl group, a propyl group, an isopropyl group, an n-butyl group, a sec-butyl group, a tert-butyl group or the like can preferably be given. The alkyl group has preferably 1 to 20 carbon atoms, more preferably 1 to 10 carbon atoms, with 3 to 6 carbon atoms being further preferable.

The alkoxy group having 1 to 30 carbon atoms is represented by —OY, and as examples of Y, examples of the above-mentioned alkyl group can be given. The alkoxy group is a methoxy group, an ethoxy group and a trifluoromethoxy group, for example.

As the fluoroalkyl group having 1 to 30 carbon atoms, a group in which the above-mentioned alkyl group having 1 to 20 carbon atoms is substituted by one or more fluorine atoms can be given. Specifically, a fluoromethyl group, a difluoromethyl group a trifluoromethyl group, a fluoroethyl group, a trifluoromethylmethyl group, a pentafluoroethyl group or the like can be given. A trifluoromethyl group and a pentafluoroethyl group are preferable.

The cycloalkyl group having 3 to 30 carbon atoms, a cyclopropyl group, a cyclobutyl group, a cyclopentyl group, a cyclohexyl group, a 1-adamantyl group, a 2-adamantyl group, a 1-norbornyl group, a 2-norbornyl group, or the like can be given. A cyclopentyl group and a cyclohexyl group are preferable. It is preferred that the cycloalkyl group have 3 to 20 carbon atoms, with 3 to 12 carbon atoms being more preferable.

As the aralkyl group having 7 to 30 carbon atoms, one obtained by substituting the above-mentioned alkyl group with the above-mentioned aryl group can be given. It is preferred that the aralkyl group have 7 to 20 carbon atoms, with 7 to 18 carbon atoms being more preferable.

The three fused heterocyclic aromatic rings in the formulas (1) to (5) may not be substituted ($Ra_1$, $Ra_2$ are all hydrogens). The fused heterocyclic aromatic ring may have 1, 2 or 3 substituents.

As the substituent if the each of the groups has a substituent, an alkyl group having 1 to 30 carbon atoms, an alkoxy group having 1 to 30 carbon atoms or a fluoroalkyl group having 1 to 30 carbon atoms, an aryl group or an aryloxy group having 6 to 30 ring atoms, a heteroaryl group having 3 to 30 ring atoms, an aralkyl group having 7 to 30 carbon atoms, a silyl group, on alkylsilyl group having 1 to 6 carbon atoms, a fluoro group or a cyano group can be given.

Hereinbelow, specific examples of the compound of the invention represented by the above formulas (1) to (5) (hereinafter, comprehensively, often referred to as the compound of the invention) are shown.

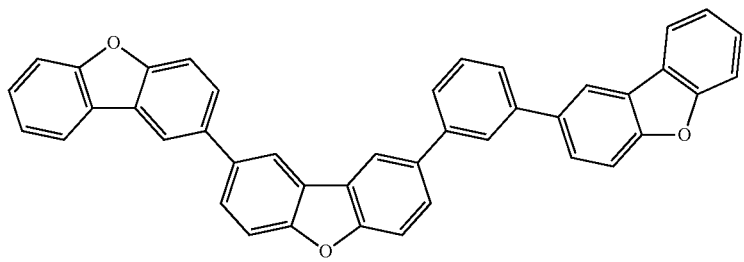

(1)

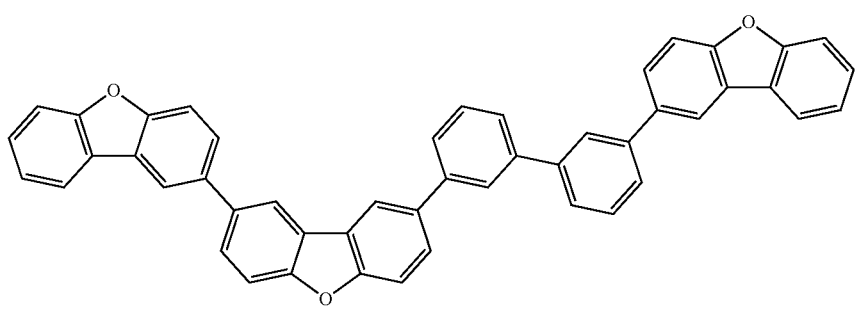

(2)

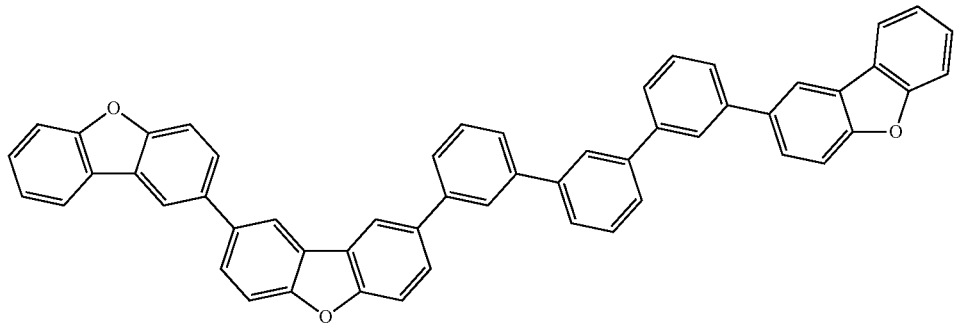

(3)

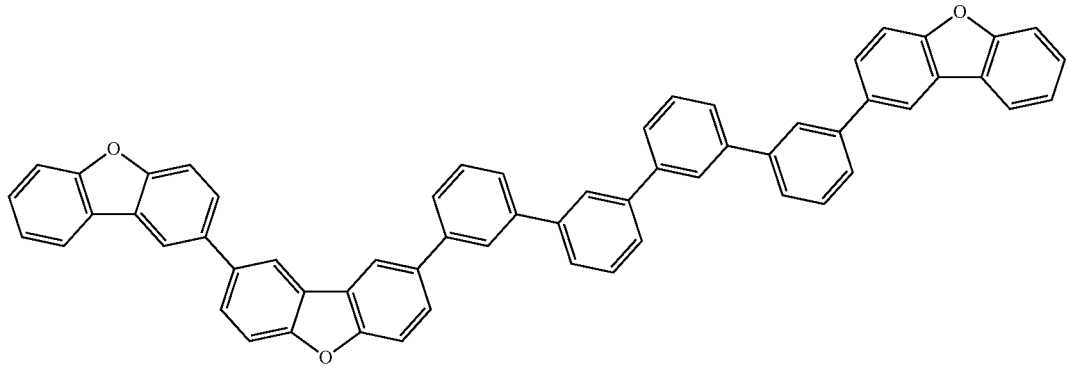

(4)

-continued
(5)
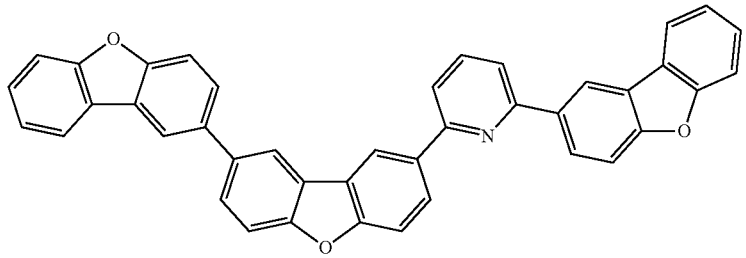
(6)
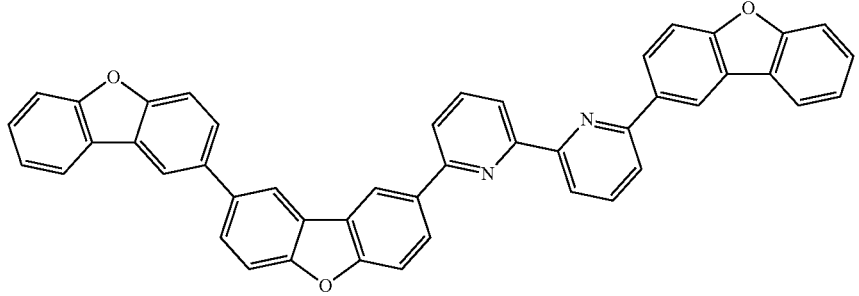
(7)
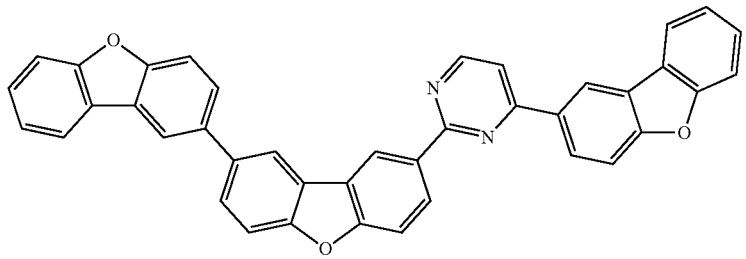
(8)
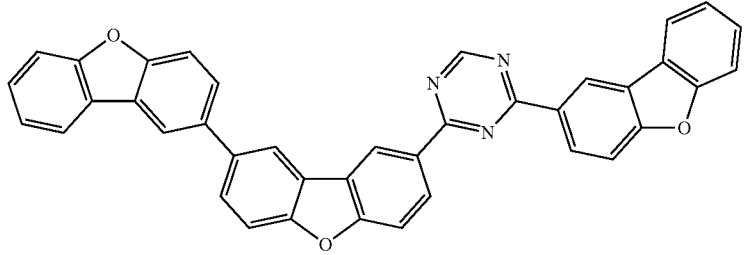
(9)
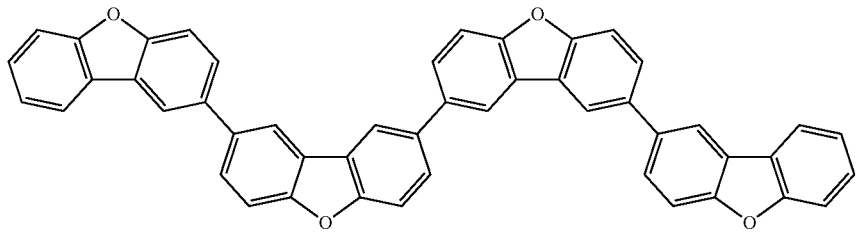
(10)
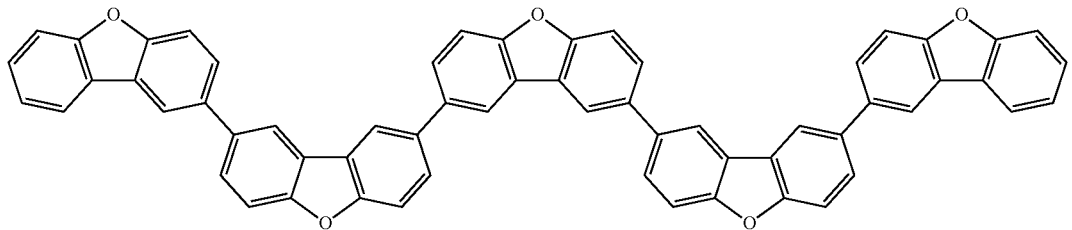

-continued
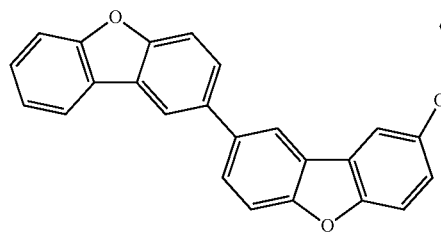
(11)
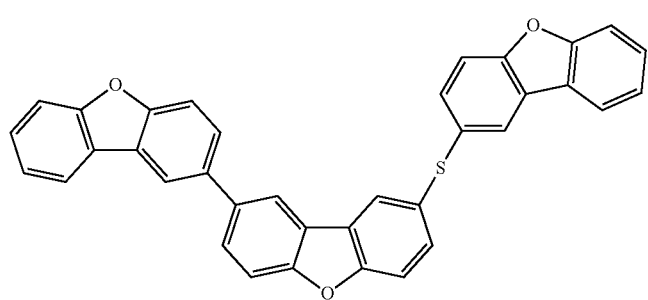
(12)
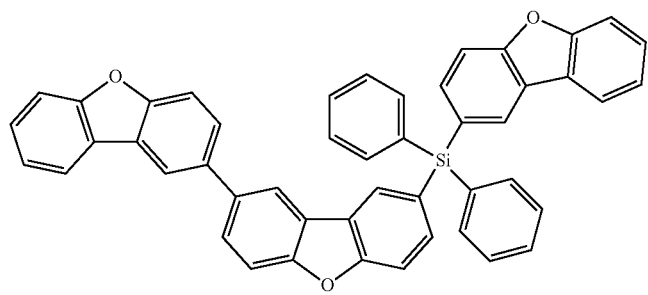
(13)
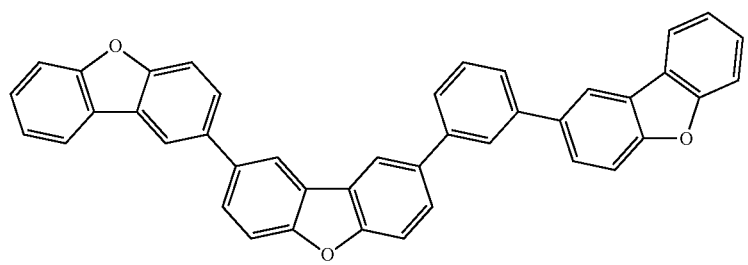
(14)
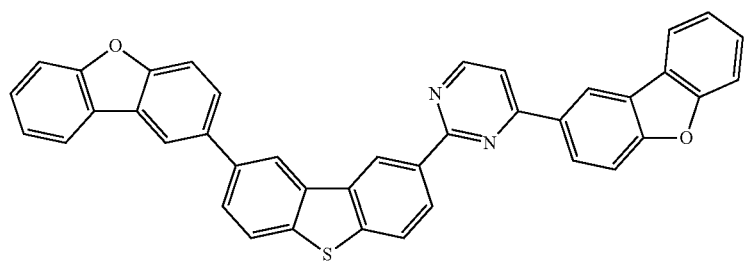
(15)

(16)
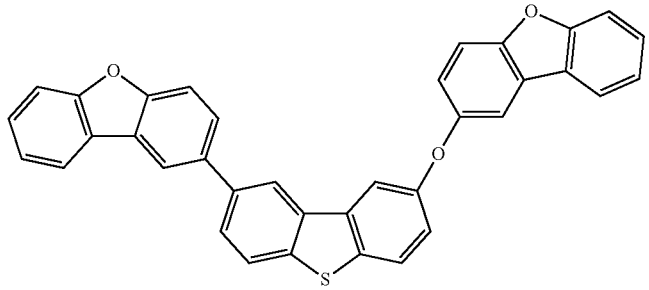
(17)
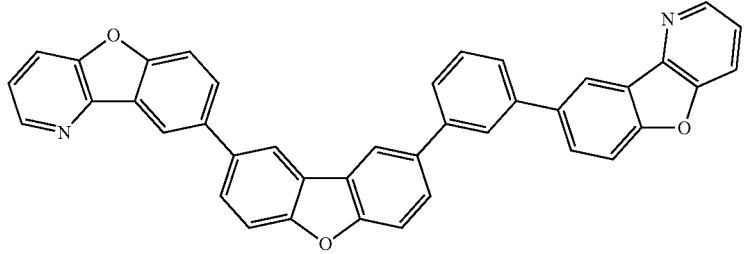
(18)
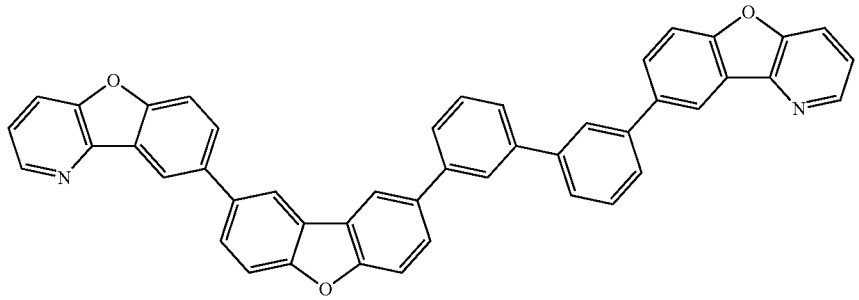
(19)
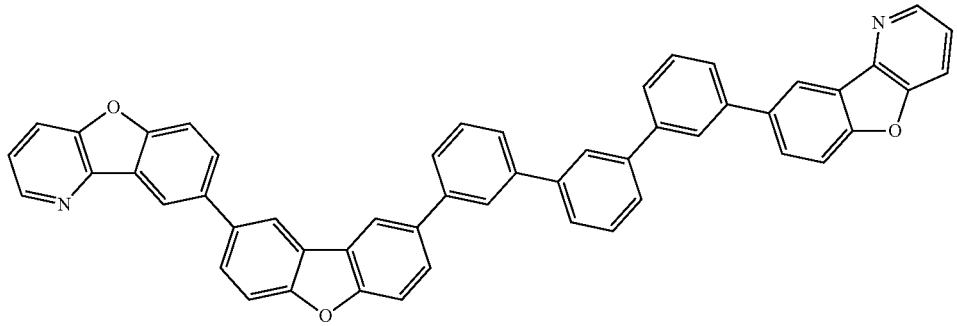
(20)
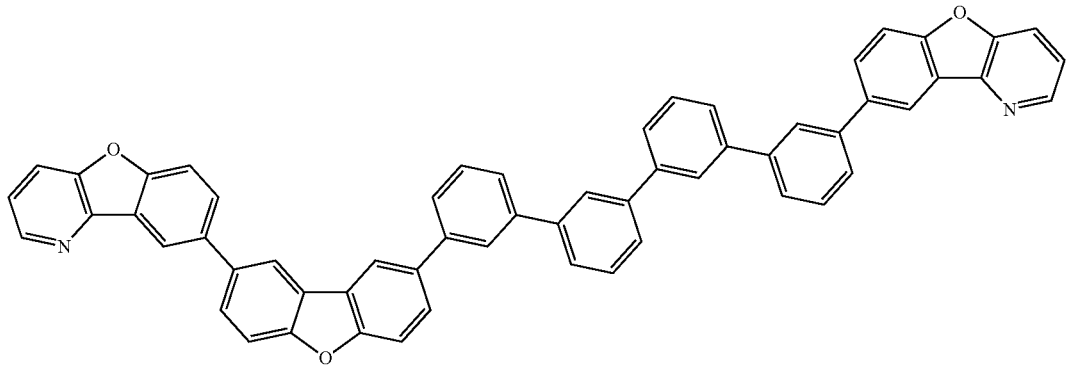

-continued
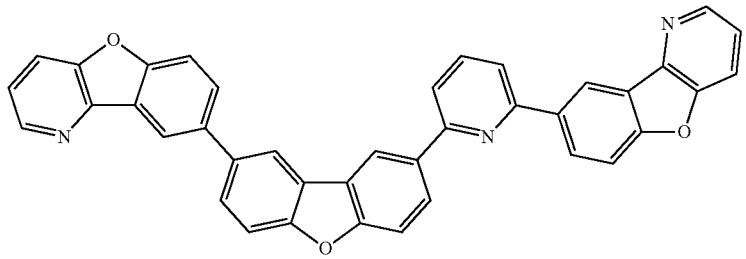
(21)
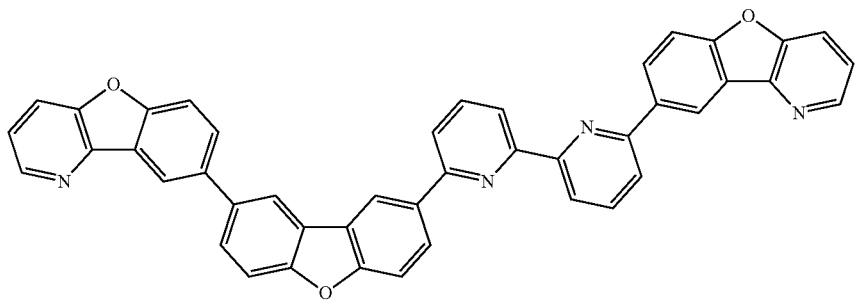
(22)
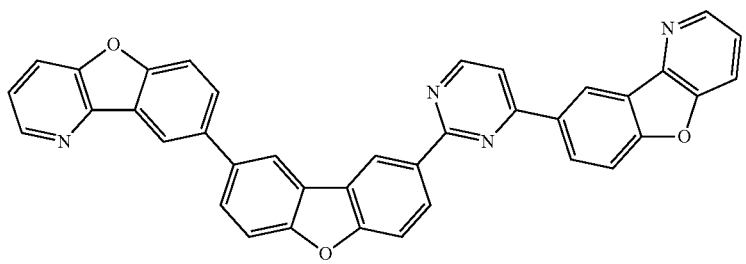
(23)
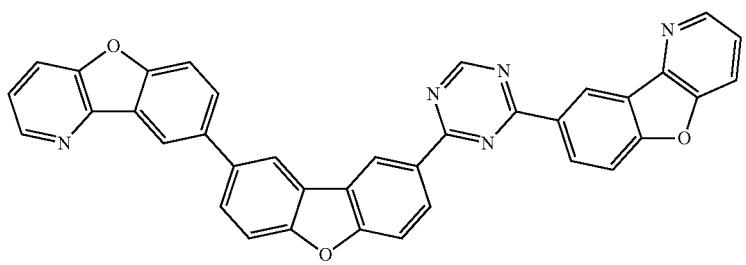
(24)
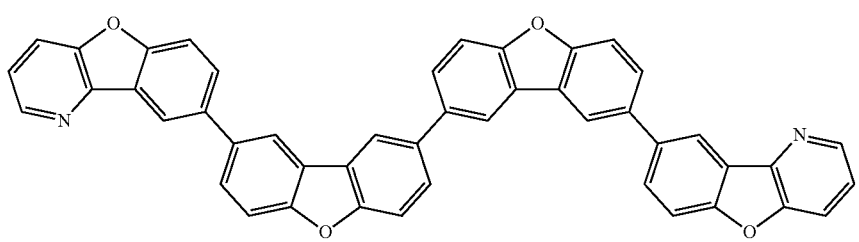
(25)
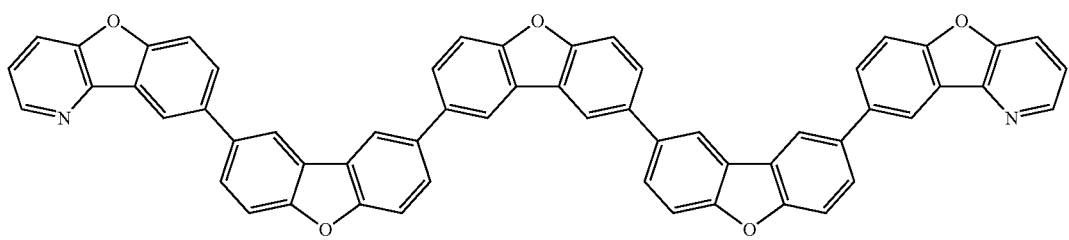
(26)

-continued
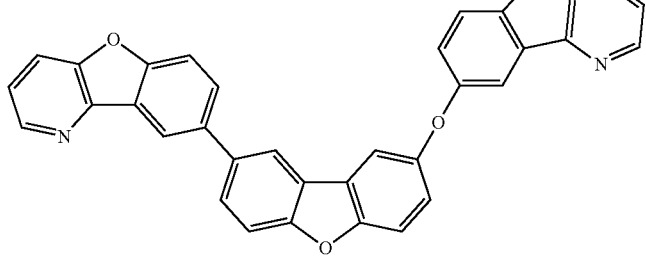
(27)
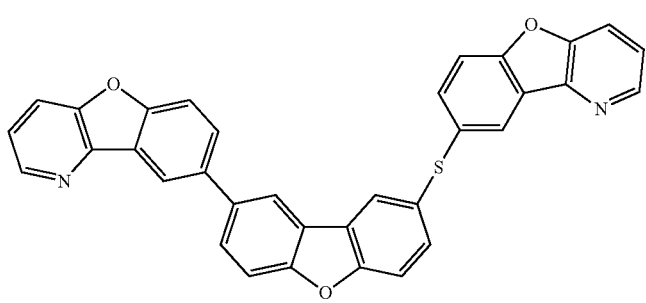
(28)
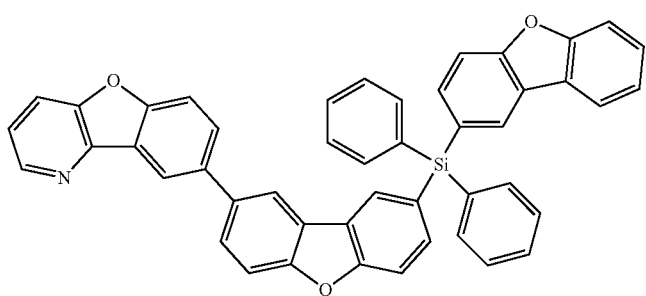
(29)
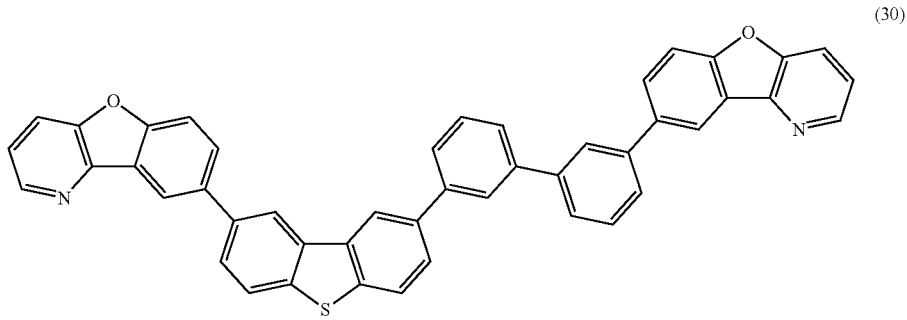
(30)
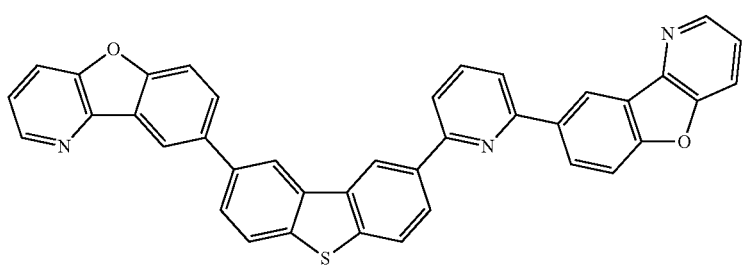
(31)

-continued
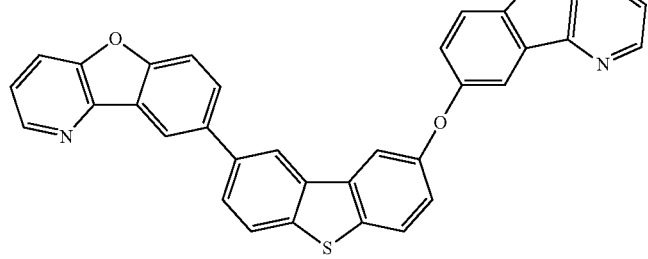
(32)
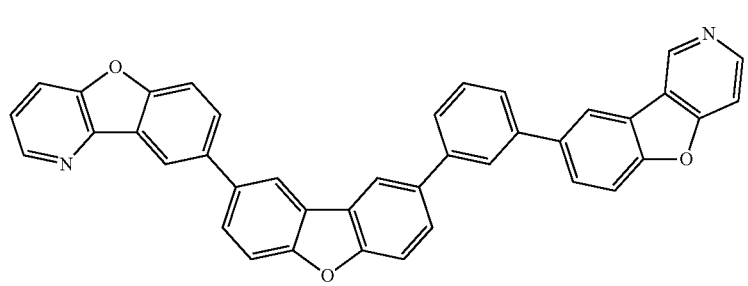
(33)
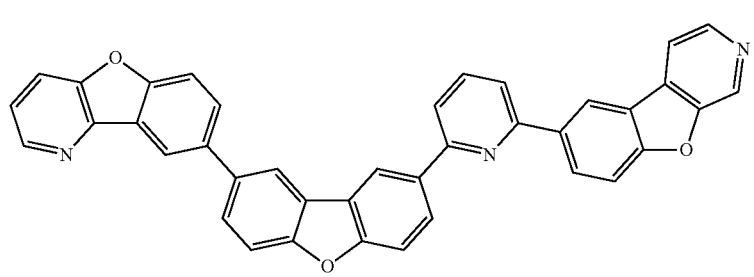
(34)
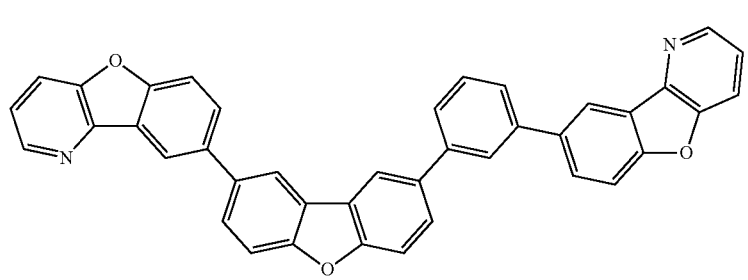
(35)
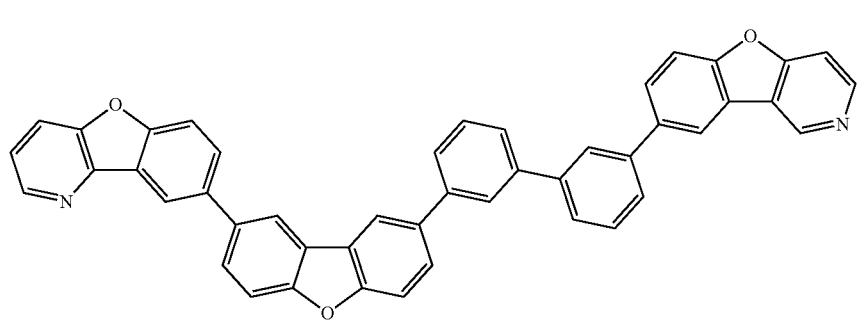
(36)

-continued
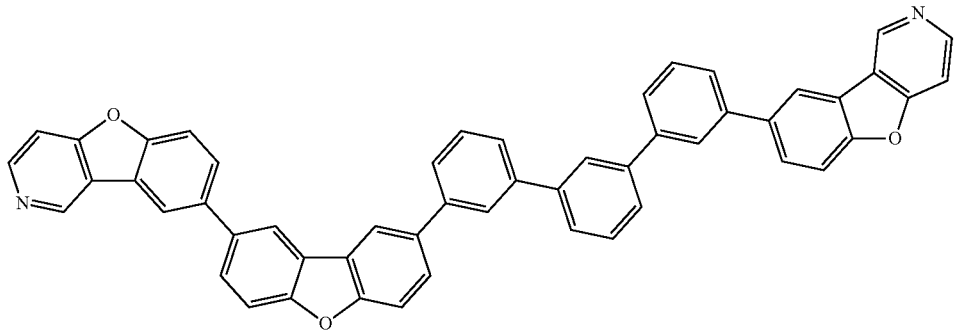
(37)
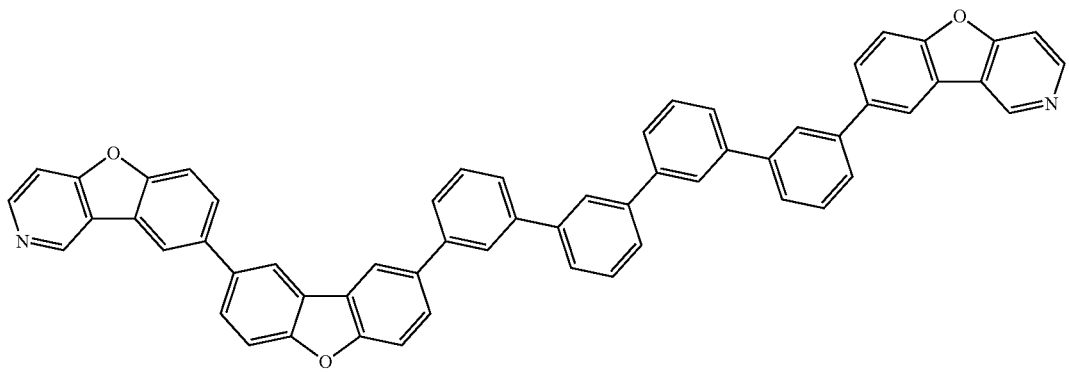
(38)
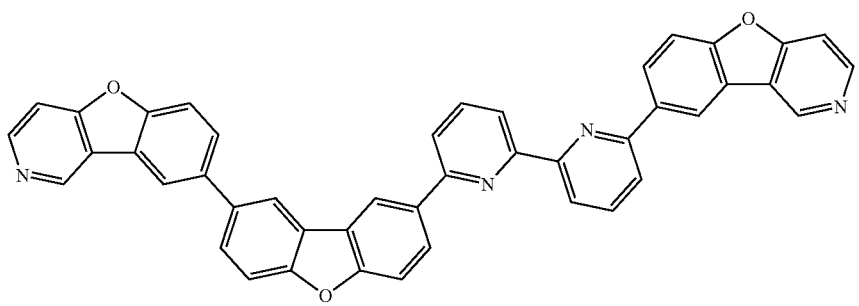
(39)
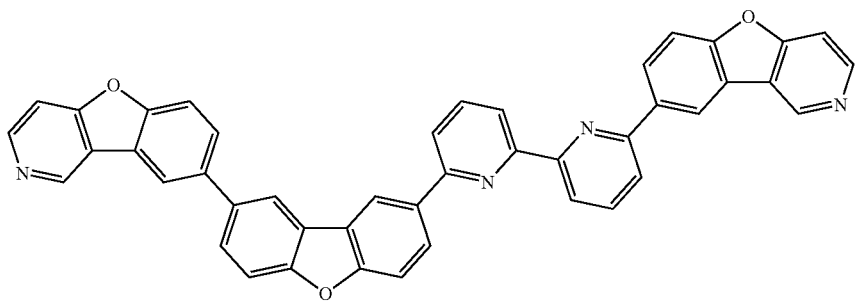
(40)
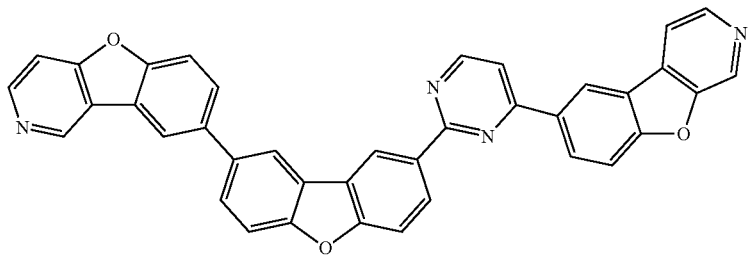
(41)

-continued
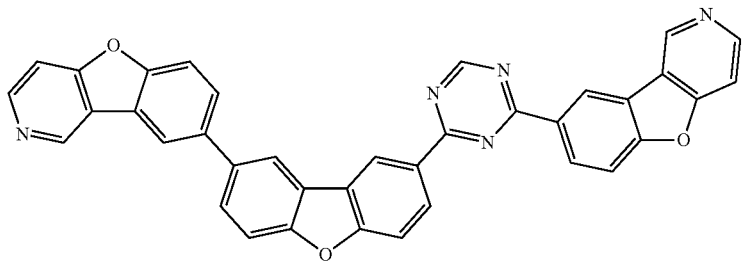
(42)
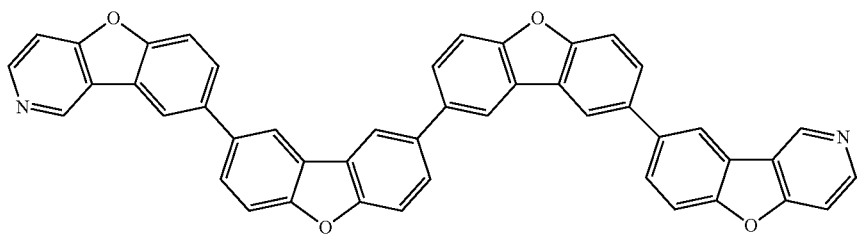
(43)
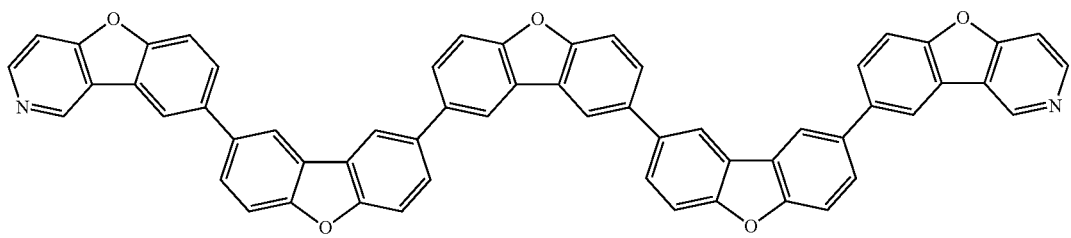
(44)
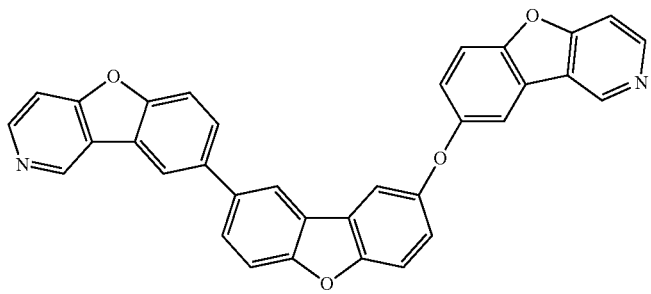
(45)
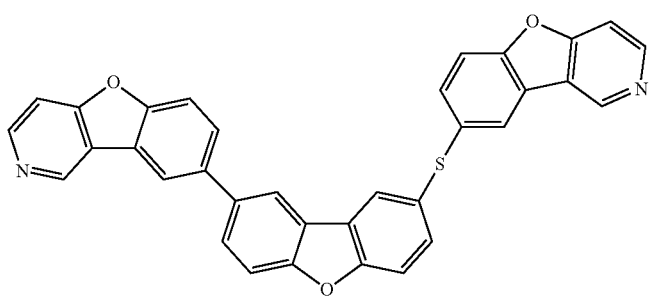
(46)
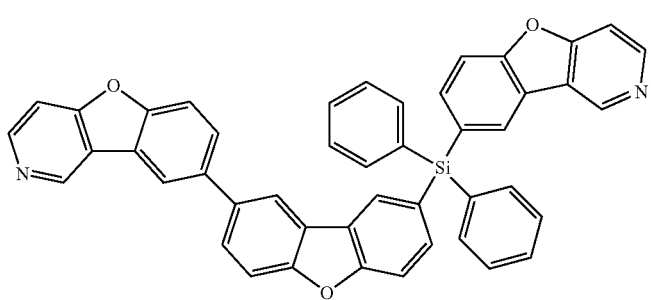
(47)

(48)
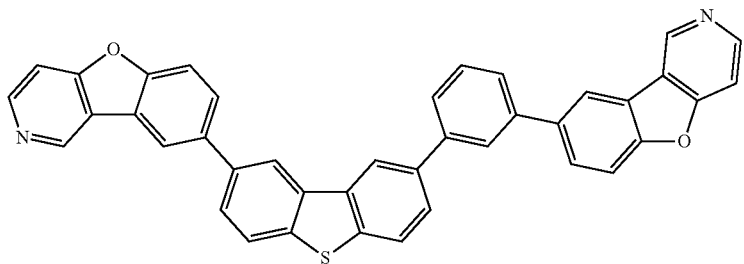
(49)
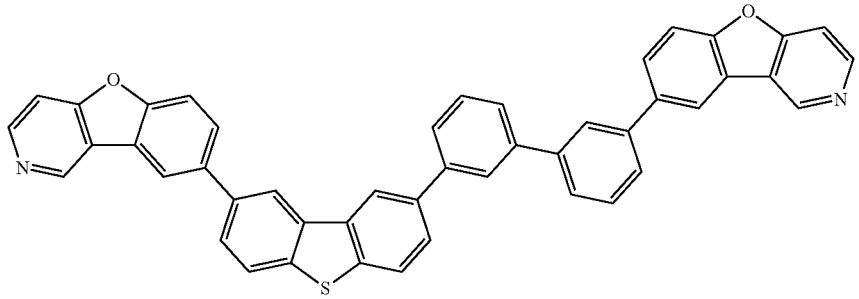
(50)
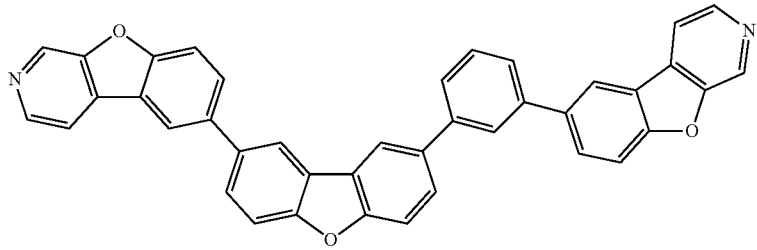
(51)
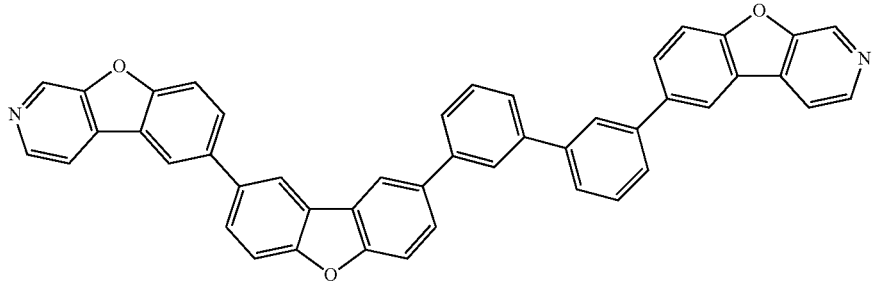
(52)
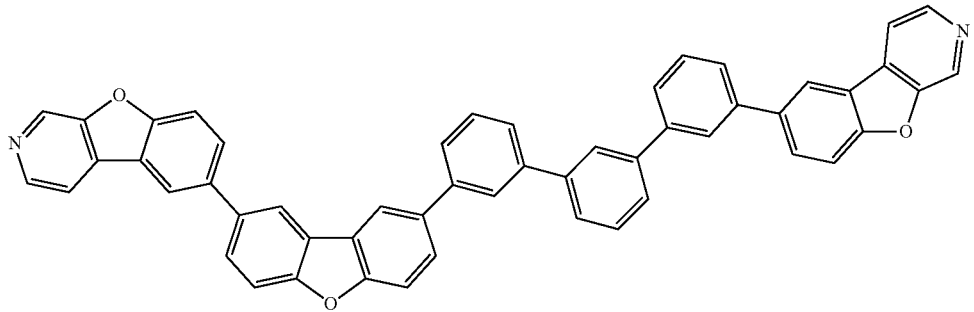

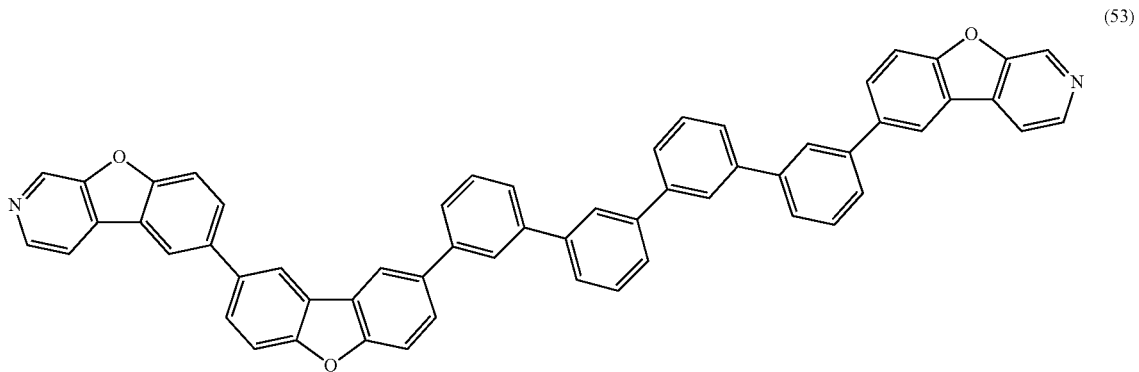
(53)
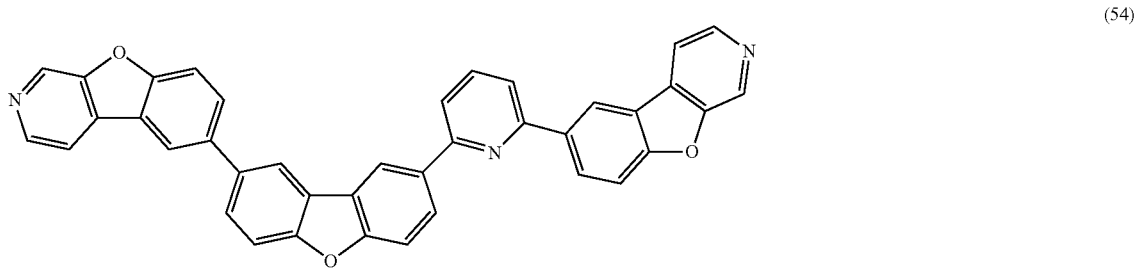
(54)
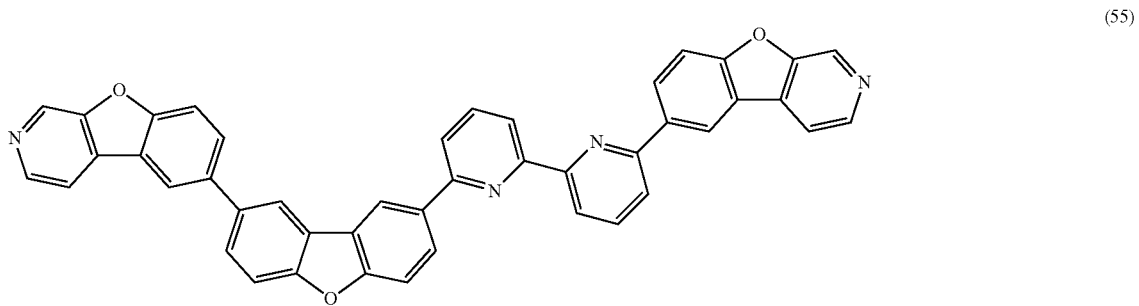
(55)
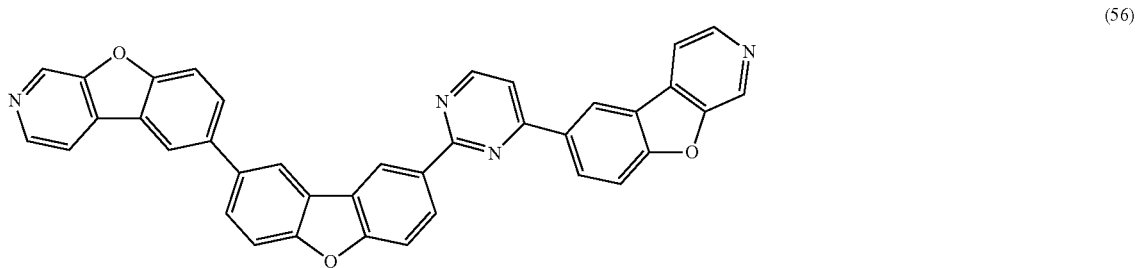
(56)
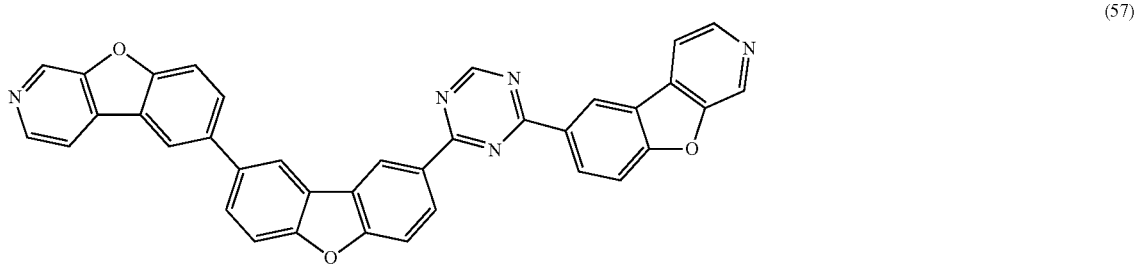
(57)

-continued
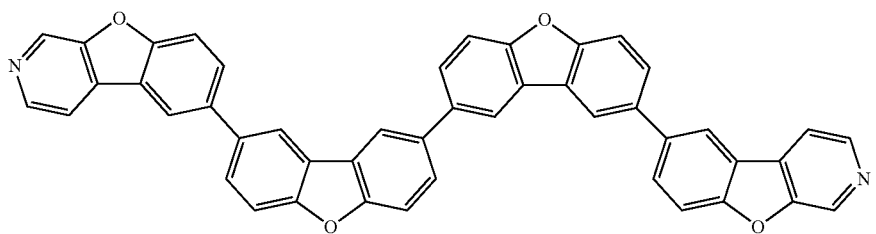
(58)
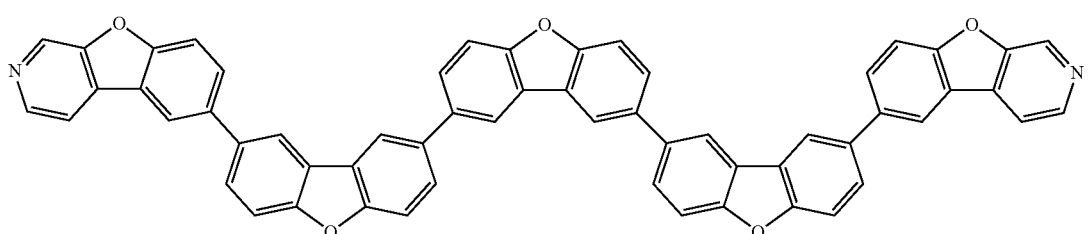
(59)
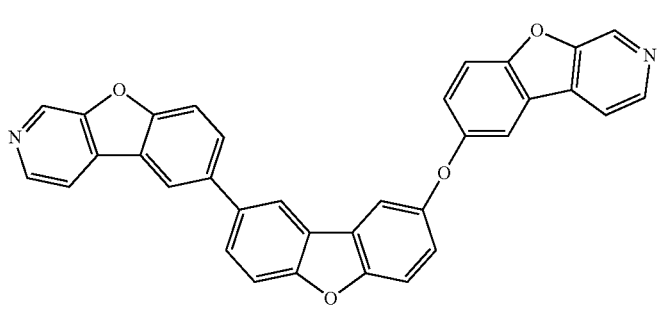
(60)
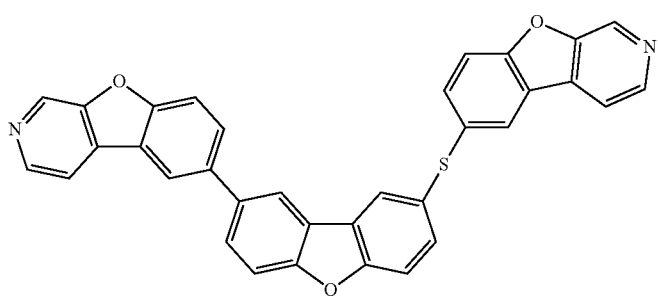
(61)
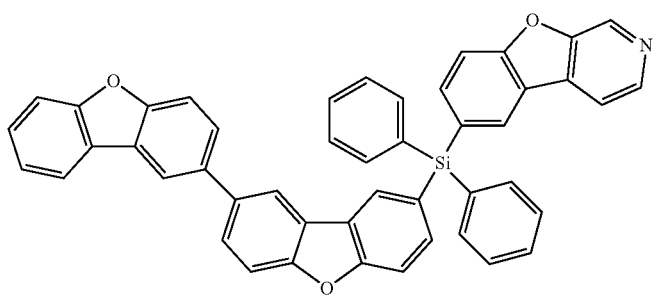
(62)
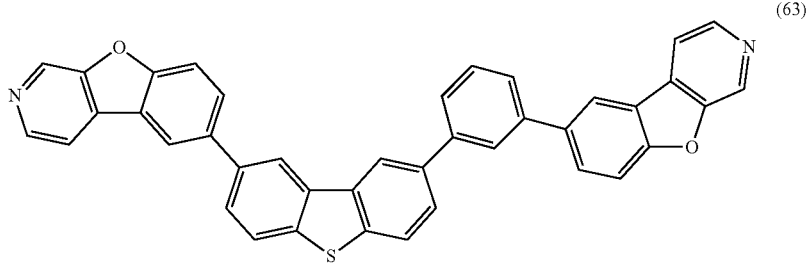
(63)

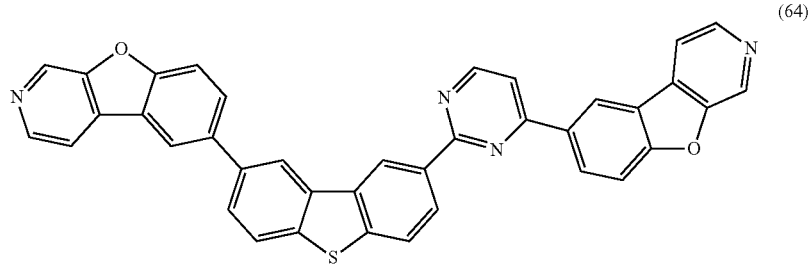
(64)
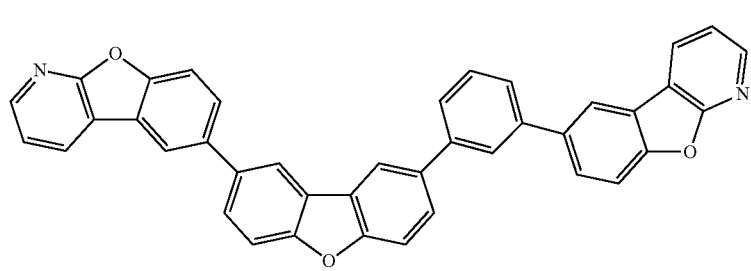
(65)
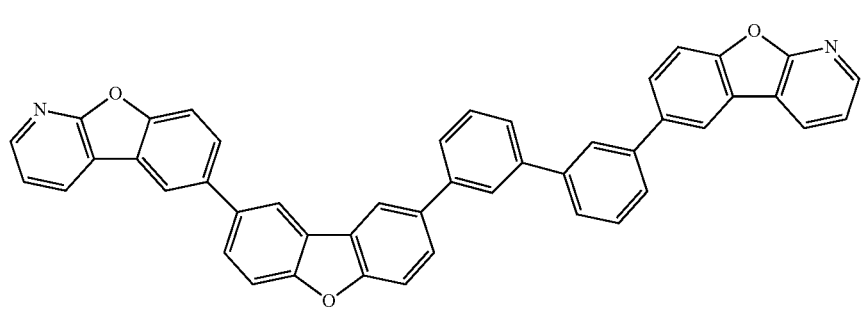
(66)
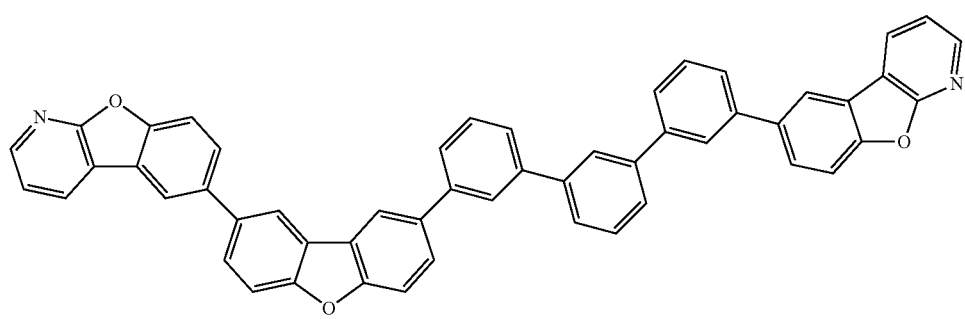
(67)
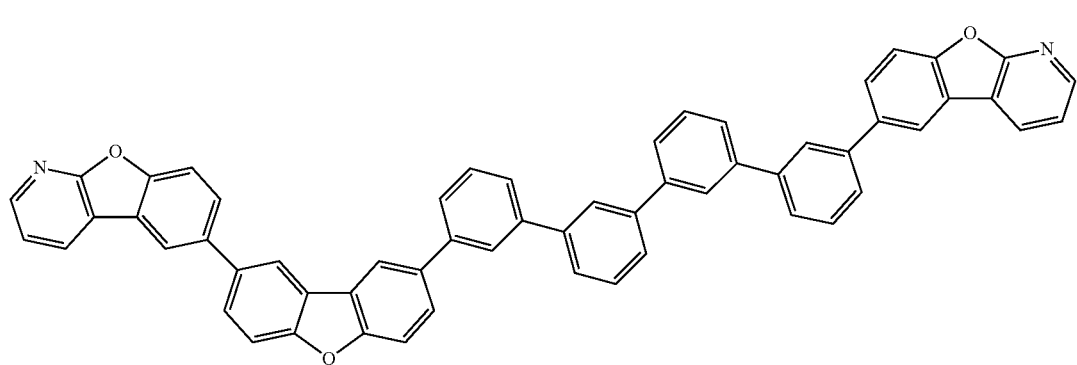
(68)

-continued
(69)
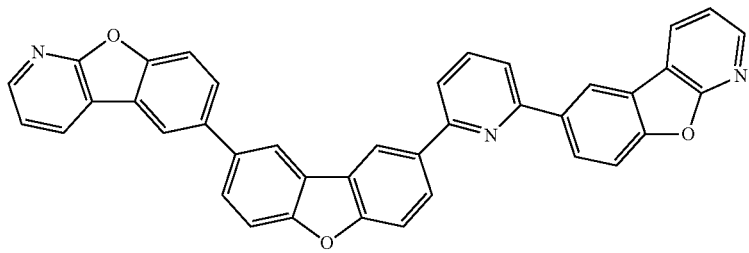
(70)
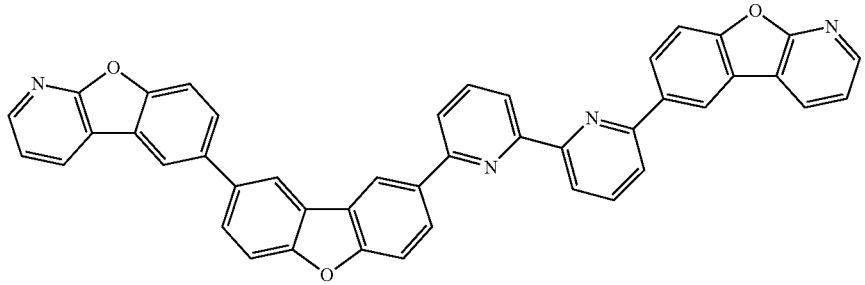
(71)
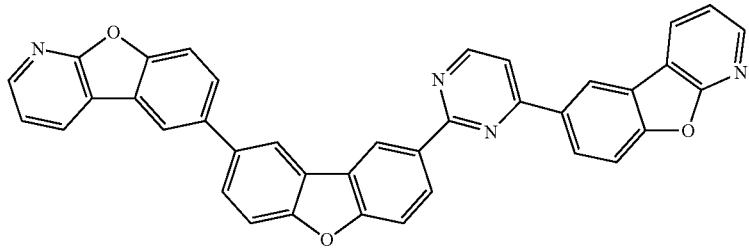
(72)
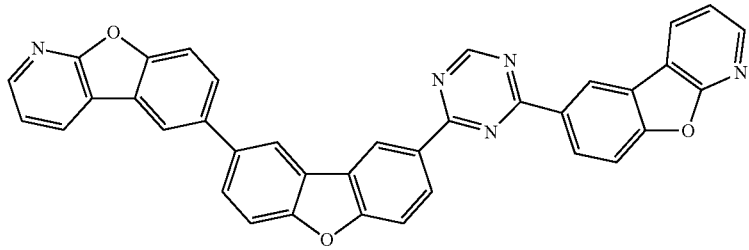
(73)
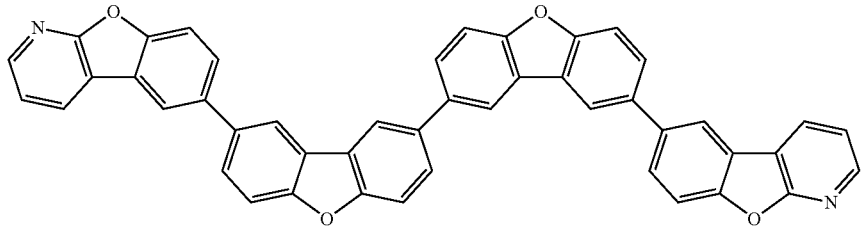
(74)
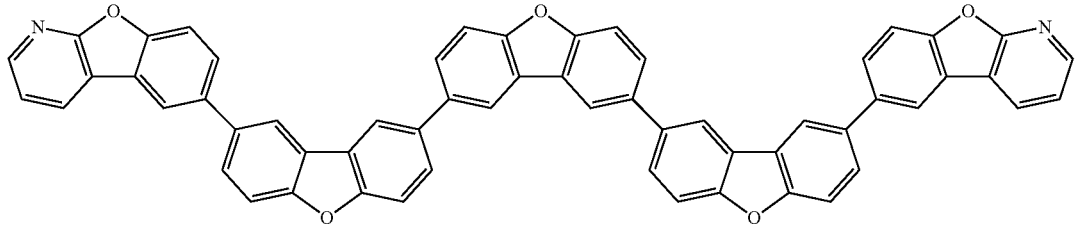

-continued
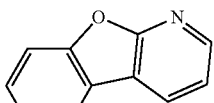
(75)
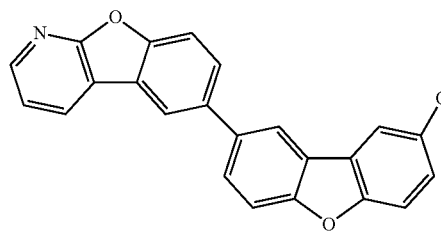
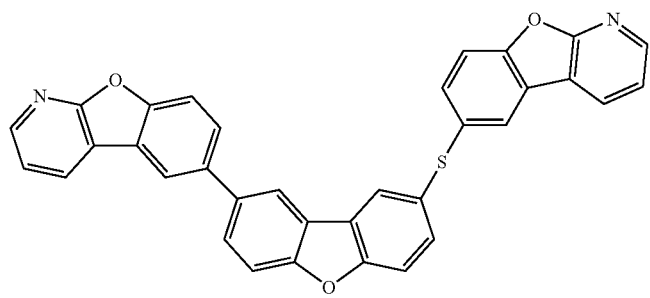
(76)
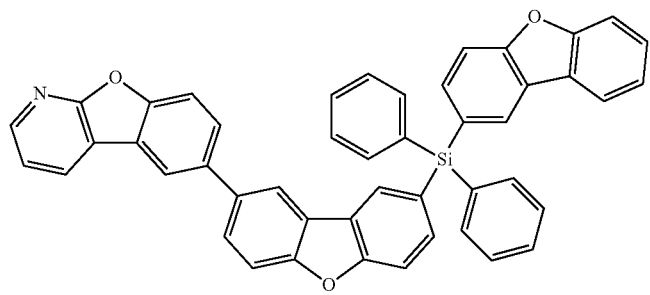
(77)
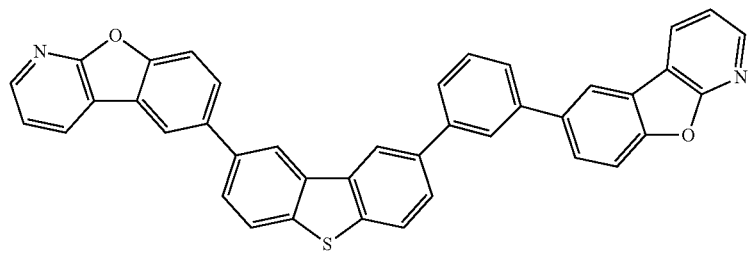
(78)
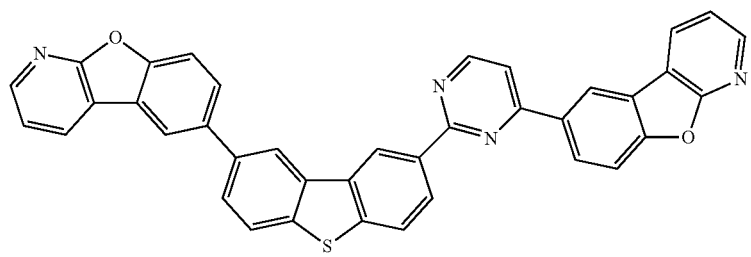
(79)

-continued
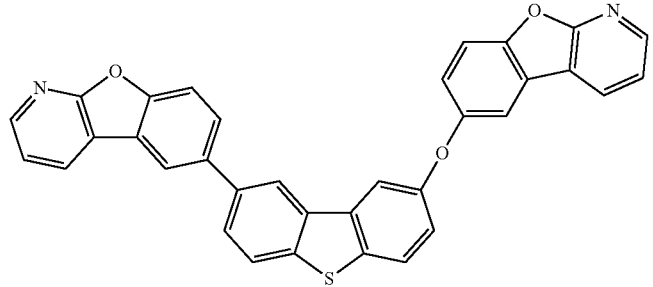 (80)
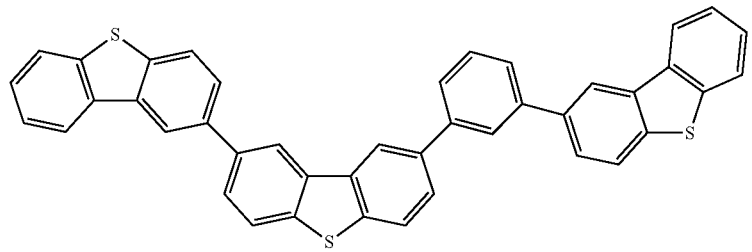 (81)
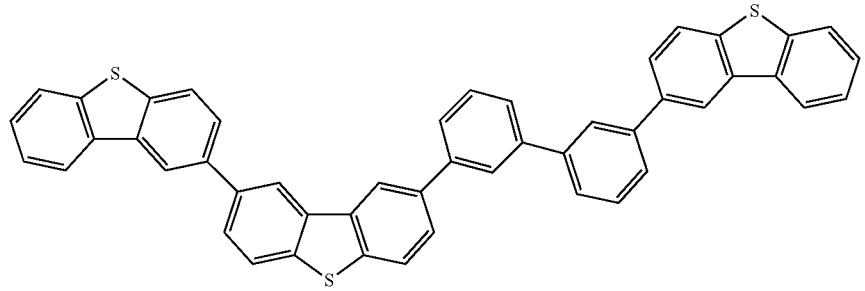 (82)
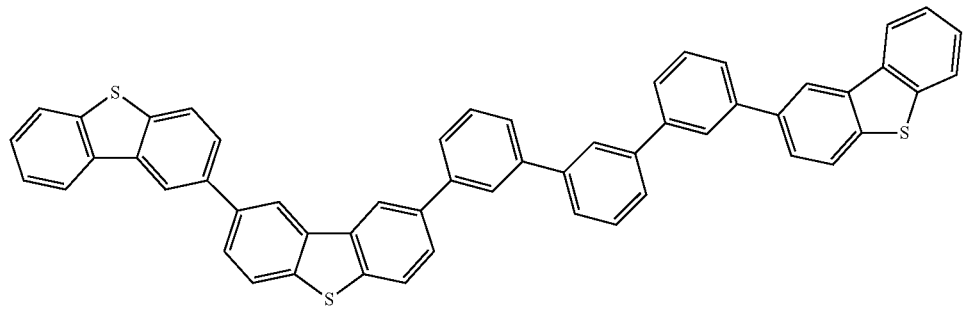 (83)
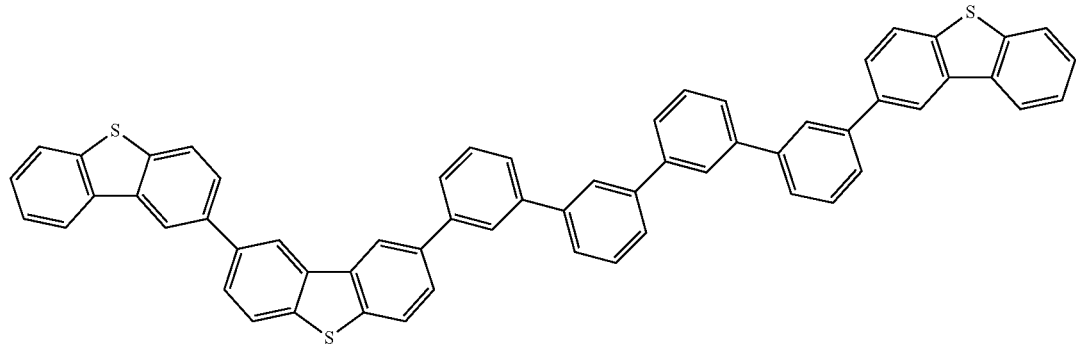 (84)

-continued
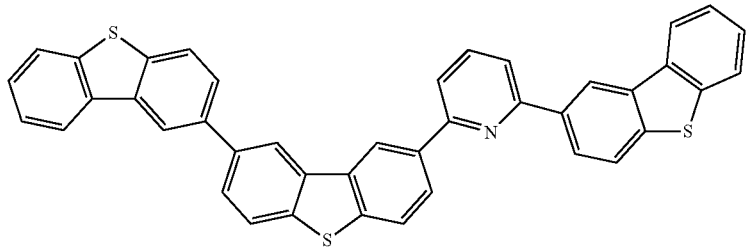
(85)
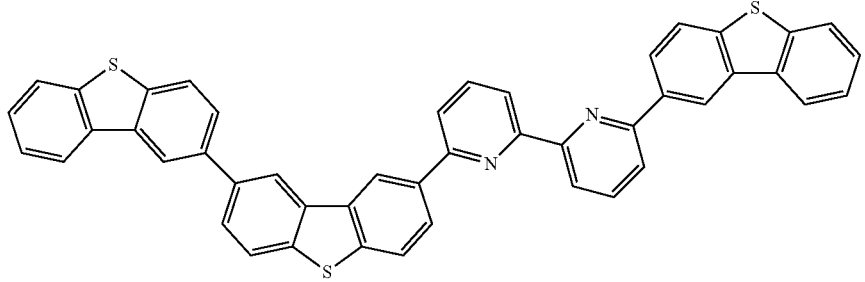
(86)
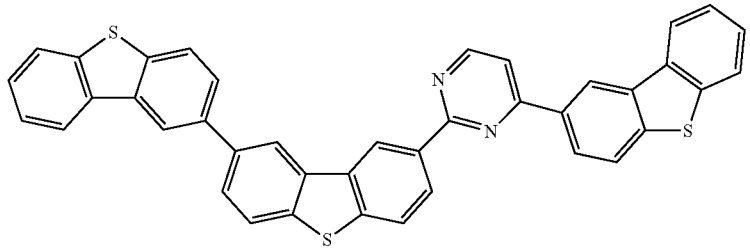
(87)
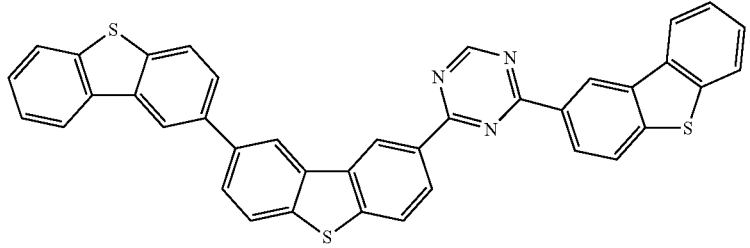
(88)
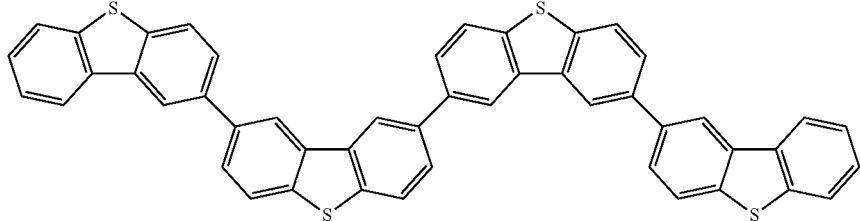
(89)
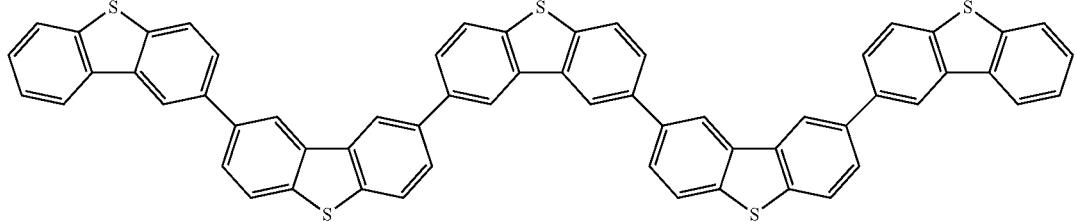
(90)

-continued
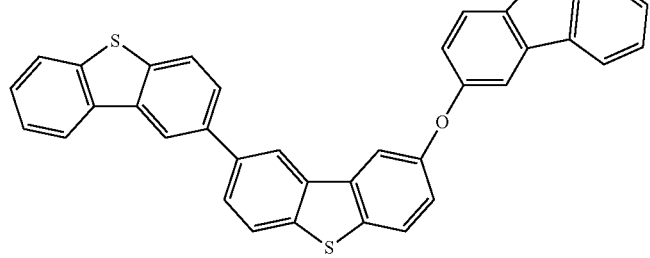
(91)
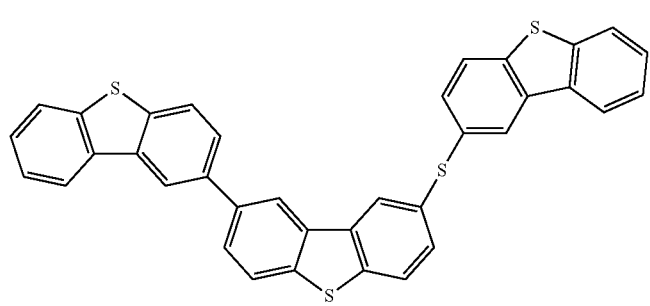
(92)
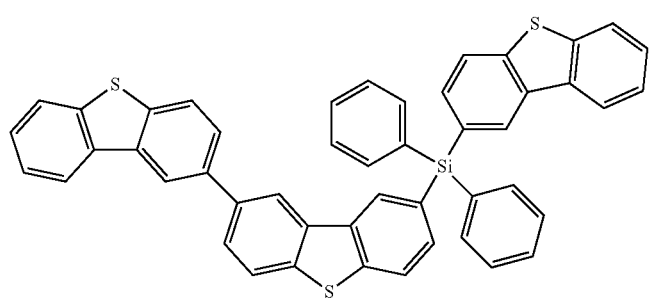
(93)
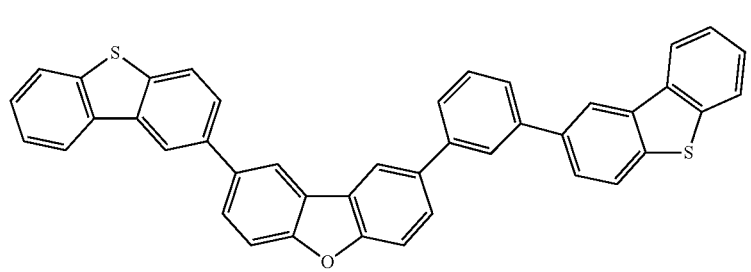
(94)
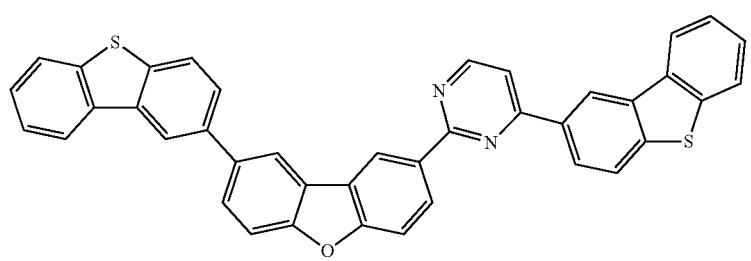
(95)

-continued
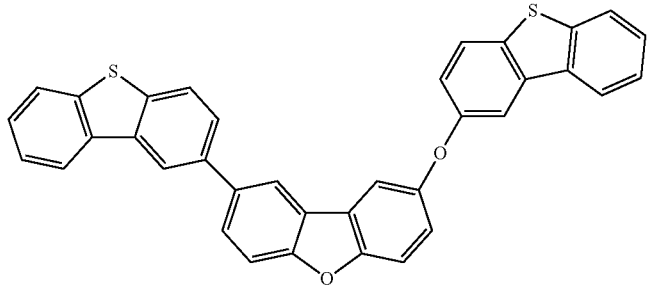
(96)
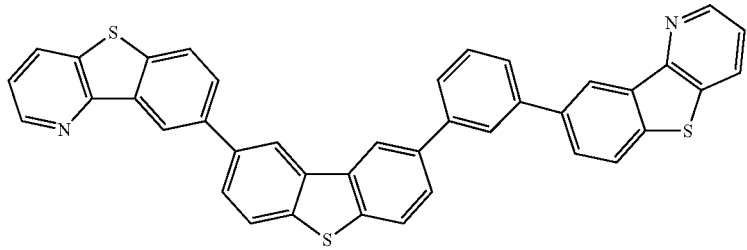
(97)
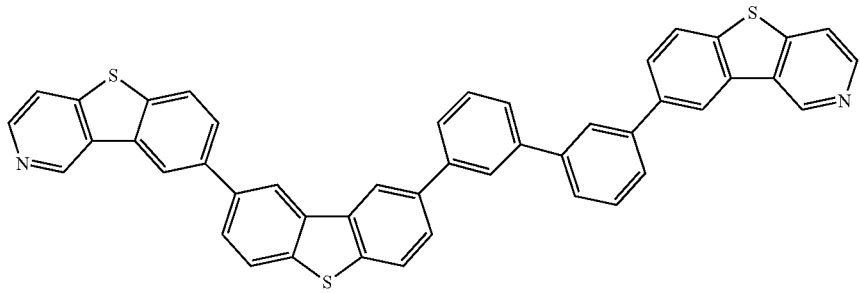
(98)
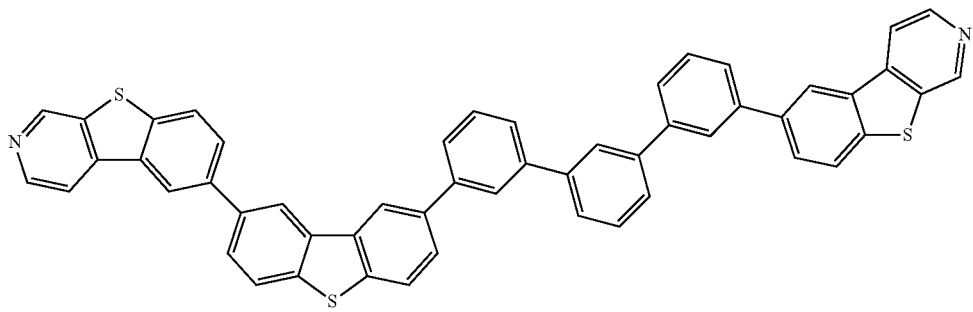
(99)
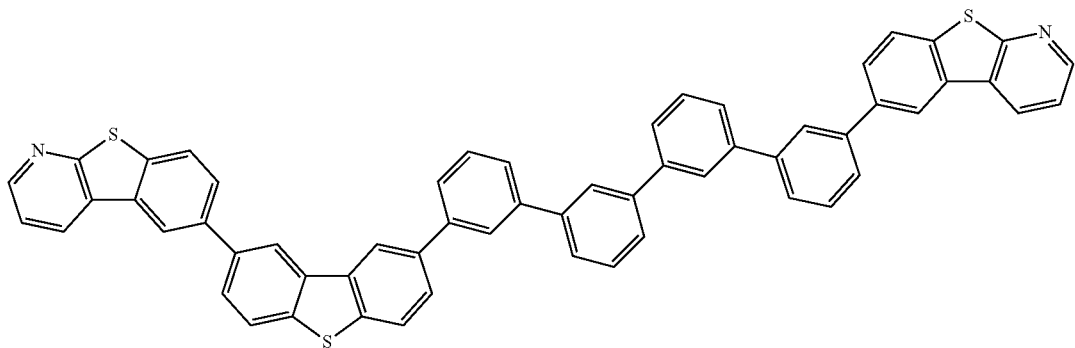
(100)

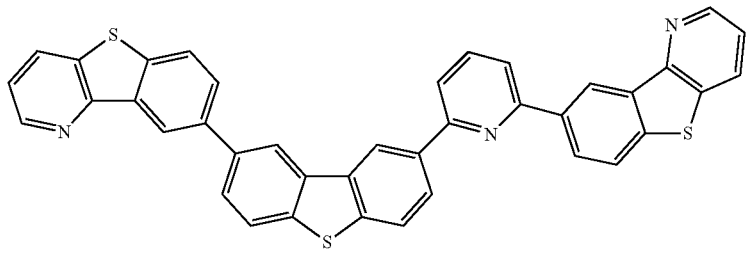
(101)
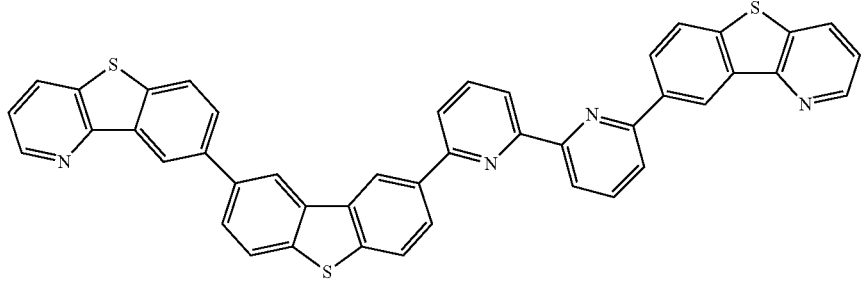
(102)
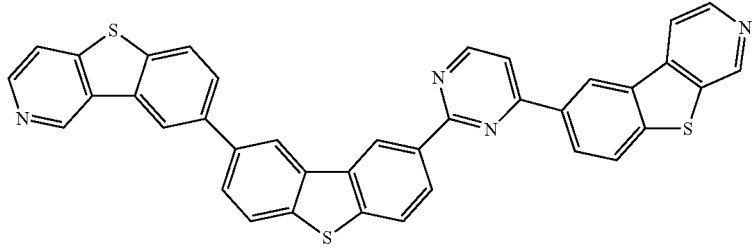
(103)
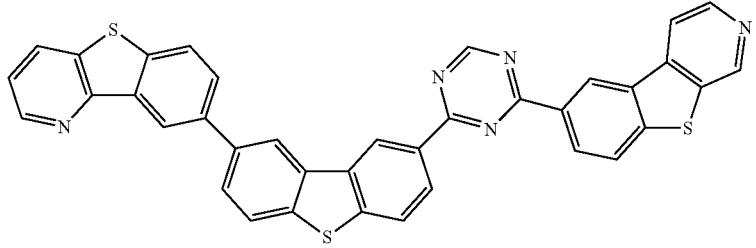
(104)
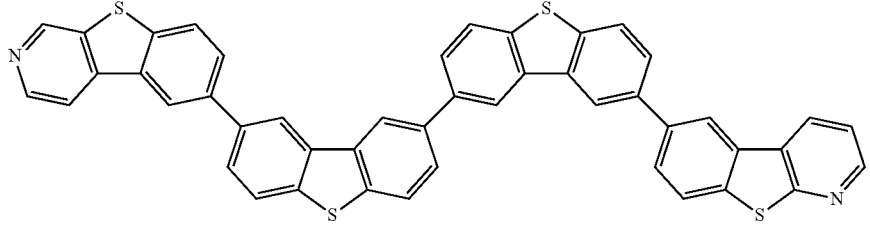
(105)
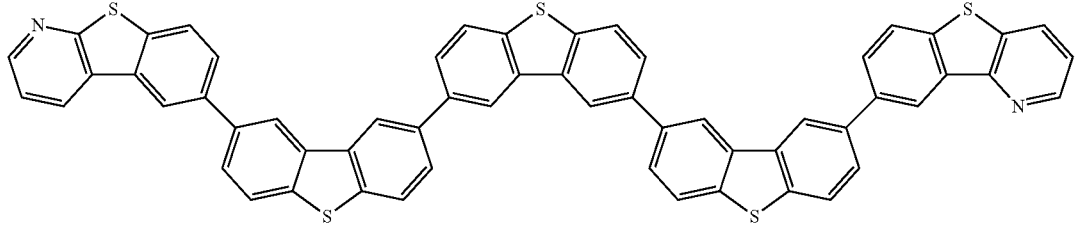
(106)

-continued
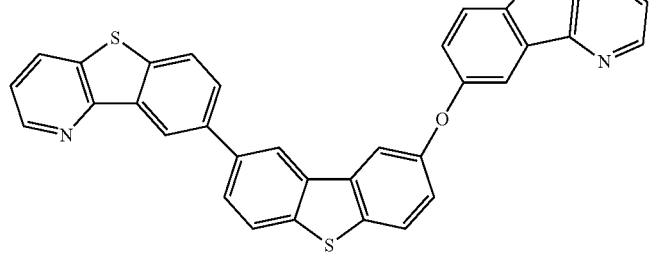
(107)
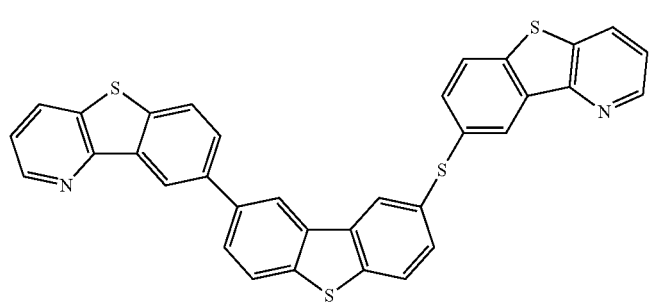
(108)
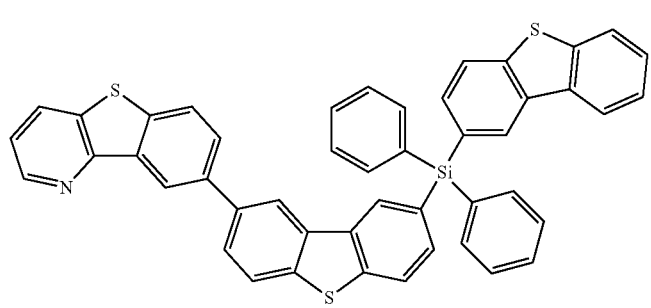
(109)
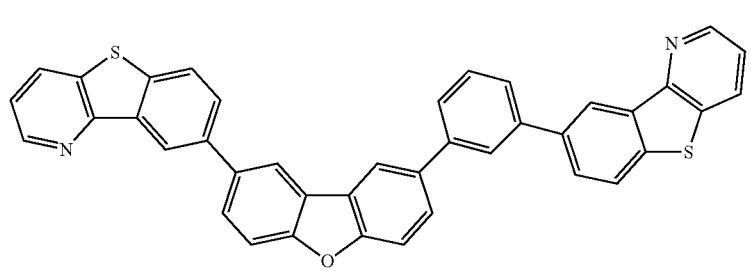
(110)
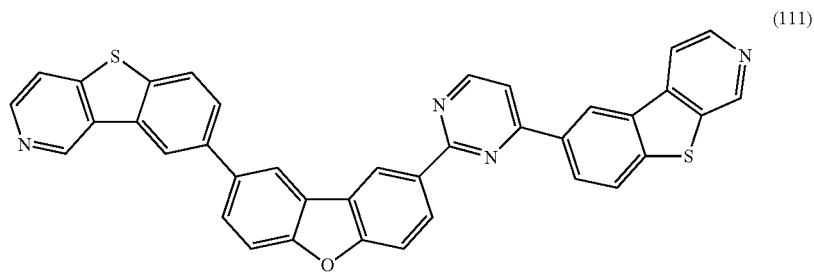
(111)

-continued
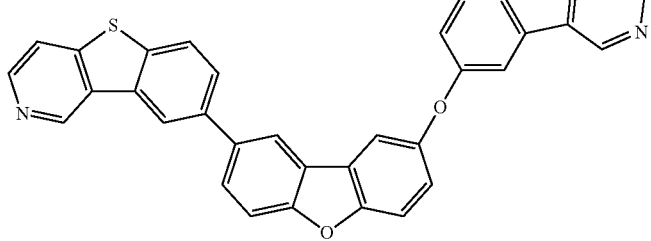
(112)
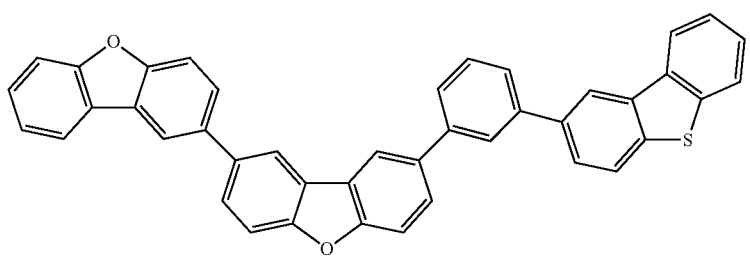
(113)
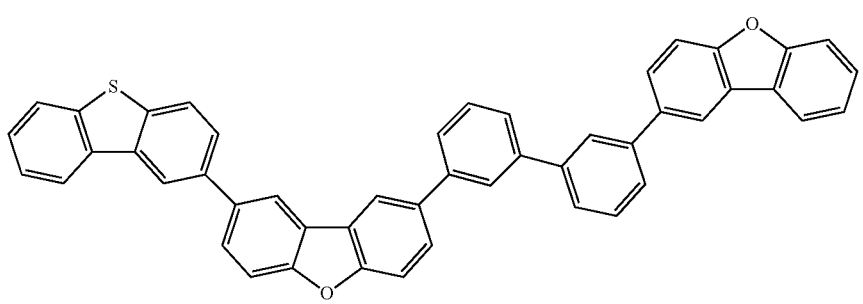
(114)
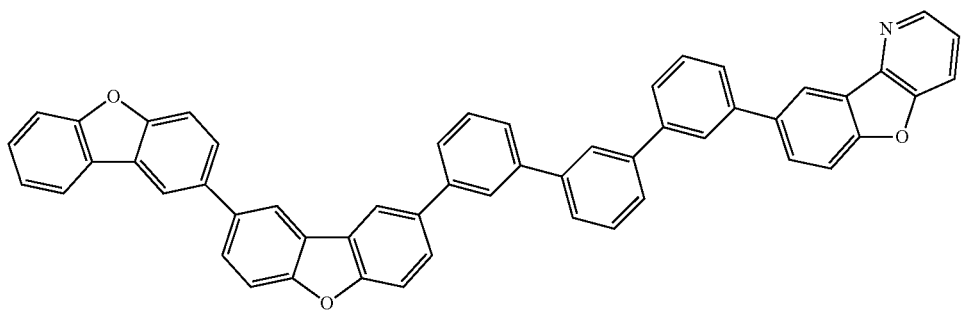
(115)
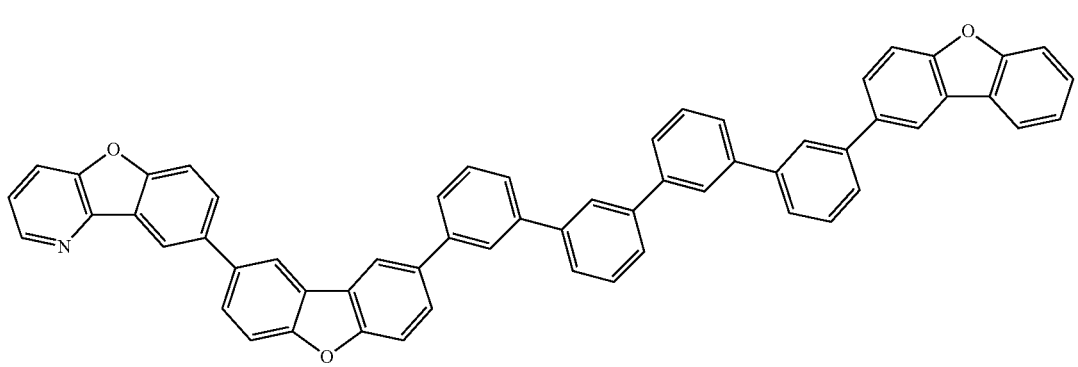
(116)

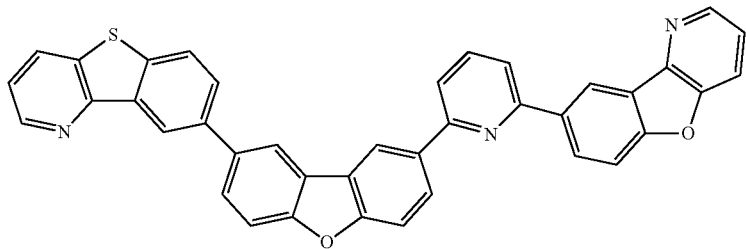
(117)
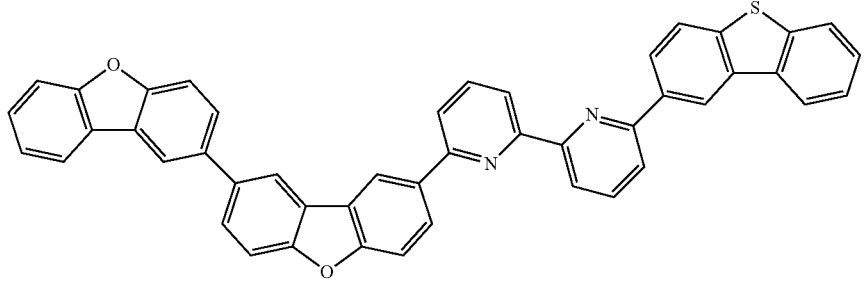
(118)
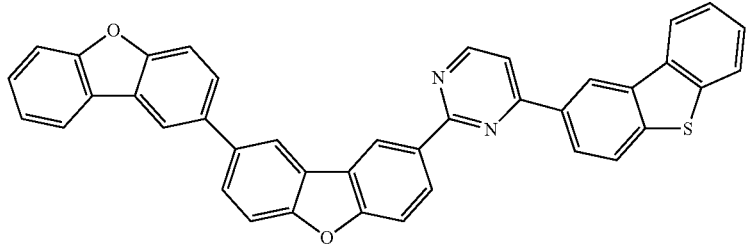
(119)
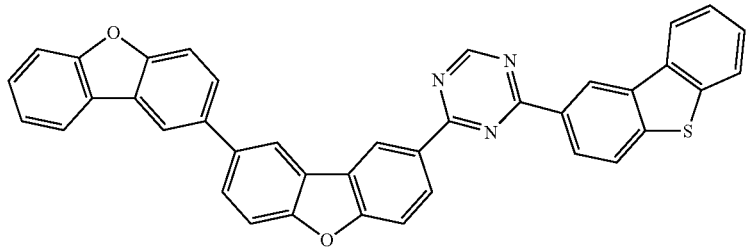
(120)
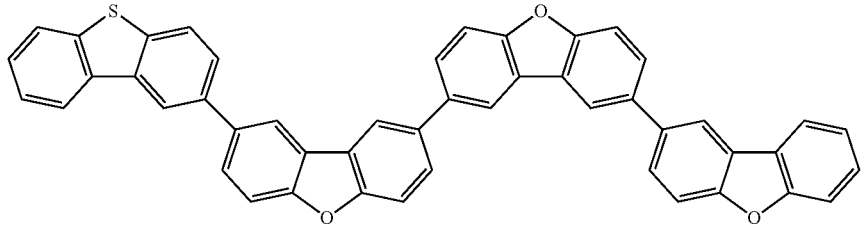
(121)
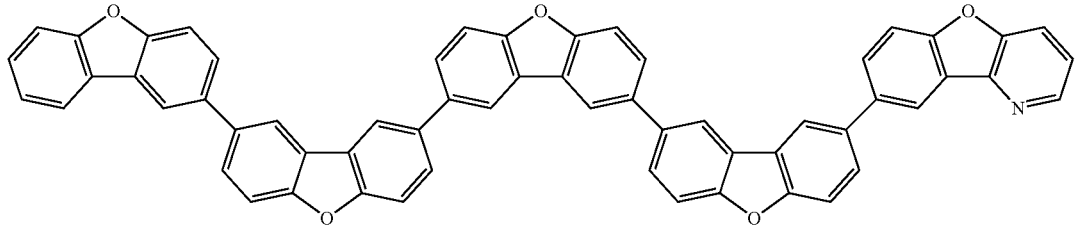
(122)

-continued
(123)
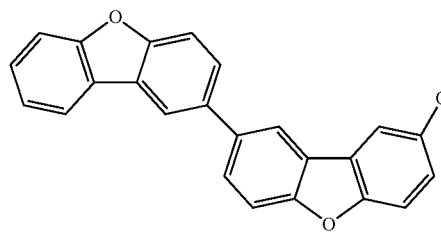
(124)
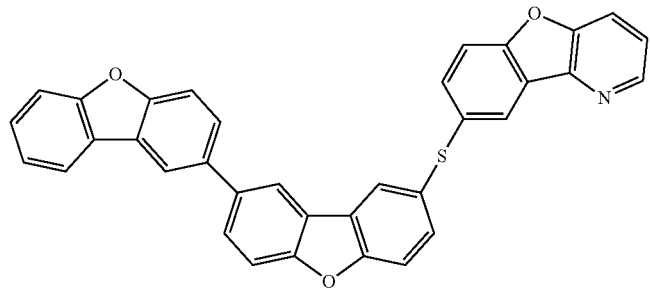
(125)
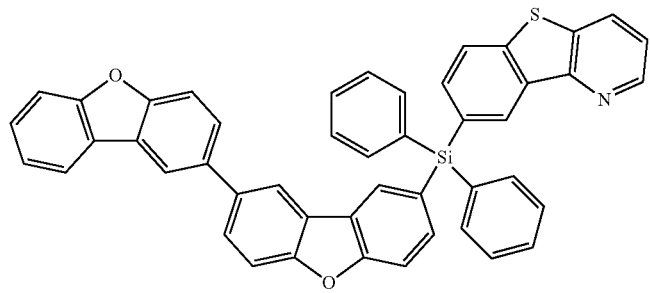
(126)
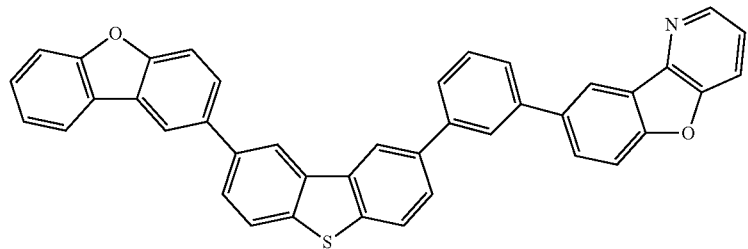
(127)
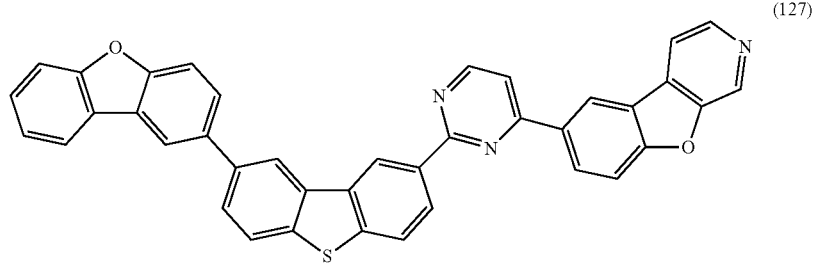

-continued
(128)
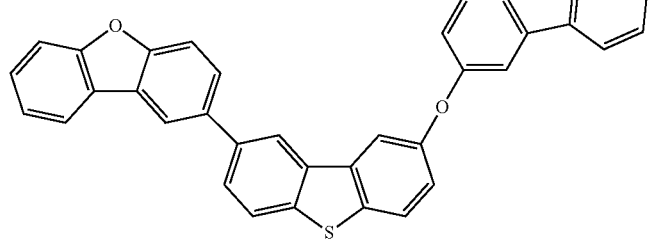
(129)
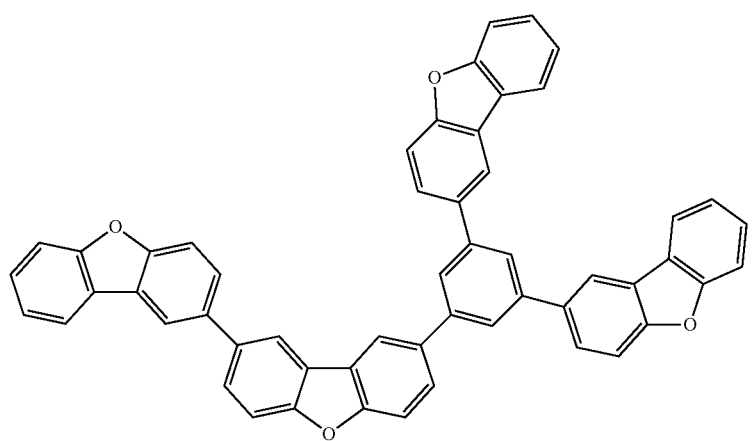
(130)
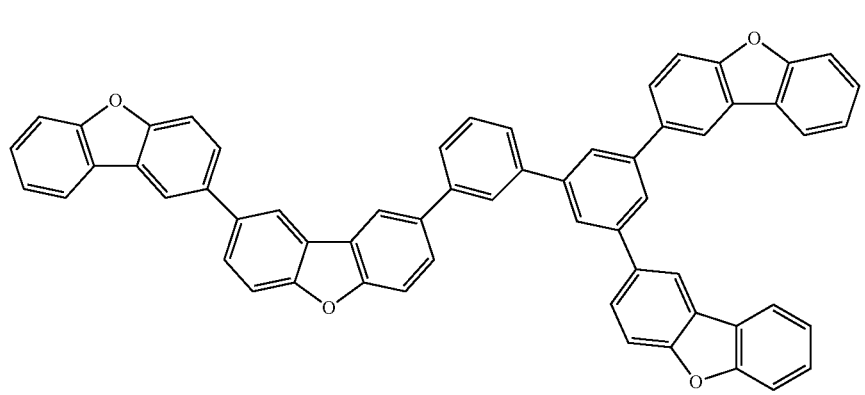
(131)
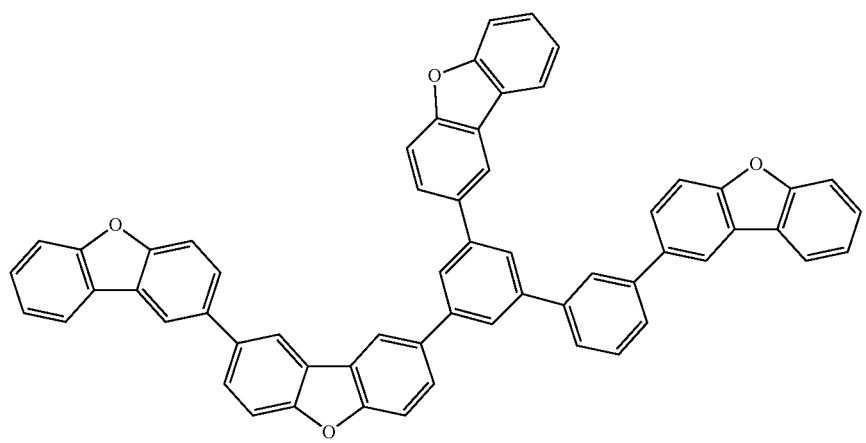

(132)
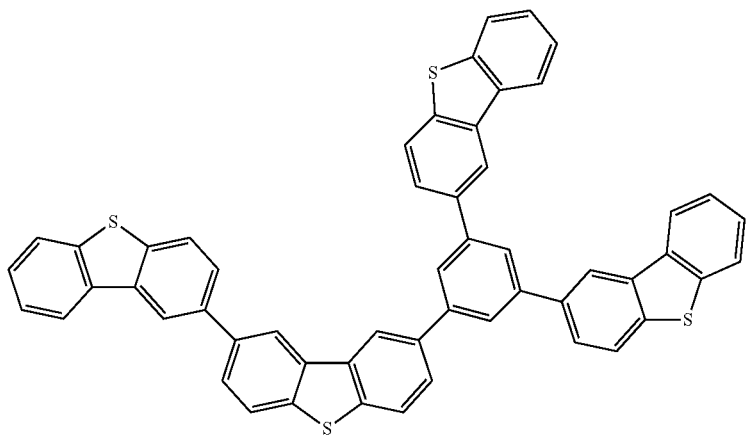
(133)
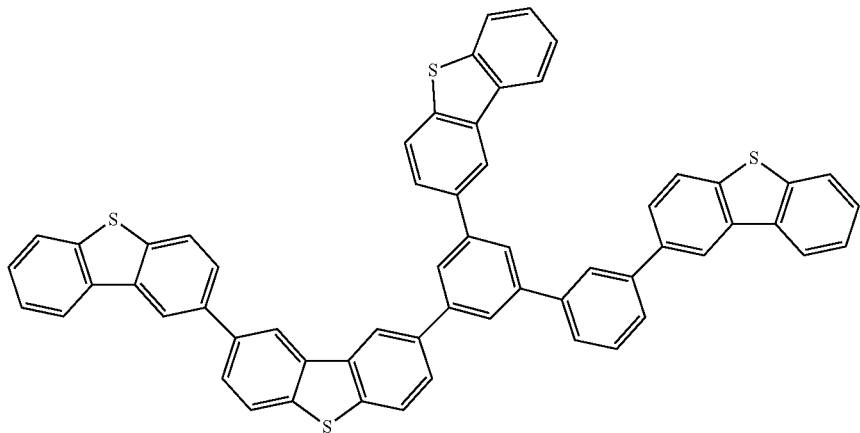
(134)
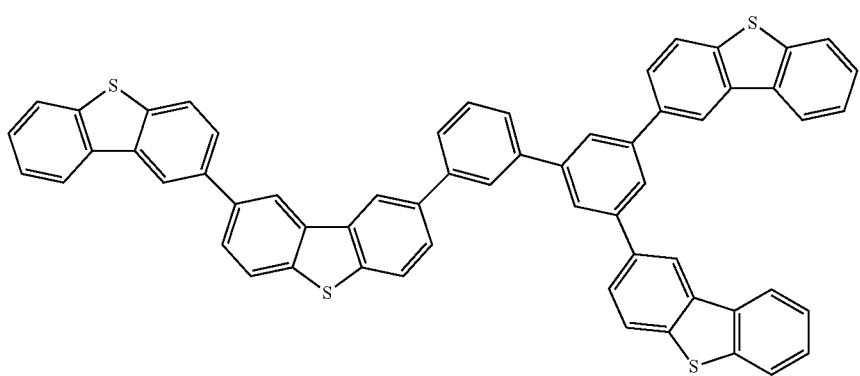

(135)
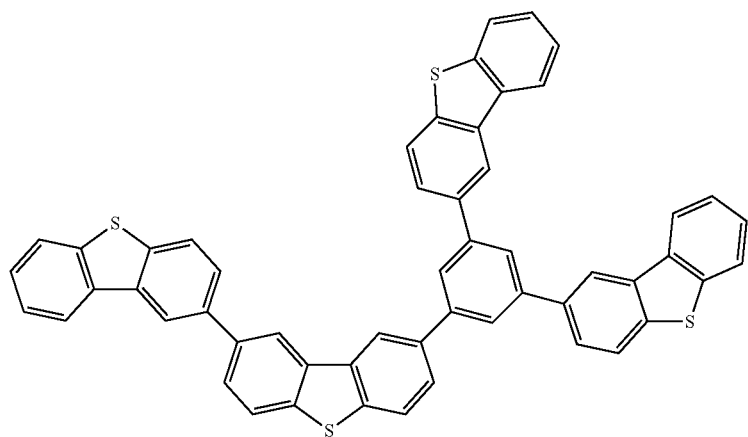
(136)
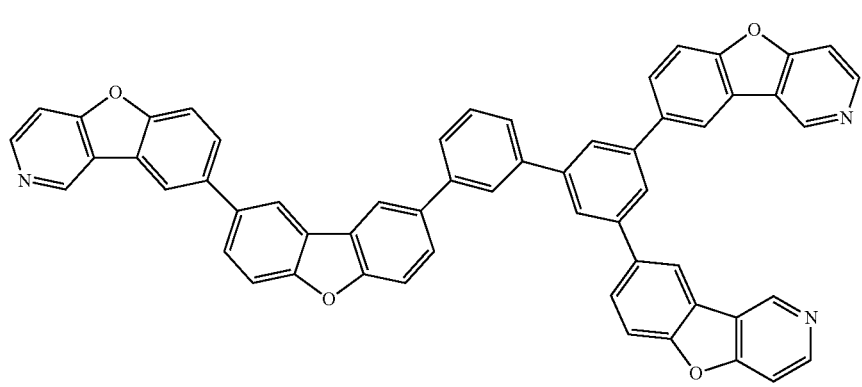
(137)
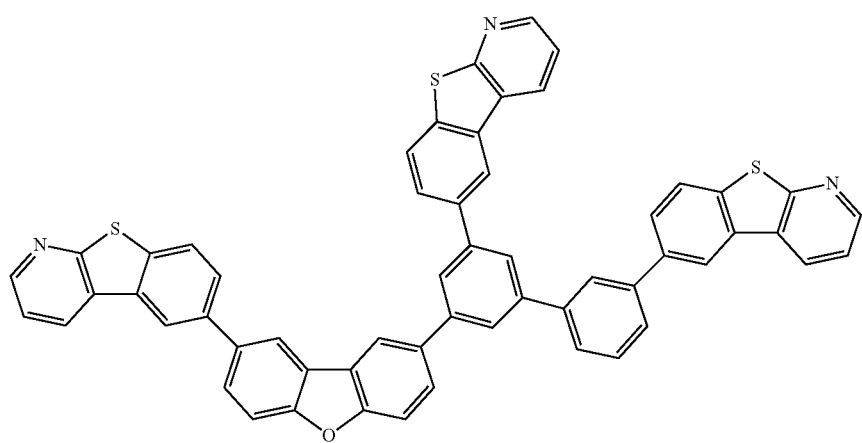

(138)
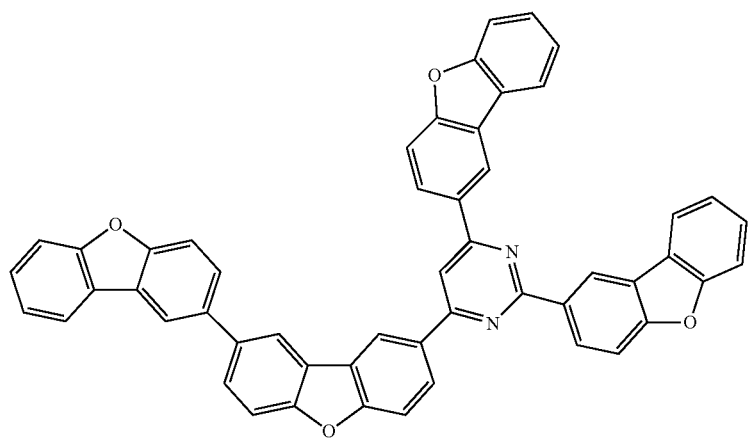
(139)
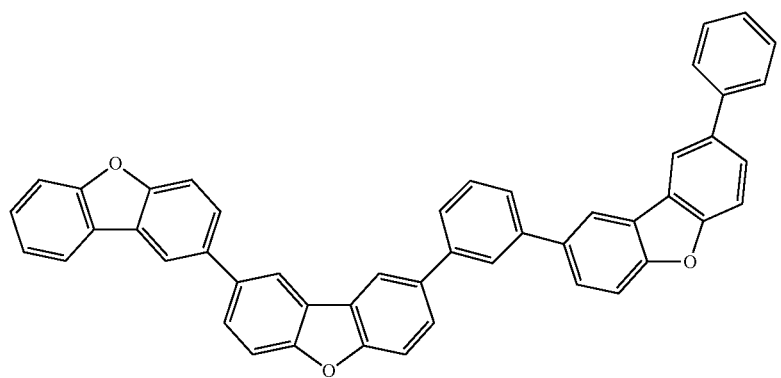
(140)
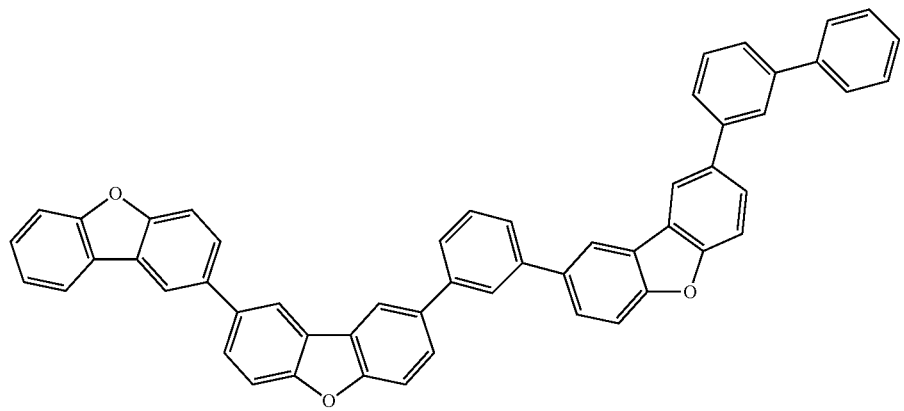
(141)
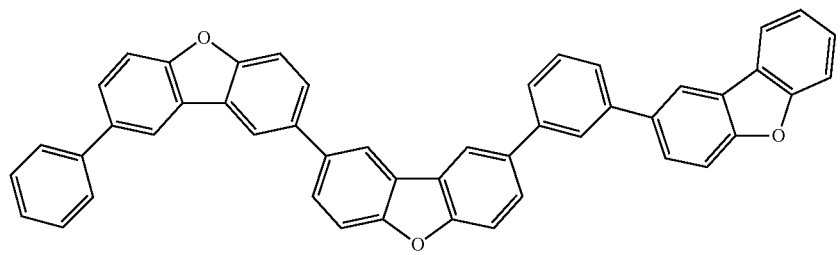

(142)
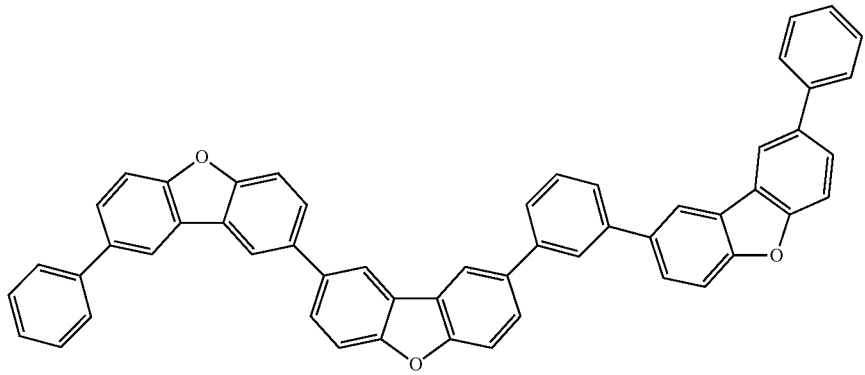
(143)
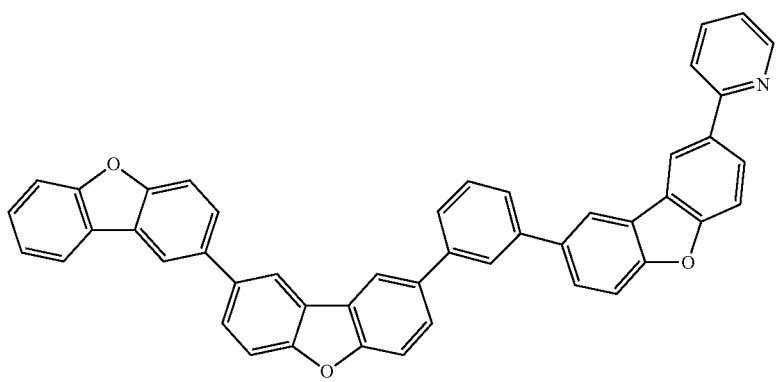
(144)
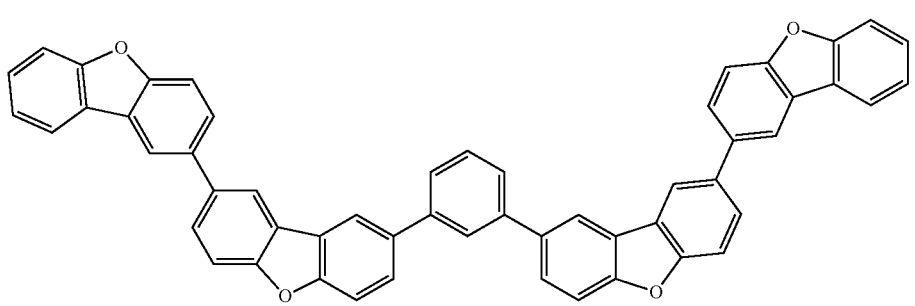
(145)
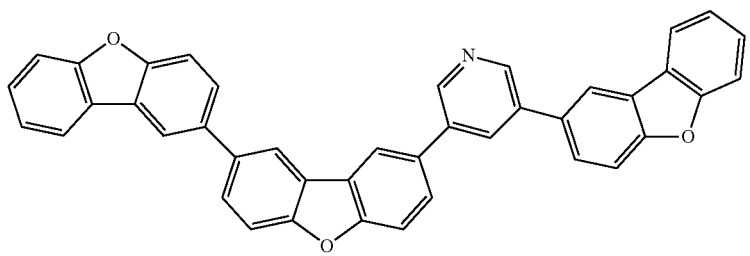

(146)
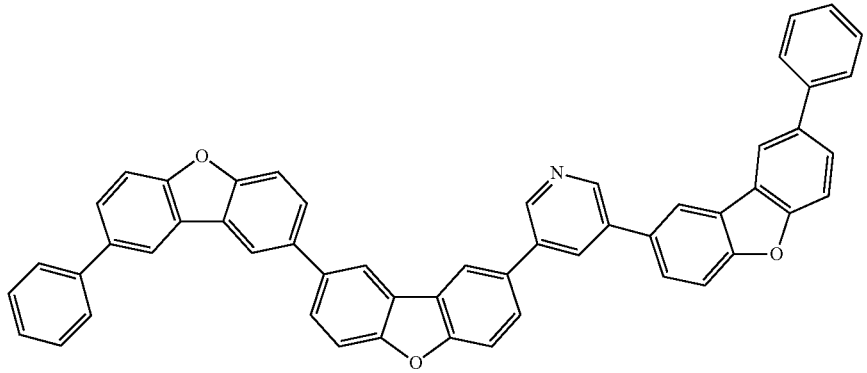
(147)
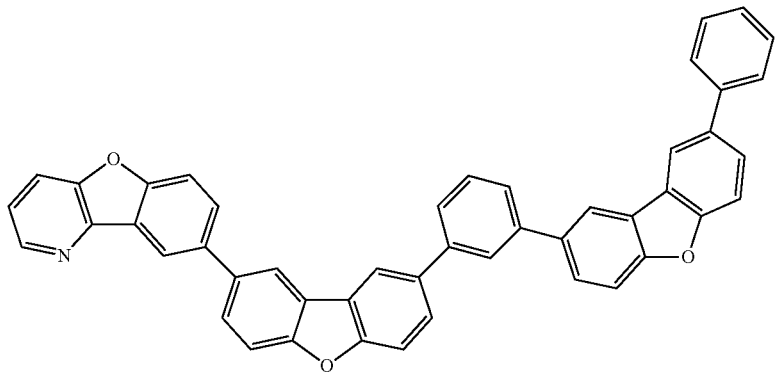
(148)
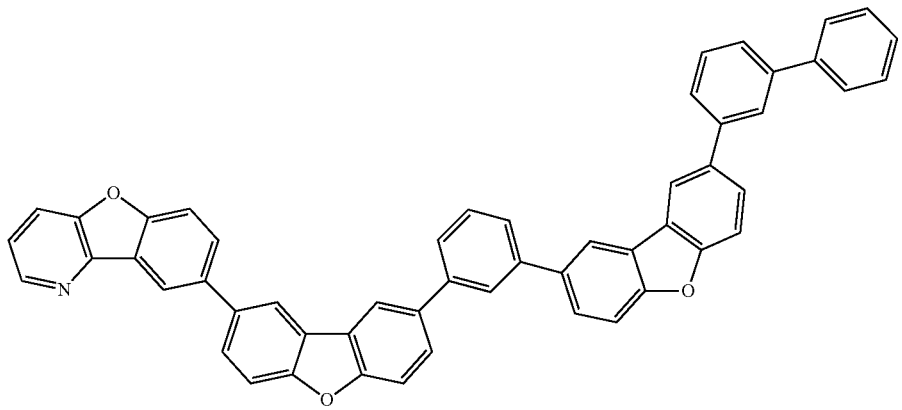
(149)
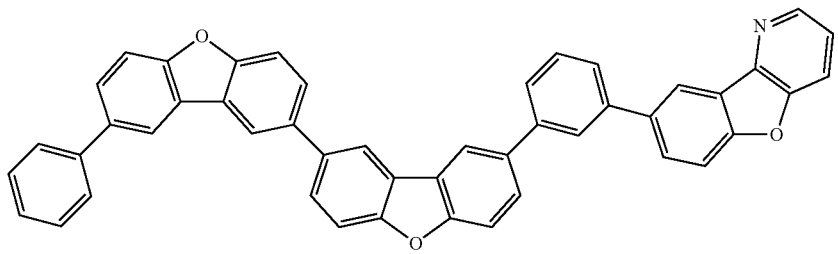

-continued
(150)
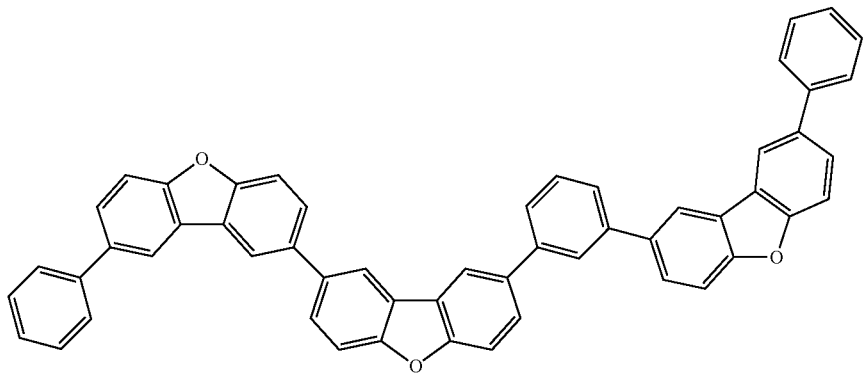
(151)
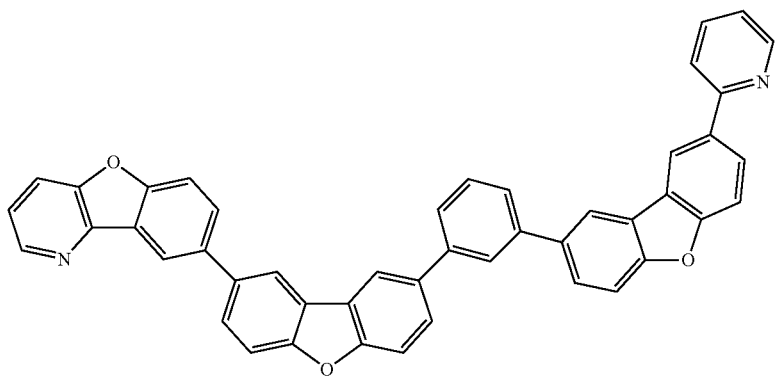
(152)
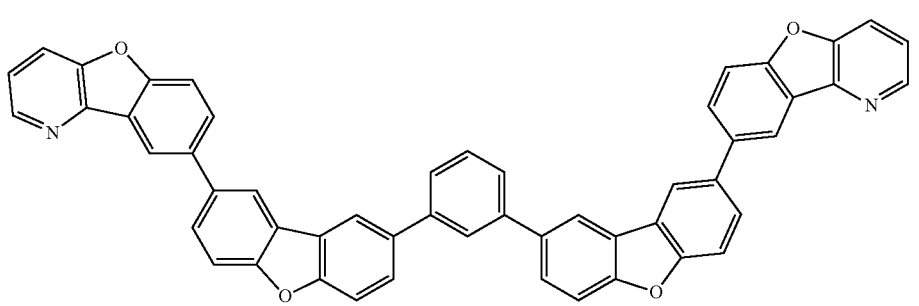
(153)
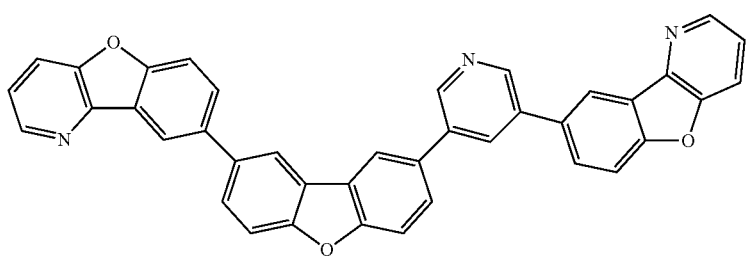

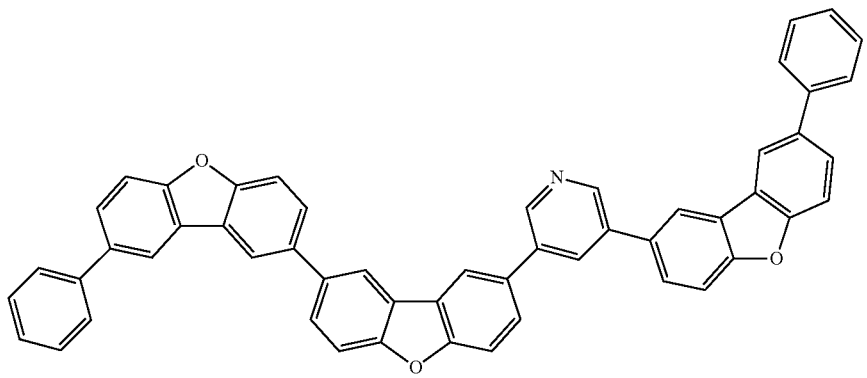

(154)

The material for an organic EL device of the invention is characterized in that it comprises the above-mentioned compound of the invention.

The material for an organic EL device of the invention is useful as the material for a phosphorescent organic EL device, and it can be used for all colors including blue, green and red. It is particularly useful as the material for blue emission.

The material for an organic EL device of the invention is useful as an emitting layer material, an electron-transporting material, a hole-transporting material, a hole-blocking material or the like.

By using the material for an organic EL device of the invention, an organic EL device which can be driven at a low voltage and has a long life can be obtained.

(Organic EL Device of the Invention)

The organic EL device of the invention is characterized in that it comprises a cathode and an anode, one or more organic thin film layers including an emitting layer between the cathode and the anode, and at least one layer of the organic thin film layers comprises the material for an organic EL device of the invention or the compound of the invention (hereinafter often merely referred to as the "organic EL device material").

By providing the organic thin film layers including the material for an organic EL device of the invention, it is possible to obtain an organic EL device which can be driven at a low voltage and has a long life.

In the organic EL device of the invention, it is preferred that the emitting layer contain the material for an organic EL device of the invention. It is more preferred that the material for an organic EL device of the invention be contained in the emitting layer as a host material. Due to the presence of the material for an organic EL device of the invention having a high energy which does not impair the luminous efficiency of a phosphorescent complex, the device has a high efficiency. Specifically, in order to obtain blue emission without impairing the efficiency, it is preferred that the triplet energy of the host material used in the emitting layer be 2.9 eV or more.

In the organic EL device of the invention, it is preferred that a hole-blocking layer and an electron-transporting layer be provided in this sequence between the emitting layer and the cathode, and that the hole-blocking layer between the emitting layer and the electron-transporting layer comprise the material for an organic EL device of the invention.

Due to the presence of the material for an organic EL device of the invention in the hole-blocking layer, it is possible to improve the injection and transportation of electrons into the emitting layer, whereby the effect of reducing the driving voltage of the device can be obtained. Further, as mentioned above, since the material of an organic EL device of the invention has a high energy that does not impair the luminous efficiency of a phosphorescent complex, whereby energy transfer from the emitting layer is suppressed, leading to an increase in efficiency of the device. Specifically, the triplet energy of the material used for the hole-blocking layer is preferably equivalent to the triplet energy of the host material mentioned above.

It is preferable that the emitting layer comprise a phosphorescent emitting material, and the phosphorescent emitting material is preferably a compound that has a metal selected from iridium (Ir), osmium (Os), and platinum (Pt). It is more preferred that the compound containing the metal be an ortho-methalated metal complex. Due to the presence of the phosphorescent emitting material in the emitting layer, effects that the luminous efficiency is significantly increased as compared with that of conventional fluorescent material can be obtained.

In the organic EL device of the invention, it is preferred that a reducing dopant be contained in the interfacial region between the cathode and the organic thin film layers. Specific examples of the reducing dopant will be given later. Due to the presence of a reducing dopant in the interfacial region, the organic EL device can have an excellent luminous efficiency and a long life.

In the organic EL device of the invention, it is preferred that an electron-injecting layer be present between the emitting layer and the cathode and that the electron-injecting layer comprise a nitrogen-containing heterocyclic derivative. Specific examples of the nitrogen-containing heterocyclic groups will be mentioned later. Due to the presence of a nitrogen-containing heterocyclic derivative in the electron-injecting layer, injection of electrons to adjacent layers is facilitated, thereby leading to a lowering in driving voltage of the device.

Next, a more detailed explanation will be given on the organic EL device of the invention.

In the organic EL device of the invention, between the cathode and the anode, one or more organic thin film layers including the emitting layer are present, and the emitting layer contains a phosphorescent emitting material. Further, at least one of these organic thin film layers comprises the material for an organic EL device of the invention.

As the configuration of a stacked type organic EL device, a multilayer structure obtained by stacking anode/hole-transporting region (hole-injecting layer and/or hole-transporting layer)/emitting layer/cathode, anode/emitting layer/electron-transporting region (blocking layer and/or electron-transporting layer and/or electron-injecting layer)/cathode, anode/hole-transporting region/emitting layer/electron-transporting region/cathode or the like can be given.

As for the configuration of the organic EL device, it may be a tandem device structure having at least two organic layer units including the emitting layer. As for the structure of the organic layer unit, hole-transporting region/emitting layer, emitting layer/electron-transporting region, hole-transporting region/emitting layer/electron-transporting region can be given.

It is possible to allow an intermediate layer (also referred to as an intermediate conductive layer, a carrier generating layer and a CGL) be intervened between the two emitting layers. An electron-transporting region can be provided according to each unit. In a tandem device structure, at least one light-emitting layer is a phosphorescent light-emitting layer. Specific examples of stacking order of a tandem device structure include anode/phosphorescent emitting layer/intermediate layer/phosphorescent emitting layer/electron-transporting region (preferably contains blocking layer)/cathode, anode/phosphorescent emitting layer/electron-transporting region (preferably contains a blocking layer)/intermediate layer/phosphorescent emitting layer/cathode, anode/fluorescent emitting layer/intermediate layer/phosphorescent emitting layer/electron-transporting region (preferably contains a blocking layer)/cathode, anode/phosphorescent emitting layer/electron-transporting region (preferably contains a blocking layer)/intermediate layer/fluorescent emitting layer/cathode, anode/phosphorescent emitting layer/electron-transporting region (preferably contains a blocking layer)/intermediate layer/phosphorescent emitting layer/electron-transporting region (preferably contains blocking layer)/cathode.

In the invention, the "hole-injecting/transporting layer" is included in the embodiment of the hole-transporting layer. Further, the emitting layer may be a stacked body of a plurality of emitting layers.

As mentioned above, in the organic EL device of the invention, the hole-transporting region may be provided between the cathode and the emitting layer, and the emitting layer or the hole-transporting region may contain the material for an organic EL device of the invention. Further, the electron-transporting region may be provided between the emitting layer and the cathode, and the electron-transporting region may contain the material for an organic EL device of the invention.

In the organic EL device of the invention, it is preferred that the material for an organic EL device represented by the formula (1) be contained in at least one or more layers of the emitting layer, the hole-transporting region (the hole-transporting layer, the hole-injecting layer), the electron-transporting region (the electron-transporting layer, the electron-injecting layer, the blocking layer). Particularly, it is more preferred that the material for an organic EL device be contained at least in the emitting layer or the electron-transporting region.

In the organic EL device of the invention, in the organic thin film layers containing the material for an organic EL device of the invention, the material is contained preferably in an amount of 50 vol % (v/v) or more, more preferably 70 vol % (v/v) or more, and further preferably 90 vol % (v/v) or more.

It is preferred that the electron-transporting region have a blocking layer in a part adjacent to the emitting layer. As mentioned later, the blocking layer has a function of preventing diffusion of triplet excitons generated in the emitting layer to the electron-transporting region, thereby to confine the triplet excitons within the emitting layer to suppress energy deactivation of triplet excitons on molecules other than the emission dopant of triplet excitons in the electron-transporting region.

An explanation will be given for easy understanding of the invention. It is supposed that, by using the material for an organic EL device in the blocking layer of the electron-transporting region, electrons can be injected efficiently to the emitting layer, and energy deactivation of triplet excitons in the electron-transporting region can be prevented. That is, it is supposed that, by using the material for an organic EL device of the invention in the blocking layer, the re-combination region of electrons and holes can be controlled easily. Further, it is also supposed that, since the material for an organic EL device of the invention has high electric and chemical stability to hole injection and hole transportation, if the material for an organic EL device of the invention is used as the blocking layer, the blocking layer can be prevented from being electrically and chemically deteriorated, whereby an organic EL device having excellent durability can be obtained.

It is supposed that, when the material for an organic EL device is used as the blocking layer, when the triplet energy of the phosphorescent dopant in the emitting layer is taken as $E^T_d$, and the triplet energy of the compound to be used as the blocking layer is taken as $E^T_{TB}$, if the magnitude of energy is $E^T_d < E^T_{TB}$, in the relationship of energy, the triplet excitons of the phosphorescent dopant are confined (that is, they cannot be moved to other molecules), the energy deactivation pathway other than emission on the dopant becomes impossible, whereby highly efficient emission can be realized. However, it is also supposed that, even if the relationship $E^T_d < E^T_{TB}$ is established, if the difference in energy $\Delta E^T = E^T_d - E^T_{TB}$ is small, at around room temperature under which the device is actually driven, the triplet excitons can be endothermically get over the energy difference by thermal energy of surroundings and transfer to another molecule. In particular, the life of excitons is longer in the case of phosphorescent emission as compared with fluorescent emission, effects of endothermic movement processes are emerged relatively easily. Therefore, use of the material of an organic EL device of the invention in the blocking layer is supposed to be effective in order to increase the efficiency of a phosphorescent device. A larger energy difference $\Delta E^T$ is preferable relative to thermal energy at room temperature. $\Delta E^T$ is further preferably 0.1 eV or more, with 0.2 eV or more being particularly preferable.

In the invention, the triplet energy is measured as follows. A sample is dissolved in an EPA solvent (diethylether:isopentane:ethanol=5:5:2 (volume ratio)) in a concentration of 10 μmol/L, thereby to allow the resulting solution to be used as a sample for measuring phosphorescence emission. This sample for measuring phosphorescence emission is placed in a quartz cell, and then irradiated with excited light at a temperature of 77K. The phosphorescent spectrum of radiated phosphorescent light is measured. Based on this spectrum, a value is obtained by a conversion formula $E^T$ (eV)=1239.85$\lambda_{edge}$. The "$_{edge}$" means, when the phosphorescent intensity and the wavelength are taken at the vertical axis and the horizontal axis respectively to express a phosphorescent spectrum and a tangential line is drawn against the rise on the shorter wavelength side of the phosphorescent spectrum, a wavelength value (unit: nm) of the intersection of the tangential line and the horizontal axis.

As the host material of the emitting layer, one satisfying the relationship $A_b-A_h \leq 0.1$ eV is preferable. Here, $A_b$ means the affinity of a material for the blocking layer and the $A_h$ means the affinity of a host material of the emitting layer.

Here, in the invention, the affinity Af (electron affinity) means energy which is emitted or absorbed when one electron is given to the molecule of the material. The affinity is defined as positive in the case of emission and defined as negative in the case of absorption. Affinity Af is defined as follows from the ionization potential Ip and the optical energy gap Eg (S).

$$Af=Ip-Eg(S)$$

Here, the ionization potential Ip means energy required to remove electrons from the compound of each material for ioniziation. In the invention, it is a positive value measured by means of a photoelectron spectrometer (AC-3, manufactured by RIKEN Co., Ltd.) in the atmosphere. The optical energy gap Eg (S) means a difference between the conduction level and the valence electron level. In the invention, the optical energy gap means a positive value obtained by converting the wavelength value at the intersection of the tangent line of the longer wavelength side of a UV-visible absorption spectrum of a dichloromethane diluted solution of each material and the base line (no absorption) to energy.

FIG. 1 shows a schematic configuration of one example of the organic EL device in the embodiment of the invention.

An organic EL device 1 comprises a transparent substrate 2, an anode 3, a cathode 4, and organic thin film layers 10 being provided between the anode 3 and the cathode 4.

The organic thin film layer 10 has a phosphorescent emitting layer 5 containing a phosphorescent host as the host material and a phosphorescent dopant as the phosphorescent material. Between the phosphorescent emitting layer 5 and the anode 3, a hole-injecting/transporting layer 6 or the like; between the phosphorescent emitting layer 5 and the cathode 4, an electron-injecting/transporting layer 7 or the like; may be provided.

Further, an electron-blocking layer may be provided on the anode 3 side of the phosphorescent emitting layer 5, and a hole-blocking layer may be provided on the cathode 4 side of the phosphorescent emitting layer 5.

Due to such a configuration, electrons and holes are confined in the phosphorescent emitting layer 5, whereby the possibility of generation of excitons in the phosphorescent emitting layer 5 can be increased.

In the specification of the present application, as for the terms "fluorescent host" and "phosphorescent host", when combined with a fluorescent dopant, the host is referred to as a fluorescent host, and when combined with a phosphorescent dopant, the host is referred to as a phosphorescent host. They are not unambiguously distinguished restrictively into a fluorescent host and a phosphorescent host only from the molecular structure.

In other words, in the specification, the fluorescent host means a material constituting a fluorescent emitting layer containing a fluorescent dopant, and does not mean one which can be used only as a host for a fluorescent emitting material.

Similarly, a phosphorescent host means a material constituting a phosphorescent emitting layer containing a phosphorescent dopant, and does not mean one which can be used only as a host for a phosphorescent emitting material.

In the specification, the "hole-injecting/transporting layer" means "at least one of the hole-injecting layer and the hole-transporting layer", and the "electron-injecting/transporting layer" means "at least one of the electron-injecting layer and the electron-transporting layer".

(Transparent Substrate)

The organic EL device of the invention is normally fabricated on a transparent substrate. The transparent substrate as referred to herein means a substrate that supports an organic EL device, and a flat and smooth substrate having a transmittance of visible light of 400 nm to 700 nm of 50% or more is preferable.

Specifically, a glass sheet, a polymer sheet or the like can be given.

Examples of a material for forming the glass sheet include those using as a raw material soda lime glass, barium-strontium-containing glass, lead glass, aluminosilicate glass, borosilicate glass, barium borosilicate glass, quartz, and the like.

Examples of a material for forming the polymer sheet include those using as a raw material polycarbonate, acryl, polyethylene terephthalate, polyethersulfide, polysulfone, and the like.

(Anode and Cathode)

The anode of the organic EL device serves to inject holes to the hole-injecting layer, the hole-transporting layer or the emitting layer, and one having a work function of 4.5 eV or more is effective.

As the specific examples of the anode material, an indium tin oxide (ITO) alloy, tin oxide (NESA), indium zinc oxide, gold, silver, platinum, copper or the like can be given.

The anode can be formed by forming these electrode materials into a thin film by a method such as a deposition method and a sputtering method.

When outcoupling light from the emitting layer through the anode, it is preferable that the cathode have a light transmittance of more than 10%. The sheet resistance of the cathode is preferably several hundred Ω/square or less. The thickness of the anode is normally 10 nm to 1 μm, and preferably 10 to 200 nm, although it depends on the material.

The cathode serves to inject electrons to the electron-injecting layer, the electron-transporting layer or the emitting layer, and one having a small work function is preferable.

Although no specific restrictions are imposed on the cathode material, as specific examples thereof, indium, aluminum, magnesium, a magnesium/indium alloy, a magnesium/aluminum alloy, an aluminum-lithium alloy, an aluminum-scandium-lithium alloy, a magnesium-silver alloy or the like can be used.

As in the case of the anode, the cathode can be formed by forming materials into a thin film by a method such as a deposition method and a sputtering method. Also, an embodiment in which light is outcoupled through the cathode can also be used.

(Emitting Layer)

The emitting layer of the organic EL device has the following functions in combination.

(i) Injection function: function of allowing injection of holes from the anode or hole-injecting layer and injection of electrons from the cathode or electron-injecting layer upon application of an electric field (ii) Transporting function: function of moving injected carriers (electrons and holes) due to the force of an electric field (iii) Emitting function: function of providing a site for re-combining electrons and holes to cause emission Note that electrons and holes may be injected into the emitting layer with different degrees, or the transportation capabilities indicated by the mobility of holes and electrons may differ.

As the method for forming the emitting layer, a known method such as deposition, spin coating and the LB method can be applied.

It is preferable that the emitting layer be a molecular deposition film.

The molecular deposition film as referred to herein means a thin film which is formed by deposition of a raw material compound in the vapor-phase state or a film which is formed by solidification of a raw material compound in the solution state or in the liquid-phase state and is distinguished from a thin film (molecular accumulation film) formed using the LB method by the difference in aggregation structure or higher order structure or the difference in function due to the difference in structure.

The emitting layer may also be formed by dissolving a binder such as a resin and a material compound in a solvent to obtain a solution, and forming a thin film from the solution by spin coating or the like.

In the organic EL device of the invention, between the cathode and the anode, one or more organic thin film layers including the emitting layer are provided, and at least one of the organic thin film layers comprises the material for an organic EL device of the invention. If plural emitting layers are present, it is preferred that at least one of the emitting layers contain the material for an organic EL device of the invention and a phosphorescent material.

(Phosphorescent Material)

The organic EL device of the invention comprises an organic metal complex as a phosphorescent material. It is preferred that the organic metal complex contain a metal atom selected from Ir, Pt, Os, Au, Cu, Be, Re and Ru and a ligand. In particular, it is preferred that the ligand have an ortho-metal bond.

In respect of capability of further improving the external quantum efficiency of the emitting device due to high phosphorescent quantum yield, a compound containing a metal atom selected from Ir, Os and Pt is preferable. A metal complex such as an iridium complex, an osmium complex and a platinum complex are further preferable, with an iridium complex and a platinum complex being more preferable. An ortho-metalated iridium complex is most preferable.

Specific examples of preferable organic metal complexes are shown below.

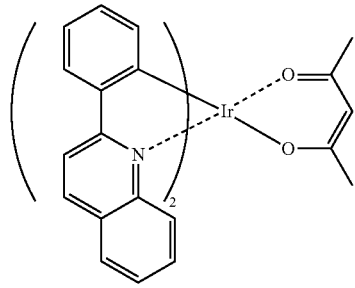

PQIr

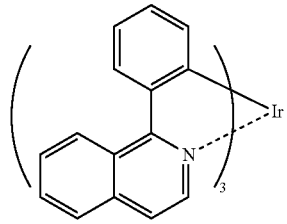

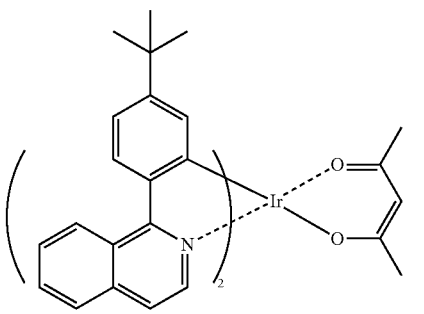

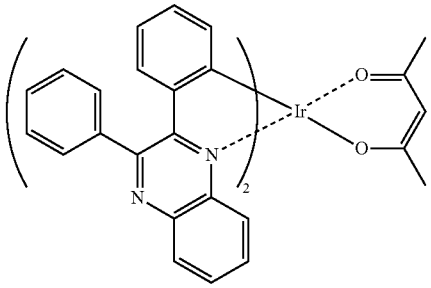

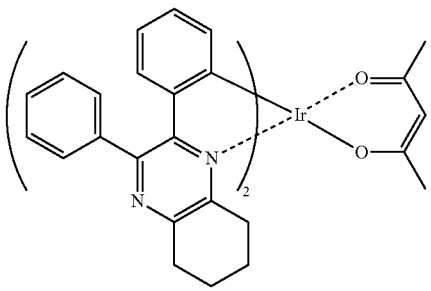

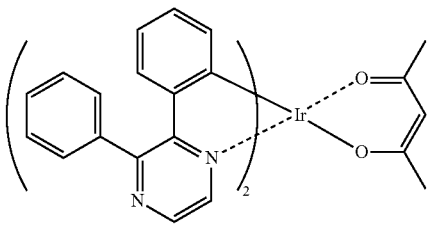

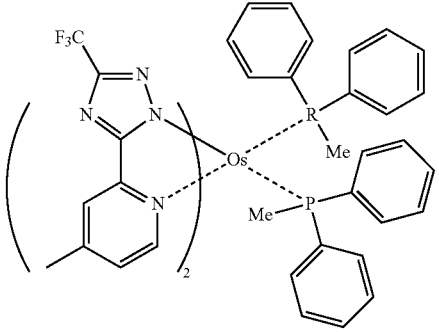

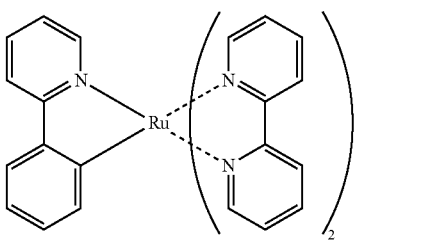

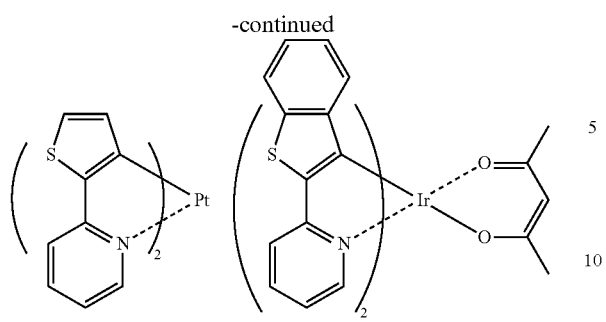
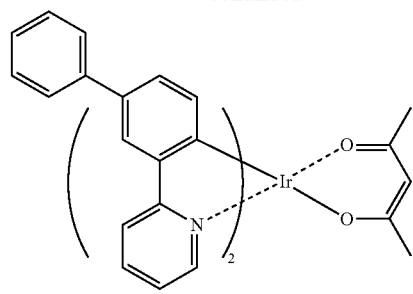
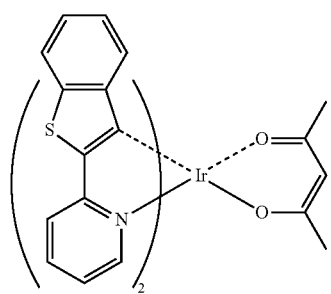
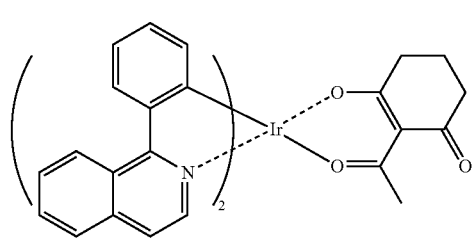
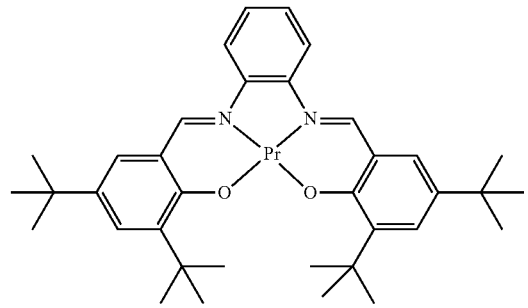
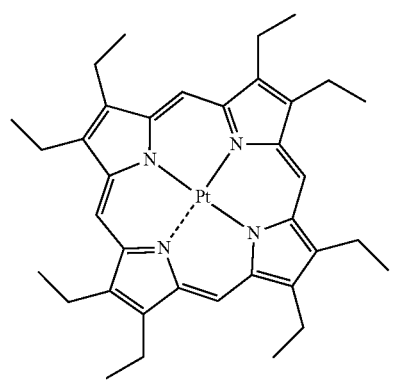
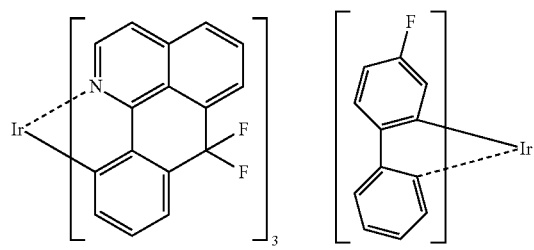
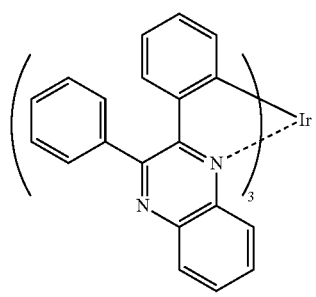
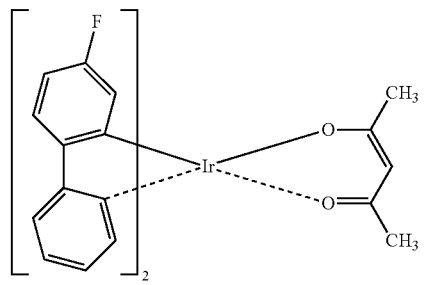
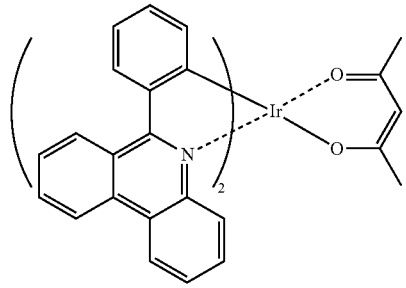
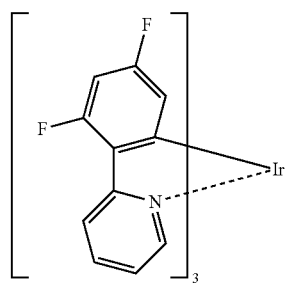

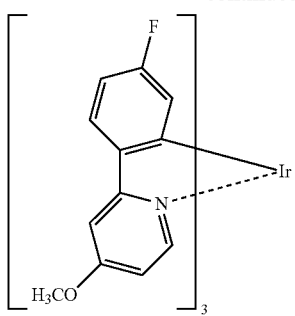
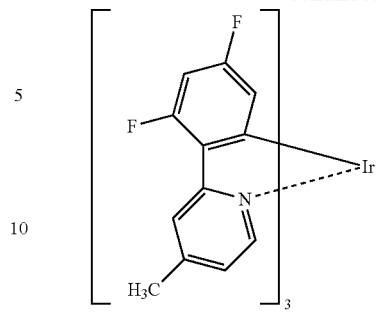
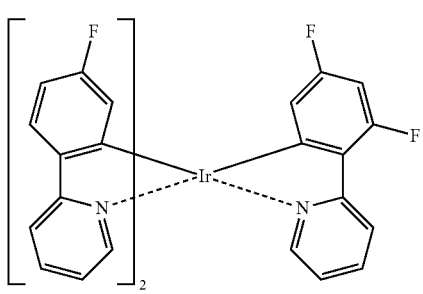
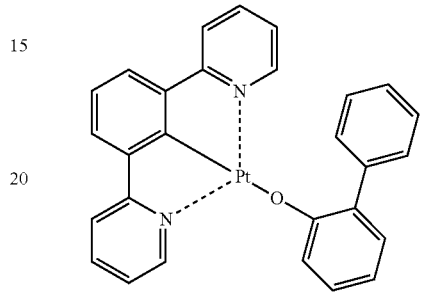
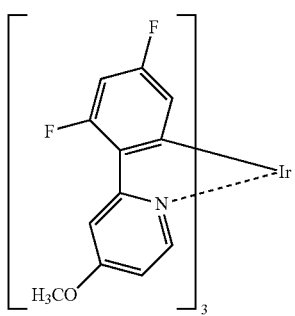
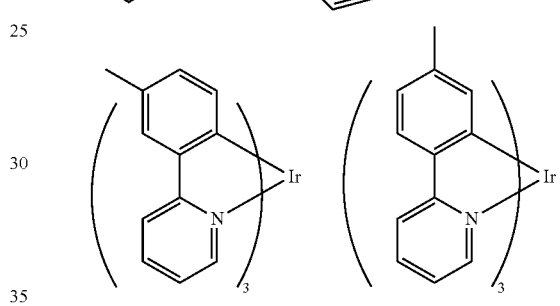
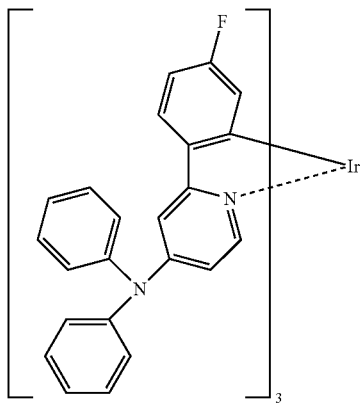
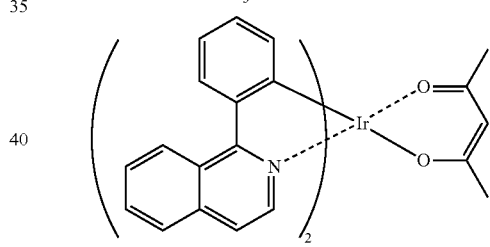
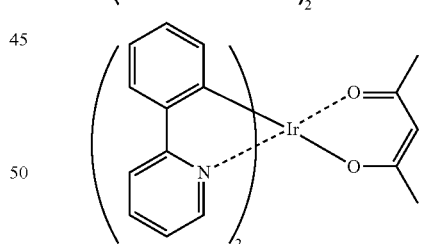
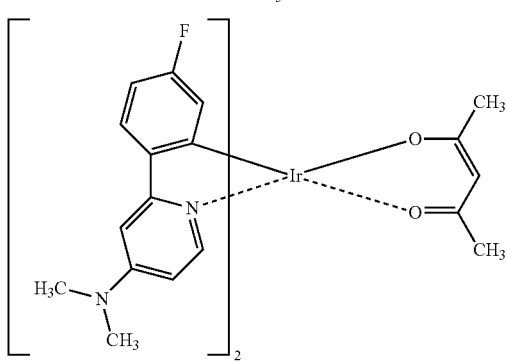
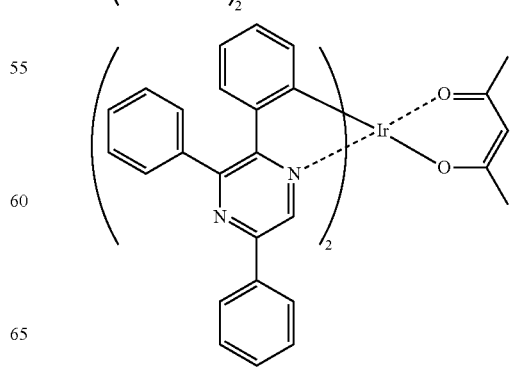

-continued
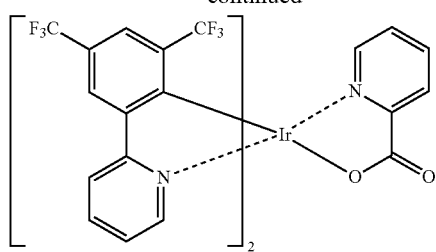
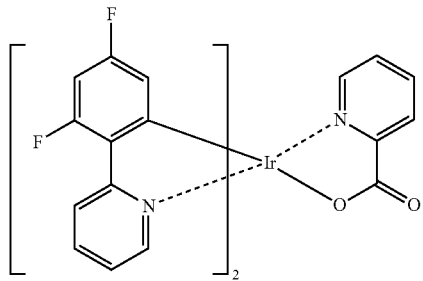
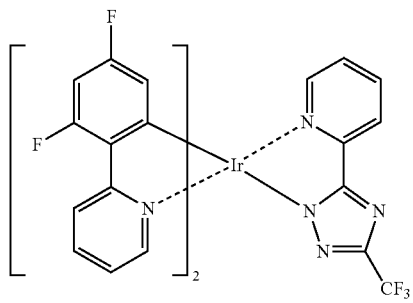
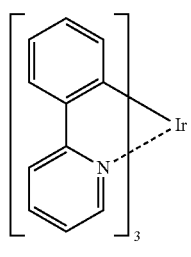
Ir (ppy)₃
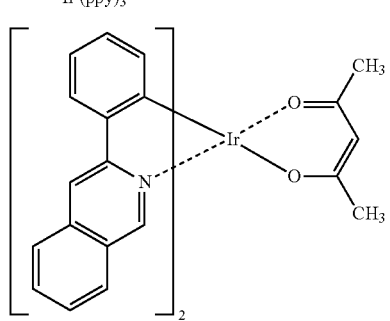
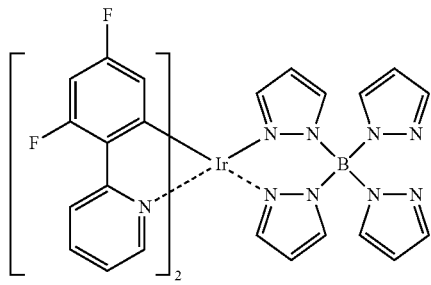
-continued
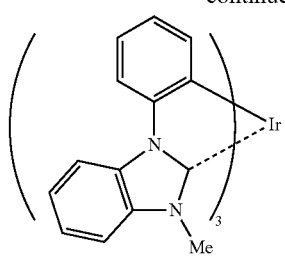
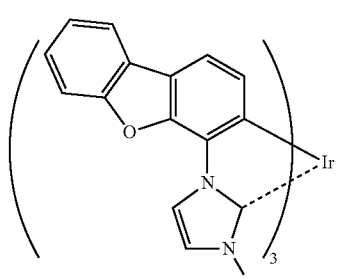
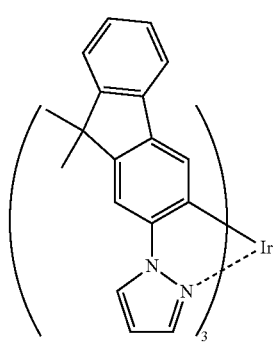
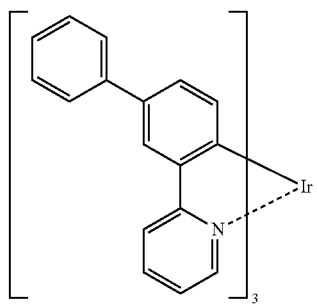
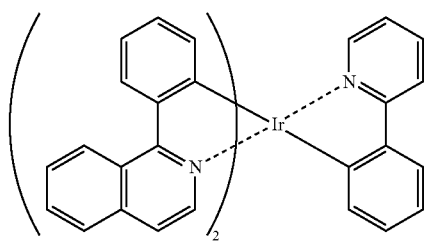
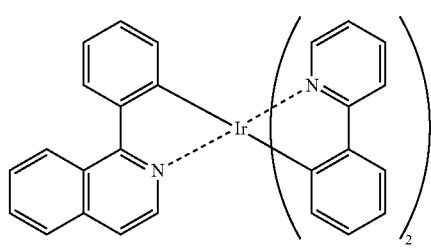

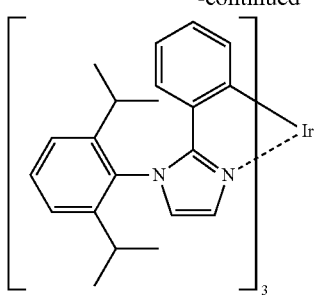
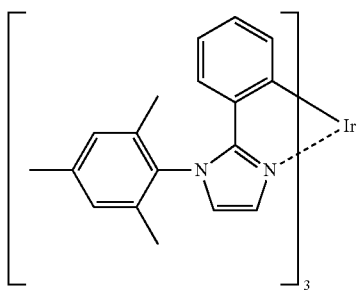
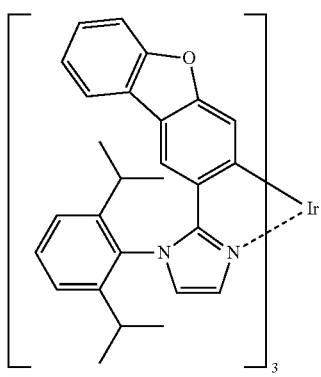
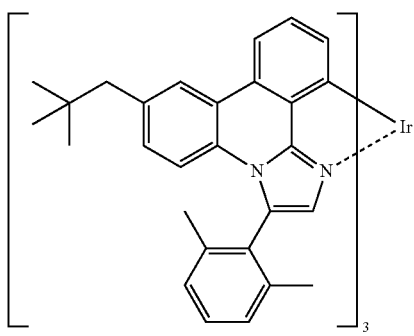
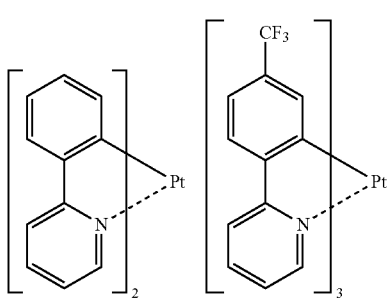
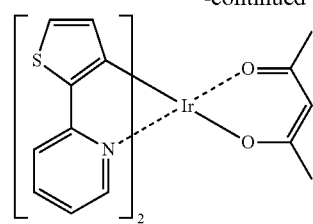
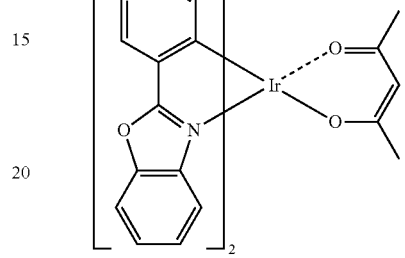
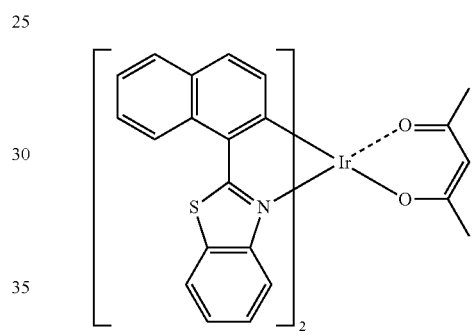
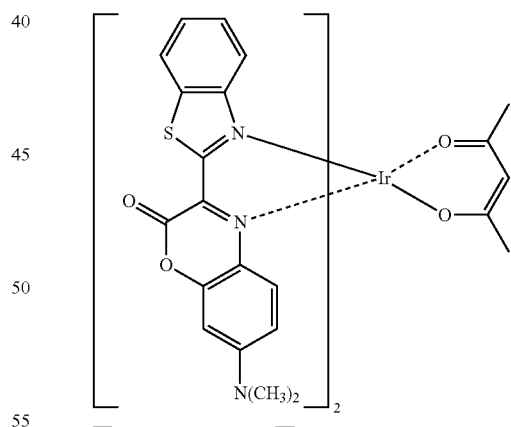
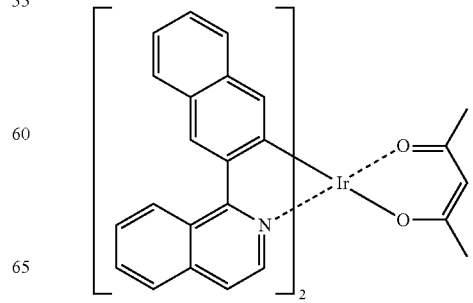

-continued

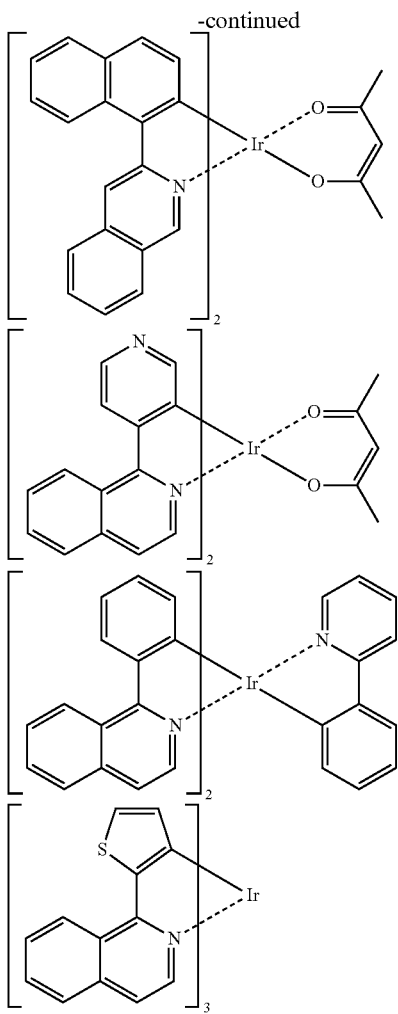

In the invention, it is preferred that at least one of the phosphorescent materials contained in the emitting layer have the maximum emission wavelength value of 450 nm or more and 750 nm or less. As a preferable example, the maximum wavelength value is 450 nm or more and 495 nm or less, 495 nm or more and 590 nm or less, and 590 nm or more and 750 nm or less.

By allowing a phosphorescent material (phosphorescent dopant) to be doped with a specific host material used in the invention to form the emitting layer, a highly efficient organic EL device can be realized.

(Electron Donor Dopant and Organic Metal Complex)

In the organic EL device of the invention, it is preferred that at least any of an dopant and an organic metal complex be contained in the interfacial region between the cathode and the organic thin film layer.

Due to such a configuration, the organic EL device can have an improved luminance and a prolonged life.

As the electron donor dopant, at least one selected from alkali metals, alkali metal compounds, alkaline earth metals, alkaline earth metal compounds, rare earth metals and rare earth metal compounds can be given.

As the organic metal complex, at least one selected from an organic metal complex containing an alkali metal, an organic metal complex containing an alkaline earth metal and an organic metal complex containing a rare earth metal or the like can be given.

As the alkali metal, lithium (Li) (work function: 2.93 eV), sodium (Na) (work function: 2.36 eV), potassium (K) (work function: 2.28 eV), rubidium (Rb) (work function: 2.16 eV), cesium (Cs) (work function: 1.95 eV) or the like can be given. One having a work function of 2.9 eV or less is particularly preferable. Of these, K, Rb and Cs are preferable, with Rb or Cs being further preferable. Most preferable is Cs.

As the alkaline earth metal, calcium (Ca) (work function: 2.9 eV), strontium (Sr) (work function: 2.0 eV or more and 2.5 eV or less), barium (Ba) (work function: 2.52 eV) or the like can be given. One having a work function of 2.9 eV or less is particularly preferable.

As the rare earth metal, scandium (Sc), yttrium (Y), cerium (Ce), terbium (Tb), ytterbium (Yb) or the like can be given. One having a work function of 2.9 eV or less is particularly preferable.

Of the above-mentioned metals, particularly preferable are metals having high reducing ability, and the addition of a relatively small amount thereof to an electron-injecting zone improves the luminance of the organic EL device and make the life thereof long.

As the alkali metal compound, alkali oxides such as lithium oxide ($Li_2O$), cesium oxide ($Cs_2O$), and potassium oxide ($K_2O$), alkali metal halides such as lithium fluoride (LiF), sodium fluoride (NaF), cesium fluoride (CsF), and potassium fluoride (KF), and the like can be given. Among these, lithium fluoride (LiF), lithium oxide ($Li_2O$) and sodium fluoride (NaF) are preferable.

Examples of the alkaline-earth metal compounds include barium oxide (BaO), strontium oxide (SrO), calcium oxide (CaO), barium strontium oxide ($Ba_xSr_{1-x}O$) (0<x<1) and barium calcium oxide ($Ba_xCa_{1-x}O$) (0<x<1) as mixtures thereof, and the like. Among these, BaO, SrO, and CaO are preferable.

Examples of the rare-earth metal compounds include ytterbium fluoride ($YbF_3$), scandium fluoride ($ScF_3$), scandium oxide ($ScO_3$), yttrium oxide ($Y_2O_3$), cerium oxide ($Ce_2O_3$), gadolinium fluoride ($GdF_3$), terbium fluoride ($TbF_3$), and the like. Among these, $YbF_3$, $ScF_3$, and $TbF_3$ are preferable.

The organic metal complex is not particularly limited as long as the organic metal complex includes at least one of an alkali metal ion, an alkaline-earth metal ion, and rare-earth metal ion as the metal ion. Examples of a preferable ligand include, but are not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfluoborane, bipyridyl, phenanthroline, phthalocyanine, porphyrin, cyclopentadiene, β-diketones, azomethines, derivatives thereof, and the like.

The electron donor dopant and the organic metal complex are preferably formed in the interfacial region in the shape of a layer or islands. It is preferable to deposit an organic material (i.e., an emitting material or an electron-injecting material that forms the interfacial region) while depositing at least one of the electron donor dopant and the organic metal complex by resistance heating deposition so that at least one of the electron donor dopant and the organic metal complex is dispersed in the organic material. The dispersion concentration (i.e., the molar ratio of the organic substance to the electron donor dopant and/or the organic metal complex) is normally 100:1 to 1:100, and preferably 5:1 to 1:5.

When forming at least one of the electron donor dopant and the organic metal complex in the shape of a layer, the emitting material or the electron-injecting material (i.e., the organic layer at the interface) is formed in the shape of a layer, and at least one of the electron donor dopant and the organic metal complex is deposited by resistance heating deposition to have a layer thickness of preferably 0.1 nm to 15 nm.

When forming at least one of the electron donor dopant and the organic metal complex in the shape of islands, the emitting material or the electron-injecting material (i.e., the organic layer at the interface) is formed in the shape of islands, and at least one of the electron donor dopant and the organic metal complex is deposited by resistance heating deposition to an island thickness of preferably 0.05 nm to 1 nm.

The molar ratio of the main component (emitting material or electron-injecting material) to at least one the electron donor dopant and the organic metal complex in the organic EL device according to the invention is preferably 5:1 to 1:5 (main component:electron donor component and/or organic metal complex) in terms of molar ratio, with 2:1 to 1:2 being further preferable.

(Electron-Injecting Layer and Electron-Transporting Layer)

The electron-injecting or the electron-transporting layer is a layer that assists injection of electrons into the emitting layer, and exhibits high electron mobility. The electron-injecting layer is provided to adjust the energy level. For example, it relaxes a sudden change in energy level.

In the organic EL device of the invention, the electron-injecting layer is provided between the emitting layer and the cathode. It is preferred that the electron-injecting layer contain a nitrogen-containing derivative as the main component. Here, the electron-injecting layer may be a layer that functions as an electron-transporting layer.

The expression "as the main component" means that the electron-injecting layer contains a nitrogen-containing derivative in an amount of 50 mass % or more.

As the electron-transporting material used in the electron-injecting layer, an aromatic heterocyclic compound having one or more hetero atoms within the molecule is preferably used. In particular, a nitrogen-containing heterocyclic derivative is preferable. As the nitrogen-containing heterocyclic derivative, an aromatic ring having a nitrogen-containing 6-membered ring skeleton or a nitrogen-containing 5-membered ring skeleton or a fused aromatic ring compound having a nitrogen-containing 6-membered ring skeleton or a nitrogen-containing 5-membered ring skeleton is preferable.

As the nitrogen-containing derivative, a nitrogen-containing metal chelate complex represented by the following formula (A) is preferable.

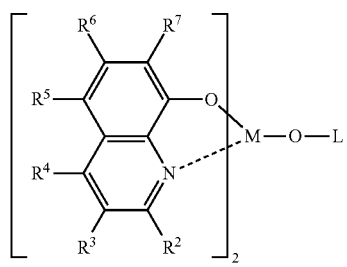

(A)

$R^2$ to $R^7$ in the formula (A) are independently a hydrogen atom, a halogen atom, an oxy group, an amino group, a hydrocarbon group having 1 to 40 carbon atoms, an alkoxy group, an aryloxy group, an alkoxycarbonyl group or an aromatic heterocyclic group. These atoms and groups may be substituted.

Examples of the halogen atom include fluorine, chlorine, bromine, and iodine. Further, as examples of the amino group that may be substituted, an alkylamino group, an arylamino group, an aralkylamino group can be given.

The alkoxycarbonyl group is represented by —COOY', and as examples of Y', those similar to the alkyl group can be given. The alkylamino group and the aralkylamino group are represented by —NQ$^1$Q$^2$. As specific examples of Q$^1$ and Q$^2$, those similar to the examples of the alkyl group and the aralkyl group can respectively be given. The same applies to the preferable examples.

The arylamino group is represented by —NAr$^1$Ar$^2$. As specific examples of Ar$^1$ and Ar$^2$, those similar to the examples in the non-fused aromatic hydrocarbon group and the fused aromatic hydrocarbon group can be given.

M is aluminum (Al), gallium (Ga) or indium (In), and In is preferable.

L in the above formula (A) is a group represented by the following formula (A') or (A").

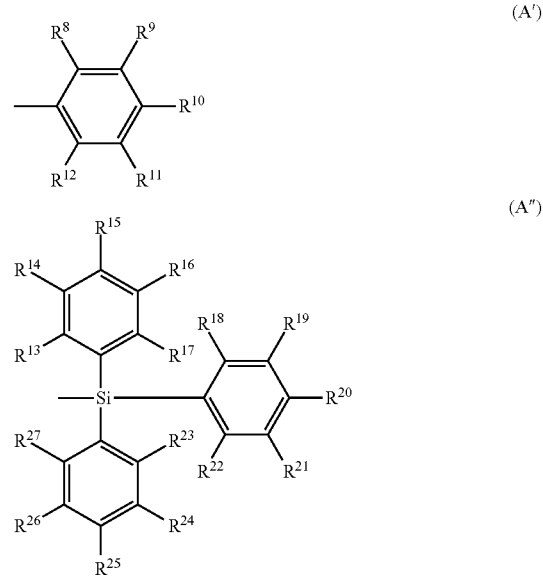

In the formula (A'), $R^8$ to $R^{12}$ are independently a hydrogen atom or a substituted or unsubstituted hydrocarbon group having 1 to 40 carbon atoms. The adjacent groups may form a ring-like structure. In the formula (A"), $R^{13}$ to $R^{27}$ are independently, a hydrogen atom or a substituted or unsubstituted hydrocarbon atom having 1 to 40 carbon atoms, and adjacent groups may form a ring-like structure.

As the hydrocarbon group having 1 to 40 carbon atoms represented by $R^8$ to $R^{12}$ and $R^{13}$ to $R^{27}$ in the formulas (A') and (A"), those similar to the specific examples of $R^2$ to $R^7$ in the formula (A) can be given.

As the divalent group when the adjacent groups of $R^8$ to $R^{12}$ and $R^{13}$ to $R^{27}$ form a ring-like structure, a tetramethylene group, a pentamethylene group, a hexamethylene group, a diphenylmethane-2,2'-diyl group, a diphenylethane-3,3'-diyl group, a diphenylpropane-4,4'-diyl group can be given.

As the electron-transmitting compound used in the electron-injecting layer or the electron-transporting layer, a metal complex of 8-hydroxyquinoline or the derivative thereof, an oxadiazole derivative or a nitrogen-containing heterocyclic derivative are preferable. Specific examples of the metal complex of 8-hydroxyquinoline or the derivative thereof include metal chelate oxynoid compounds containing a chelate of oxine (generally, 8-quinolinol or 8-hydroxyquinoline), e.g. tris(8-quinolinolato)aluminum. As examples of the oxadiazole derivative, the following can be given.

given. As the substituent for these, an alkyl group having 1 to 10 carbon atoms, an alkoxy group having 1 to 10 carbon atoms or a cyano group can be given.

As these electron-transmitting compounds, those having excellent capability of forming a thin film are preferably used. As specific examples of the electron-transmitting compound, the following can be given.

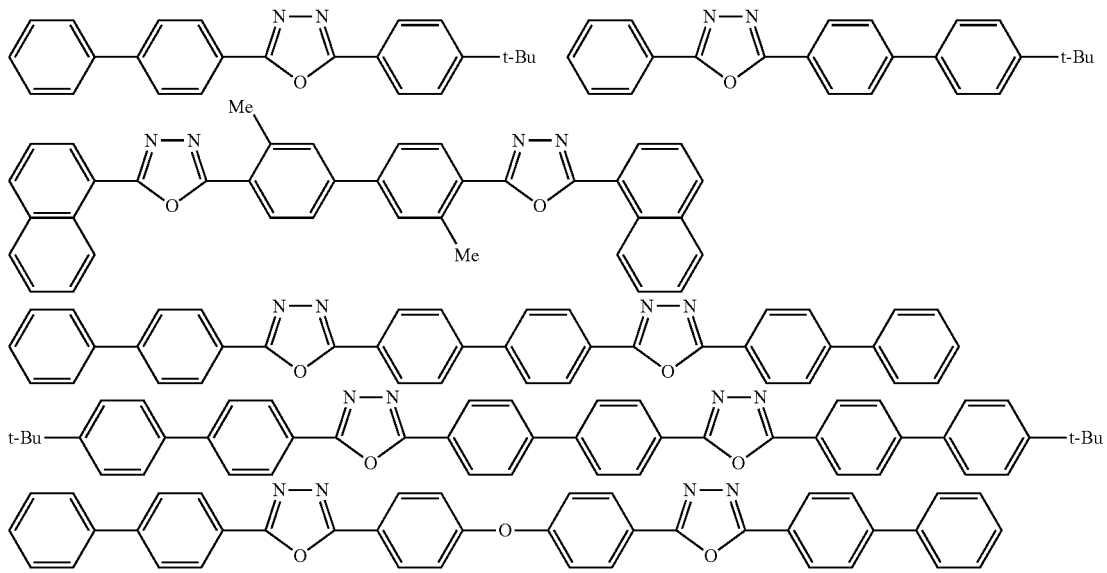

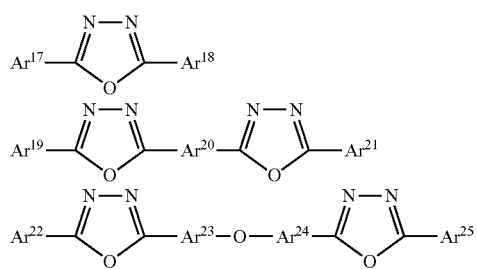

In the above formula, $Ar^{17}$, $Ar^{18}$, $Ar^{19}$, $Ar^{21}$, $Ar^{22}$ and $Ar^{25}$ are independently a substituted or unsubstituted aromatic hydrocarbon group or fused aromatic hydrocarbon group, which may or may not have a substituent. $Ar^{17}$ and $Ar^{18}$, $Ar^{19}$ and $Ar^{21}$, and $Ar^{22}$ and $Ar^{25}$ may be the same or different. As the aromatic hydrocarbon group or the fused aromatic hydrocarbon group, a phenyl group, a naphthyl group, a biphenyl group, an anthranil group, a perylenyl group, a pyrenyl group or the like can be given. As the substituent for these, an alkyl group having 1 to 10 carbon atoms, an alkoxy group having 1 to 10 carbon atoms, a cyano group or the like can be given.

$Ar^{20}$, $Ar^{23}$ and $Ar^{24}$ are independently a divalent aromatic hydrocarbon group or divalent fused aromatic hydrocarbon group which may or may not have a substituent. $Ar^{23}$ and $Ar^{24}$ may be the same or different.

As the divalent aromatic hydrocarbon group or the divalent fused aromatic hydrocarbon group, a phenylene group, a naphthylene group, a biphenylene group, an anthranilene, a perylenylene group, a pyrenylene group or the like can be As the nitrogen-containing heterocyclic derivative as the electron-transmitting compound, a nitrogen-containing heterocyclic compound which is not a metal complex can be given. For example, a 5-membered ring or a 6-membered ring having a skeleton represented by the following formula (B) or a structure represented by the following formula (C) can be given.

In the formula (C), X is a carbon atom or a nitrogen atom. $Z_1$ and $Z_2$ are independently a group of atoms capable of forming a nitrogen-containing hetero ring.

It is further preferred that the nitrogen-containing heterocyclic derivative be an organic compound having a nitrogen-containing aromatic polycyclic group formed of a 5-membered ring or a 6-membered ring. Further, in the case of a nitrogen-containing aromatic polycyclic group having such a plurality of nitrogen atoms, a nitrogen-containing aromatic polycyclic organic compound having a skeleton that is obtained by combining one shown in the formula (B) and one shown in the formula (C) or one shown in the formula (B) and one shown in the formula (D) is preferable.

 (D)

The nitrogen-containing group of the nitrogen-containing aromatic polycyclic organic compound is selected from nitrogen-containing heterocyclic groups represented by the following formulas, for example:

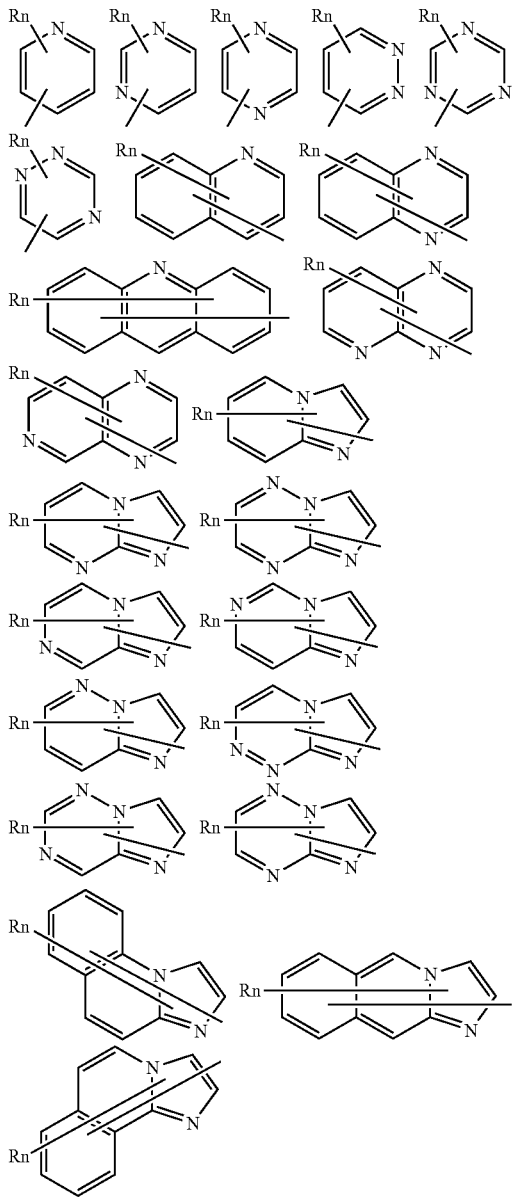

In each of the above formulas, R is an aromatic hydrocarbon group or a fused aromatic hydrocarbon group having 6 to 40 carbon atoms, an aromatic heterocyclic group or a fused aromatic heterocyclic group having 3 to 40 carbon atoms, an alkyl group having 1 to 20 carbon atoms or an alkoxy group having 1 to 20 carbon atoms. n is an integer of 0 to 5, and when n is an integer of 2 or more, plural Rs may be the same or different.

Further, as the preferable specific compound, the nitrogen-containing heterocyclic derivative represented by the following formula can be given.

In the formula, HAr is a nitrogen-containing heterocyclic ring having 3 to 40 carbon atoms, which may have a substituent, $L^1$ is a single bond, an aromatic hydrocarbon group or fused aromatic hydrocarbon group having 6 to 40 ring carbon atoms, which may have a substituent, an aromatic heterocyclic group or fused aromatic heterocyclic group having 3 to 40 carbon atoms, which may have a substituent, $Ar^1$ is a divalent aromatic hydrocarbon group having 6 to 40 ring carbon atoms, which may have a substituent, and $Ar^2$ is an aromatic hydrocarbon group or fused aromatic hydrocarbon group having 6 to 40 ring carbon atoms, which may have a substituent, an aromatic heterocyclic group or fused aromatic heterocyclic group having 3 to 40 carbon atoms, which may have a substituent.

HAr is selected from the following groups, for example.

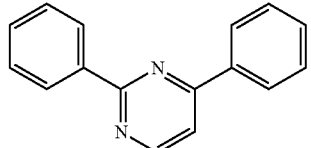

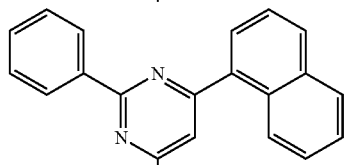

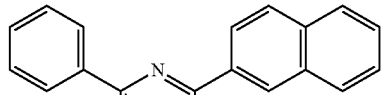

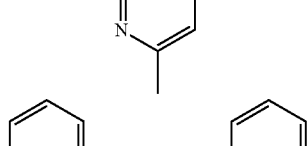

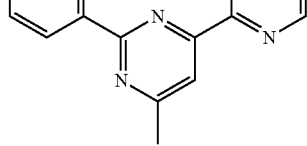

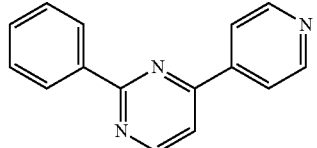

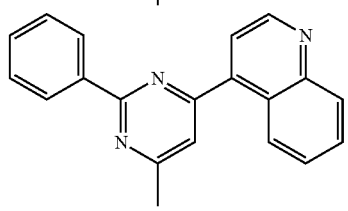

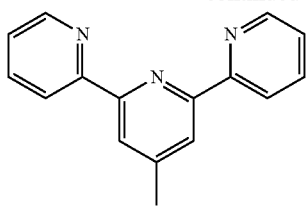
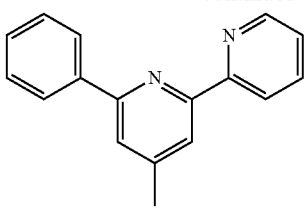

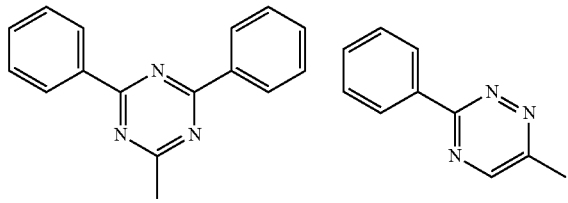

$L^1$ is selected from the following groups, for example.

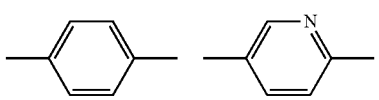

$Ar^1$ is selected from the following arylanthranyl groups, for example.

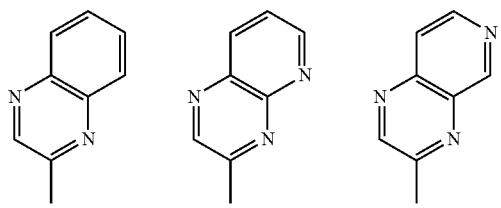
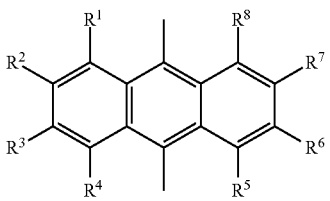

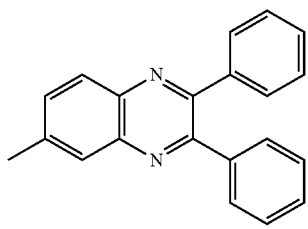
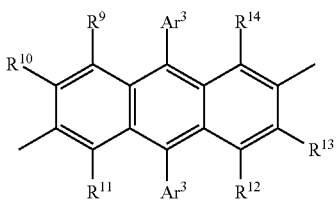

In the above formula, $R^1$ to $R^{14}$ are independently a hydrogen atom, a halogen atom, an alkyl group having 1 to 20 carbon atoms, an alkoxy group having 1 to 20 carbon atoms, an aryloxy group having 6 to 40 carbon atoms, an aromatic hydrocarbon group or fused aromatic hydrocarbon group having 6 to 40 carbon atoms, which may have a substituent or an aromatic heterocyclic group or fused heterocyclic group having 3 to 40 carbon atoms. $Ar^3$ is an aromatic hydrocarbon group or fused aromatic hydrocarbon group having 6 to 40 ring carbon atoms, which may have a substituent, or an aromatic heterocyclic group or fused aromatic heterocyclic group having 3 to 40 carbon atoms, which may have a substituent.

$Ar^2$ is selected from the following groups, for example.

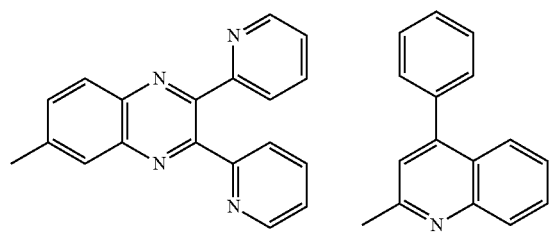

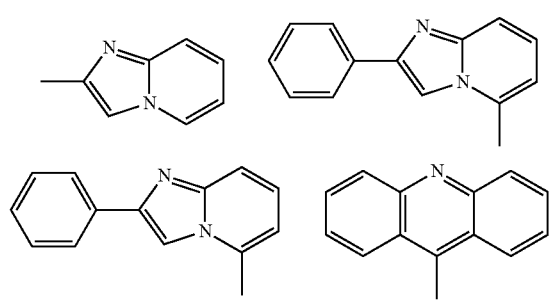
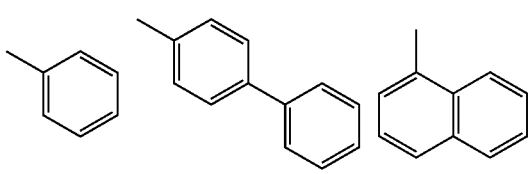

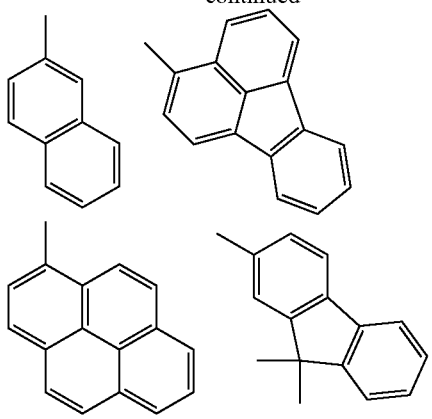

As the nitrogen-containing aromatic polycyclic organic compound as the electron-transmitting compound, in addition to those given above, the following compound is preferably used.

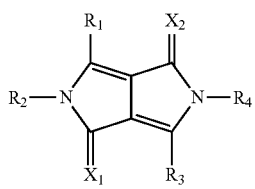

In the above formula, $R_1$ to $R_4$ are independently a hydrogen atom, a substituted or unsubstituted aliphatic group, a substituted or unsubstituted alicyclic group, a substituted or unsubstituted carbocyclic aromatic ring group or a substituted or unsubstituted heterocyclic group. $X_1$ and $X_2$ are independently an oxygen atom, a sulfur atom or a dicyanomethylene group.

As the electron-transmitting compound, the following compound is preferably used.

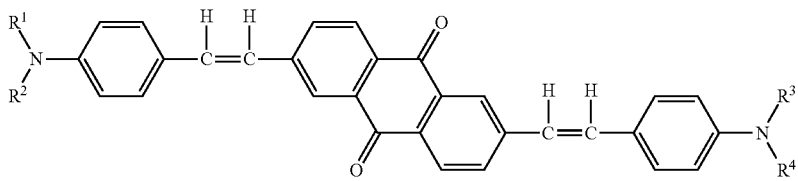

In the above formula, $R^1$, $R^2$, $R^3$ and $R^4$ are the same or different groups from each other, and are independently an aromatic hydrocarbon group or a fused aromatic hydrocarbon group represented by the following formula:

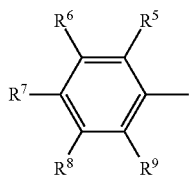

In the above formula, $R^5$, $R^6$, $R^7$, $R^8$ and $R^9$ are the same or different groups from each other, and are independently a hydrogen atom or at least one of them is a saturated or unsaturated alkoxy group, a saturated or unsaturated alkyl group, a saturated or unsaturated amino group or a saturated or unsaturated alkylamino group.

The electron-transmitting compound may be a high-molecular compound containing the nitrogen-containing heterocyclic group or the nitrogen-containing heterocyclic derivative.

It is preferred that the electron-transporting layer contain at least any one of the nitrogen-containing heterocyclic derivatives represented by the following formulas (201) to (203).

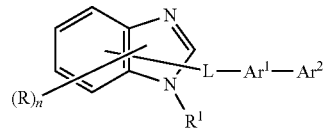

(201)

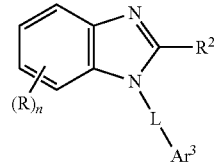

(202)

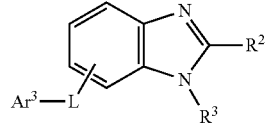

(203)

In the formulas (201) to (203), R is a hydrogen atom, an aromatic hydrocarbon group or fused aromatic hydrocarbon group having 6 to 60 carbon atoms, which may have a substituent, a pyridyl group which may have a substituent, a quinolyl group which may have a substituent, an alkyl group having 1 to 20 carbon atoms which may have a substituent, or an alkoxy group having 1 to 20 carbon atoms which may have a substituent.

n is an integer of 0 to 4.

$R^1$ is an aromatic hydrocarbon group or fused aromatic hydrocarbon group having 6 to 60 carbon atoms, which may have a substituent, a pyridyl group which may have a substituent, a quinolyl group which may have a substituent, an alkyl group having 1 to 20 carbon atoms which may have a substituent, or an alkoxy group having 1 to 20 carbon atoms which may have a substituent.

$R^2$ and $R^3$ are independently a hydrogen atom, an aromatic hydrocarbon group or fused aromatic hydrocarbon group having 6 to 60 carbon atoms, which may have a substituent, a pyridyl group which may have a substituent, a quinolyl group which may have a substituent, an alkyl group having 1 to 20 carbon atoms, which may have a substituent, or an alkoxy group having 1 to 20 carbon atoms, which may have a substituent.

L is an aromatic hydrocarbon group having 6 to 60 carbon atoms which may have a substituent, a pyridinylene group which may have a substituent, a quinolinylene group which may have a substituent or a fluorenylene group which may have a substituent.

$Ar^1$ is an aromatic hydrocarbon group or fused aromatic hydrocarbon group having 6 to 60 carbon atoms which may have a substituent, a pyridinylene group which may have a substituent or a quinolinylene group which may have a substituent. $Ar^2$ is a an aromatic hydrocarbon group or fused aromatic hydrocarbon group having 6 to 60 carbon atoms which may have a substituent, a pyridyl group which may have a substituent, a quinolyl group which may have a substituent, an alkyl group having 1 to 20 carbon atoms which may have a substituent, or an alkoxy group having 1 to 20 carbon atoms which may have a substituent.

$Ar^3$ is an aromatic hydrocarbon group or fused aromatic hydrocarbon group having 6 to 60 carbon atoms, which may have a substituent, a pyridyl group which may have a substituent, a quinolyl group which may have a substituent, an alkyl group having 1 to 20 carbon atoms which may have a substituent, an alkoxy group having 1 to 20 carbon atoms which may have a substituent, or a group represented by —$Ar^1$—$Ar^2$ ($Ar^1$ and $Ar^2$ are as defined above).

In the above formulas (201) to (203), R is a hydrogen atom, an aromatic hydrocarbon group or fused aromatic hydrocarbon group having 6 to 60 carbon atoms, which may have a substituent, a pyridyl group which may have a substituent, a quinolyl group which may have a substituent, an alkyl group having 1 to 20 carbon atoms which may have a substituent, or an alkoxy group having 1 to 20 carbon atoms which may have a substituent.

No specific restrictions are imposed on the thickness of the electron-injecting layer or the electron-transporting layer. The thickness is, however, preferably 1 nm to 100 nm.

As the constituent element of the electron-injecting layer, in addition to the nitrogen-containing heterocyclic derivative, as an inorganic compound, an insulator or a semiconductor is preferably used. If the electron-injecting layer is formed of an insulator or a semiconductor, current leakage can effectively be prevented, whereby electron-injecting properties can be improved.

As the insulator, at least one metal compound selected from the group consisting of alkali metal calcogenides, alkaline earth metal calcogenides, halides of alkali metals and halides of alkaline earth metals can be preferably used. When the electron-injecting layer is formed of the alkali metal calcogenide or the like, the injection of electrons can be preferably further improved. Specifically preferable alkali metal calcogenides include $Li_2O$, $K_2O$, $Na_2S$, $Na_2Se$ and $Na_2O$ and preferable alkaline earth metal calcogenides include CaO, BaO, SrO, BeO, BaS and CaSe. Preferable halides of alkali metals include LiF, NaF, KF, LiCl, KCl and NaCl. Preferable halides of alkaline earth metals include fluorides such as $CaF_2$, $BaF_2$, $SrF_2$, $MgF_2$ and $BeF_2$ and halides other than fluorides.

The semiconductors include one or combinations of two or more of oxides, nitrides, and oxidized nitrides containing at least one element of Ba, Ca, Sr, Yb, Al, Ga, In, Li, Na, Cd, Mg, Si, Ta, Sb and Zn. An inorganic compound forming an electron-injecting layer is preferably a microcrystalline or amorphous insulating thin film. When the electron-injecting layer is formed of the insulating thin films, more uniformed thin film is formed whereby pixel defects such as a dark spot can be decreased. Examples of such an inorganic compound include the above-mentioned alkali metal calcogenides, alkaline earth metal calcogenides, halides of alkali metals, and halides of alkaline earth metals.

If such an insulator or a semiconductor is used, the preferable thickness of the layer is about 0.1 nm to 15 nm. The electron-injecting layer in the invention may preferably contain the above-mentioned reducing dopant.

(Hole-Injecting Layer and Hole-Transporting Layer)

In the hole-injecting layer or the hole-transporting layer (including the hole-injecting/transporting layer), an aromatic amine compound, for example, an aromatic amine derivative represented by the formula (I) can preferably be used.

(I)

In the formula (I), $Ar^1$ to $Ar^4$ are a substituted or unsubstituted aromatic hydrocarbon group or fused aromatic hydrocarbon group having 6 to 50 ring carbon atoms or a substituted or unsubstituted aromatic heterocyclic group or fused aromatic heterocyclic group having 5 to 50 ring atoms or a group obtained by bonding these aromatic hydrocarbon groups or the fused aromatic hydrocarbon groups with an aromatic heterocyclic group or a fused heterocyclic ring group.

Specific examples of the compound represented by the formula (I) are shown below, though not limited thereto.

105
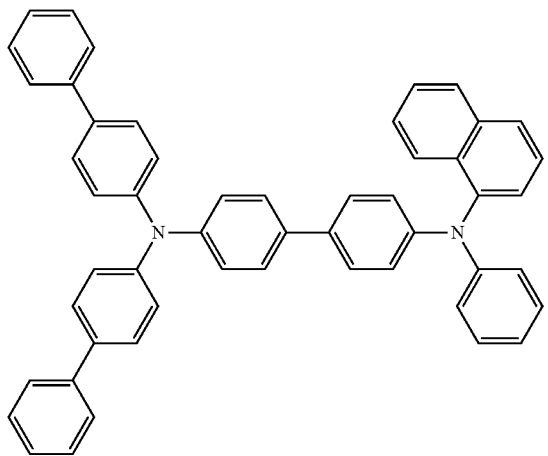
106
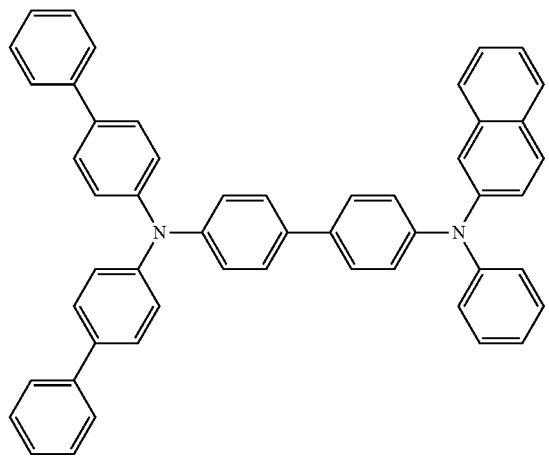
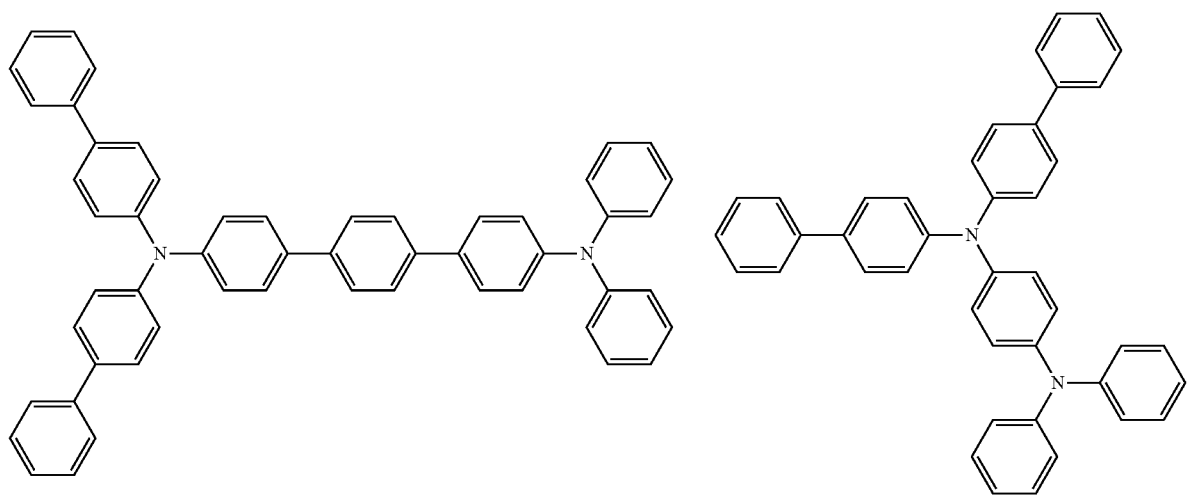
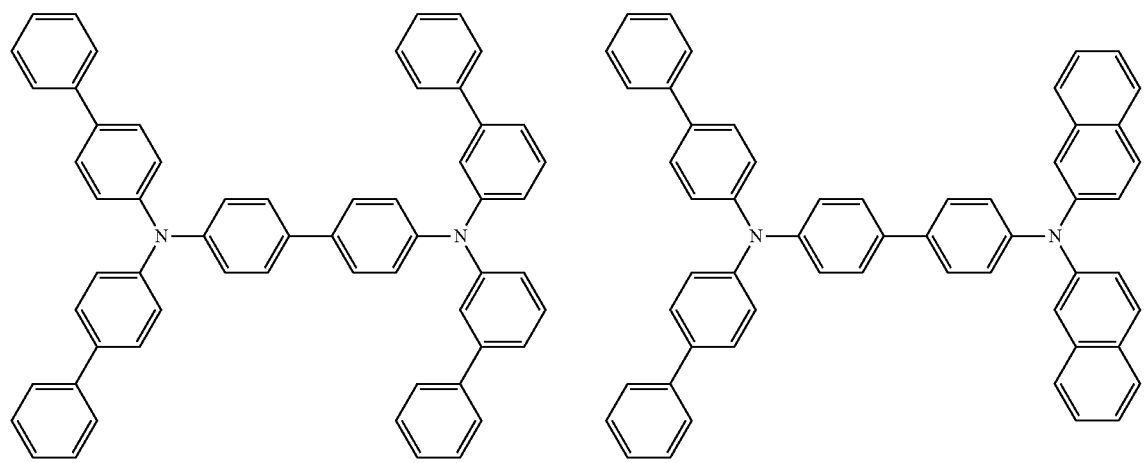

-continued
107 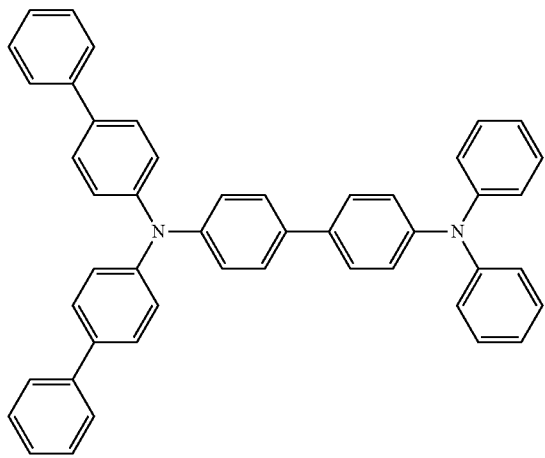
108 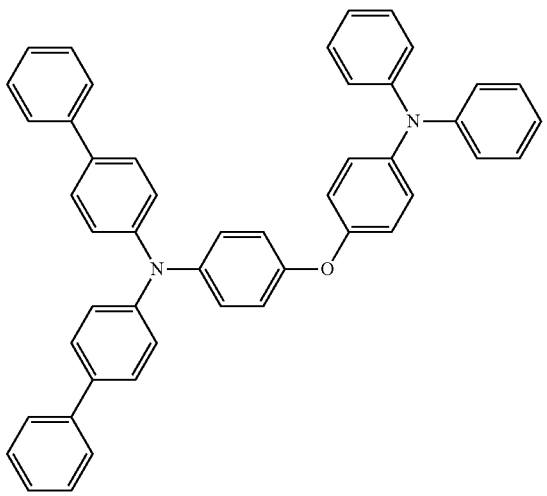
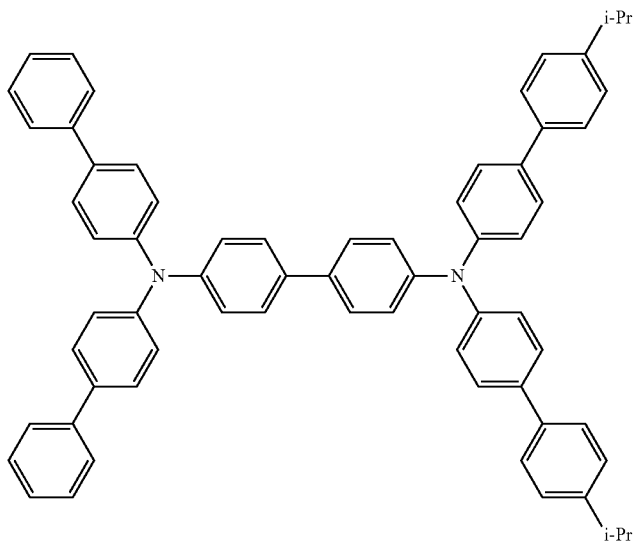
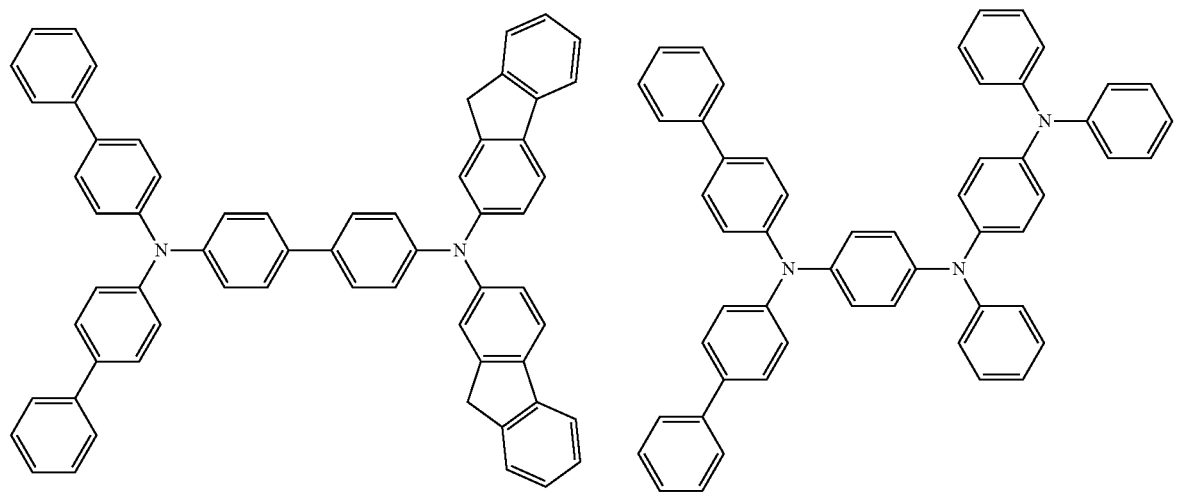

-continued
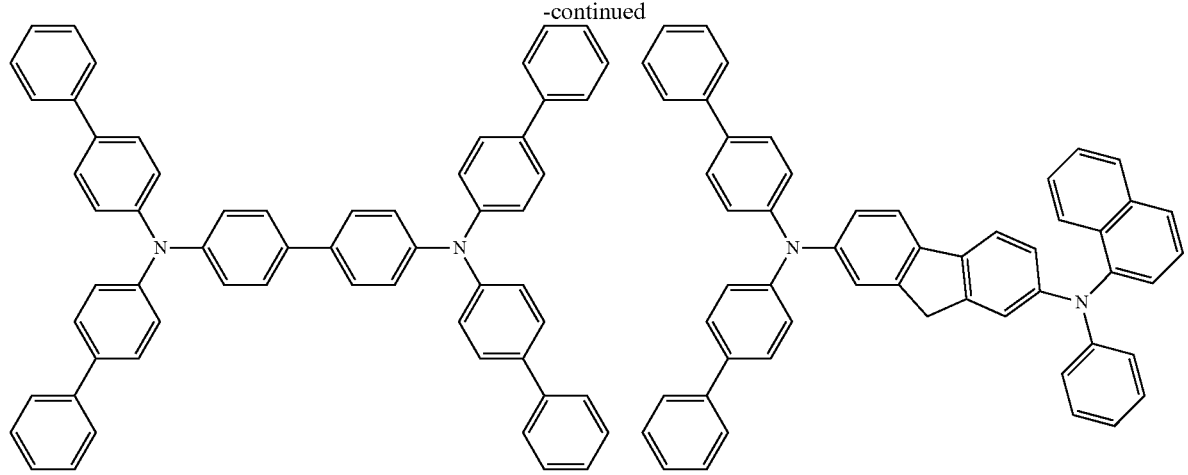
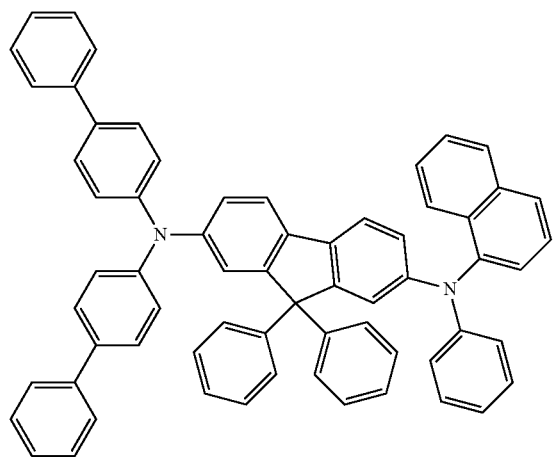
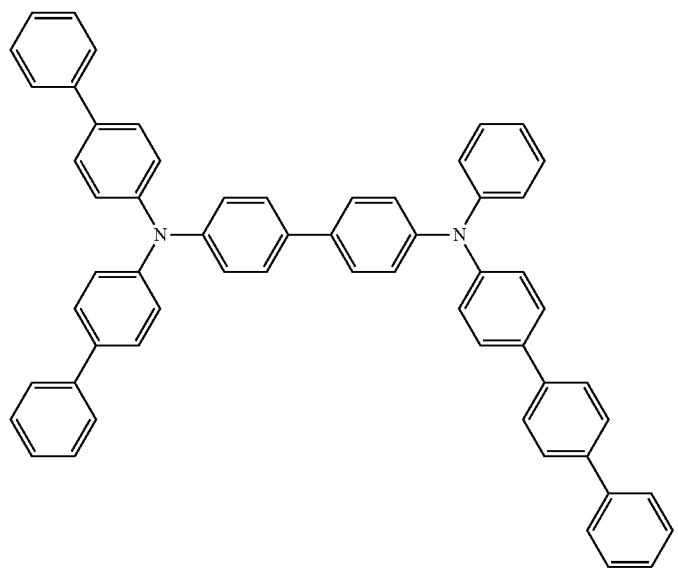

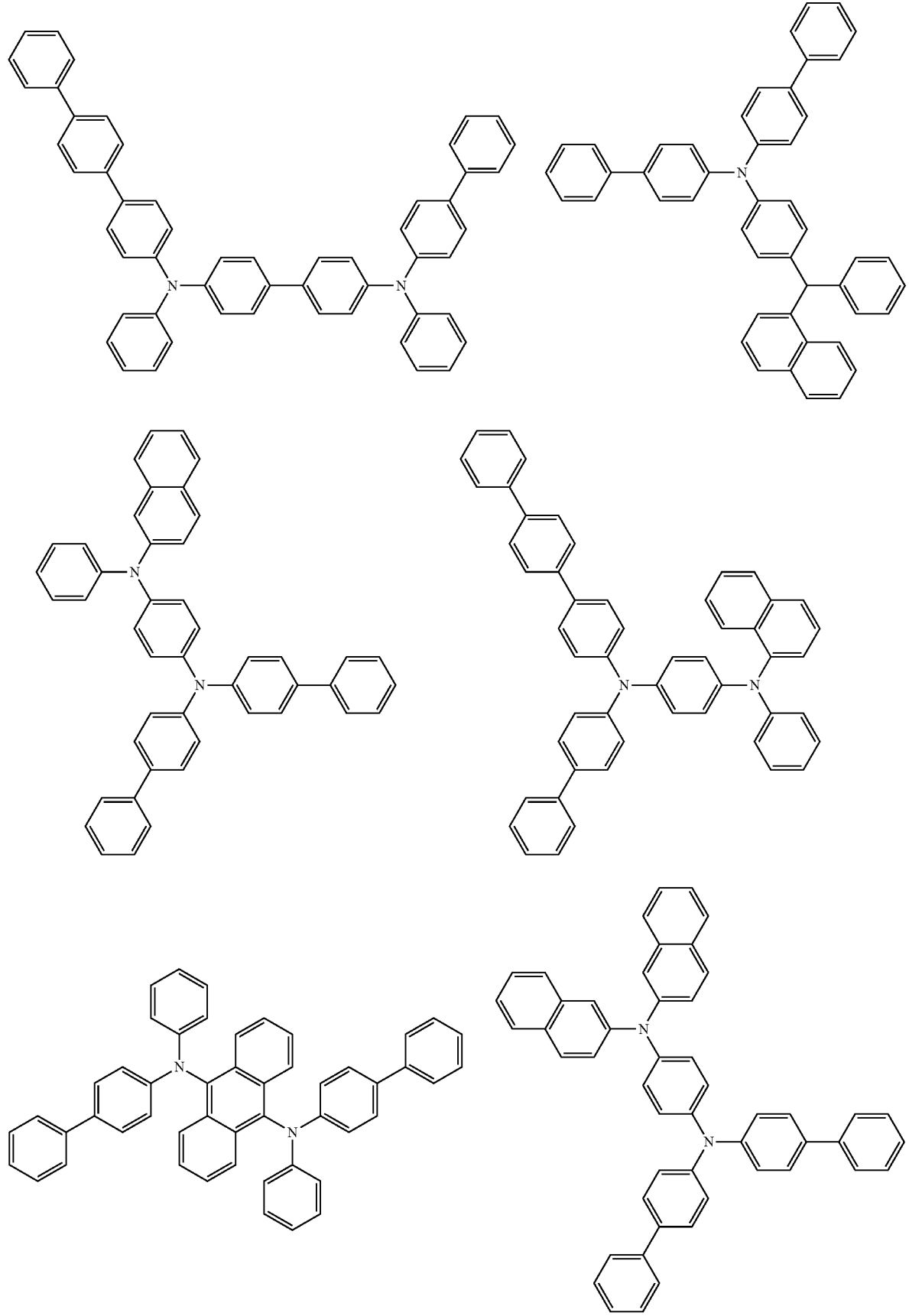

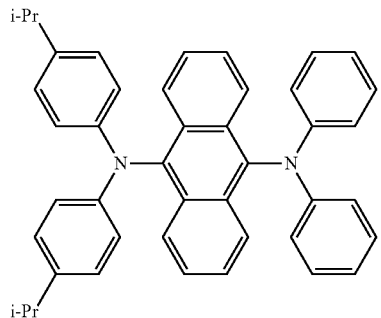
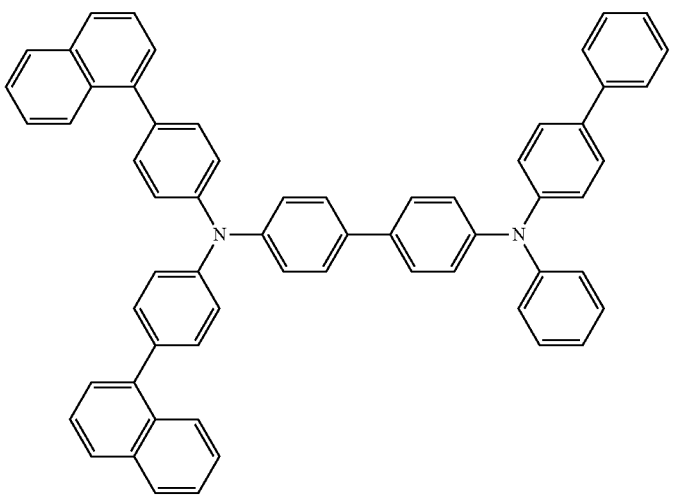
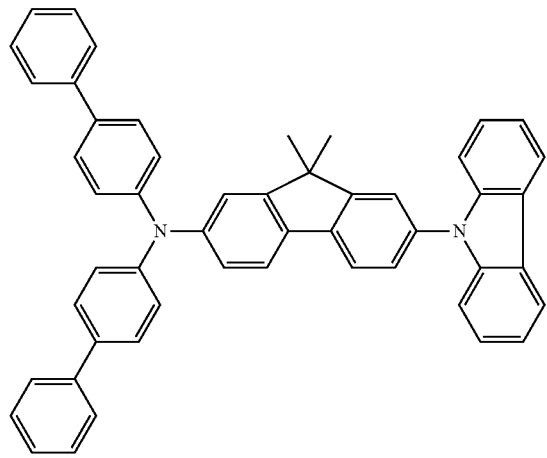
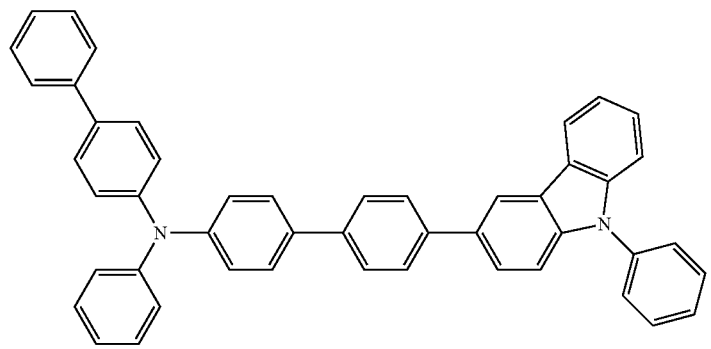
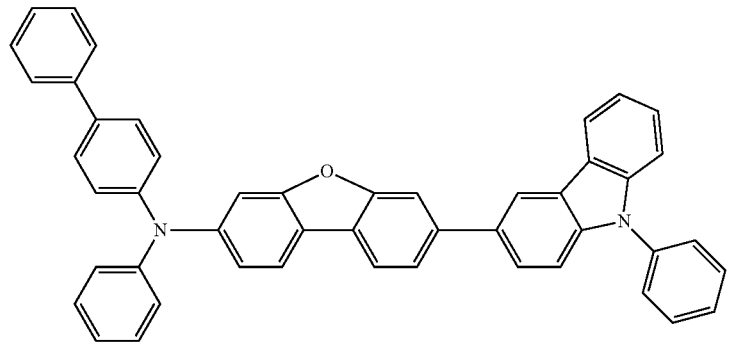

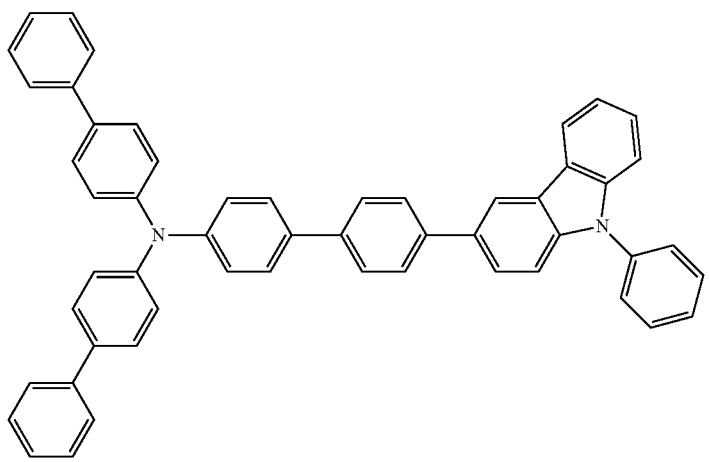
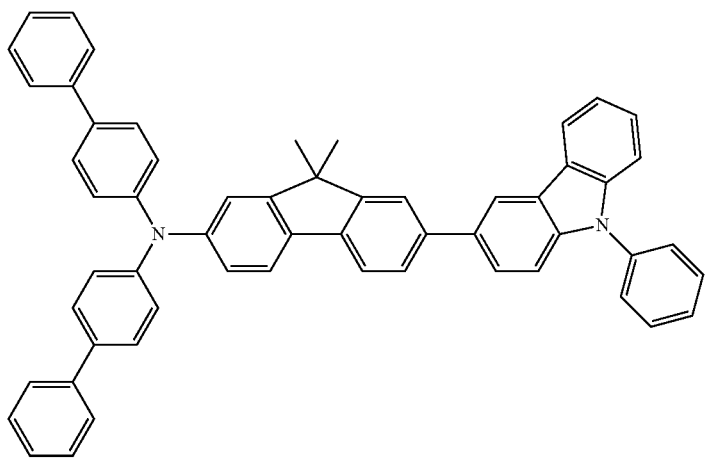
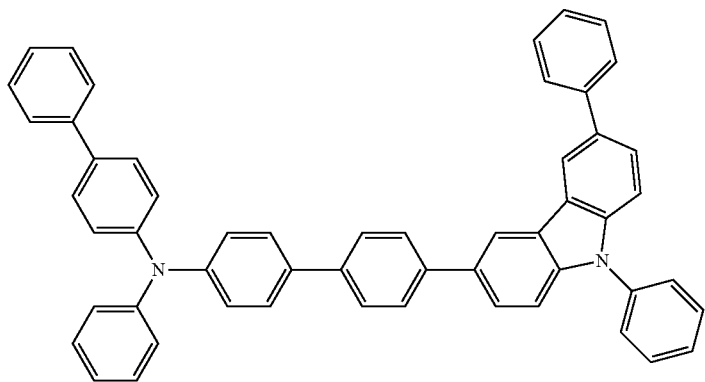
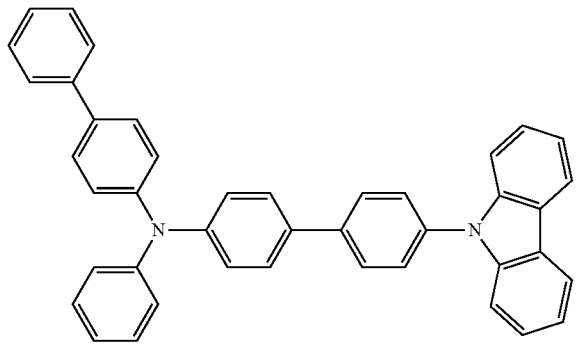

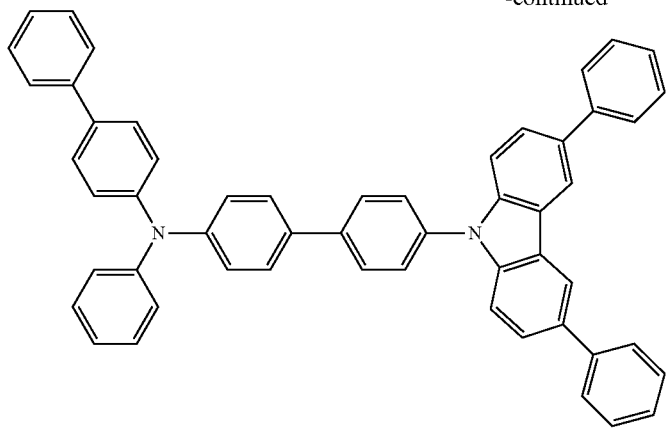

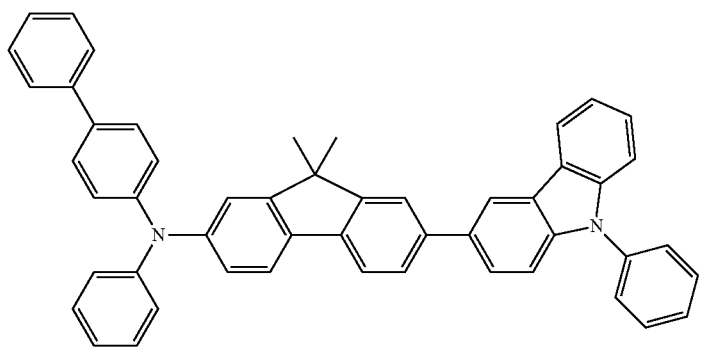

The aromatic amine represented by the following formula (II) is preferably used for forming the hole-injecting layer or the hole-transporting layer.

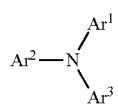
(II)

In the formula (II), the definition of $Ar^1$ to $Ar^3$ is the same as the definition of $Ar^1$ to $Ar^4$ in the formula (I). The specific examples of the compound represented by the formula (II) are shown below, not limited thereto.

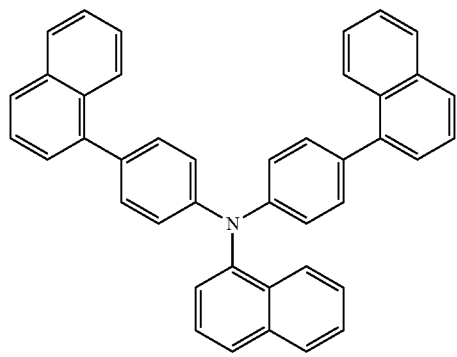

-continued

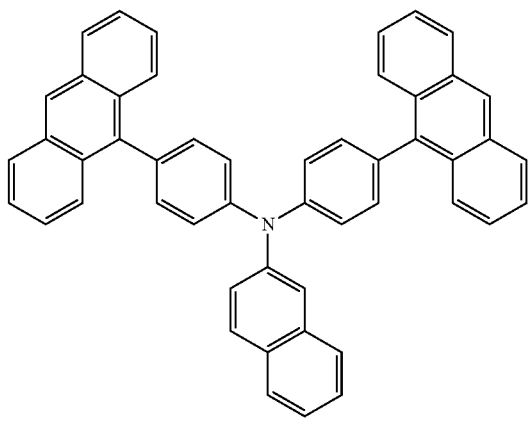

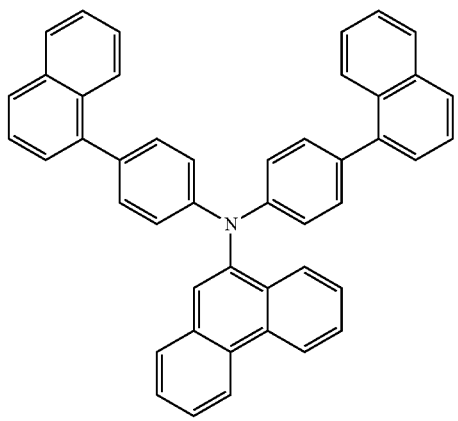

119
-continued
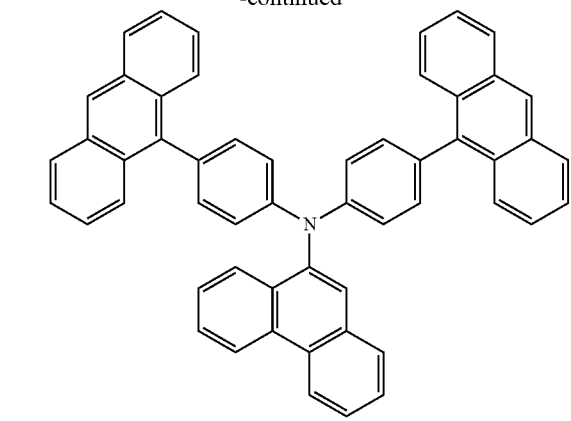
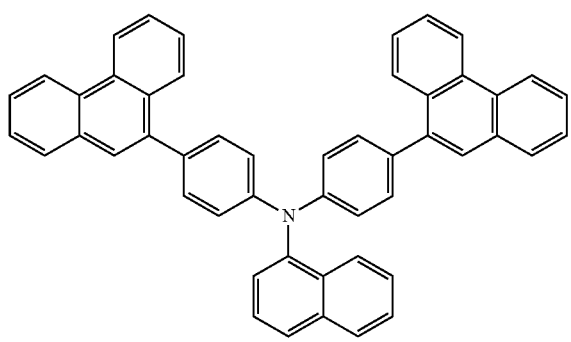
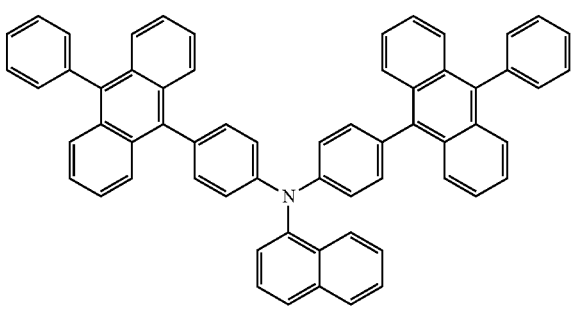
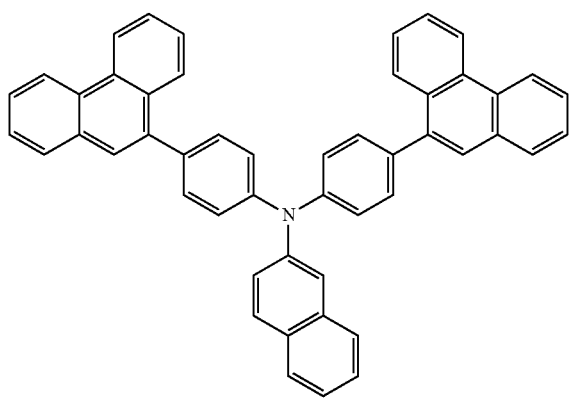
120
-continued
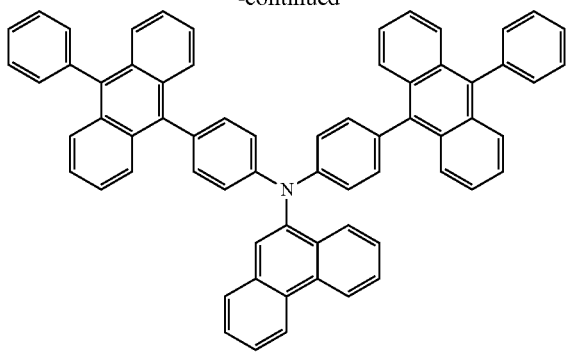
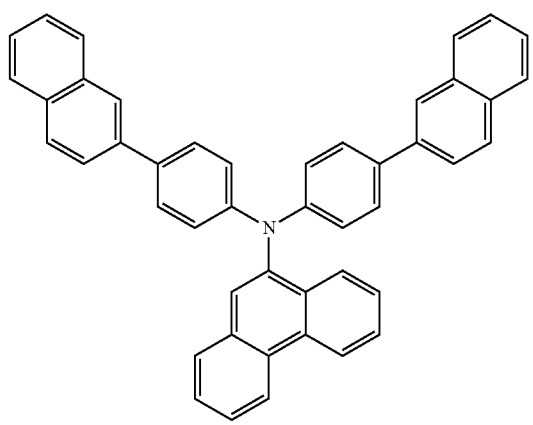
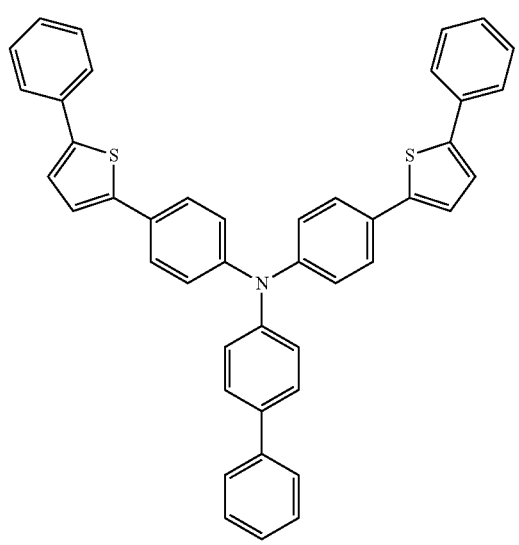
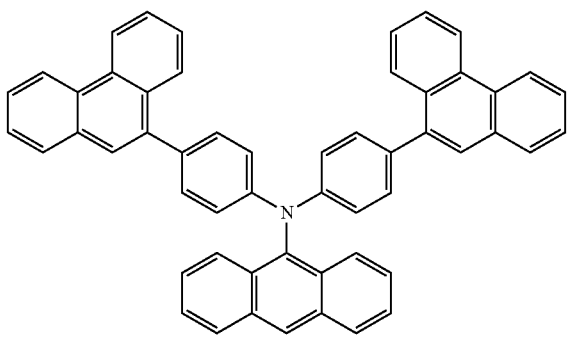

121
-continued

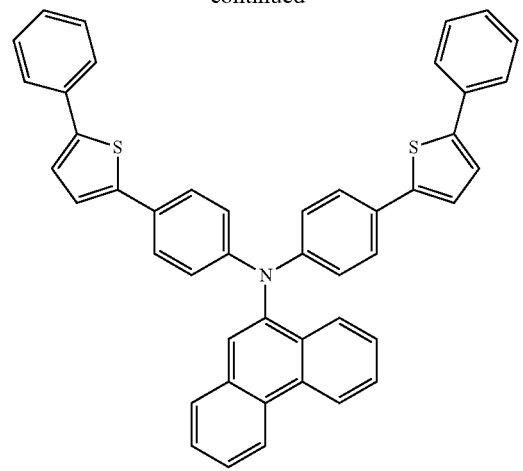

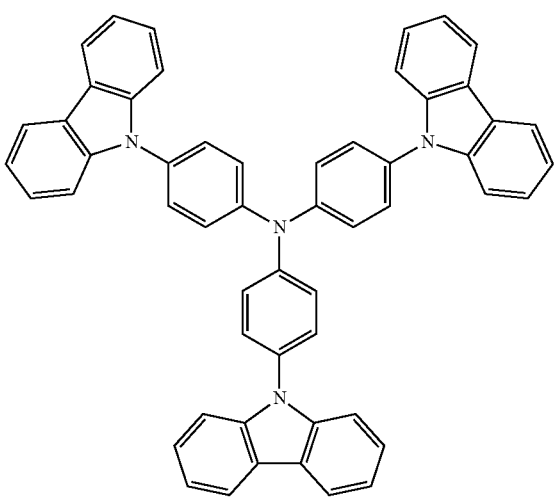

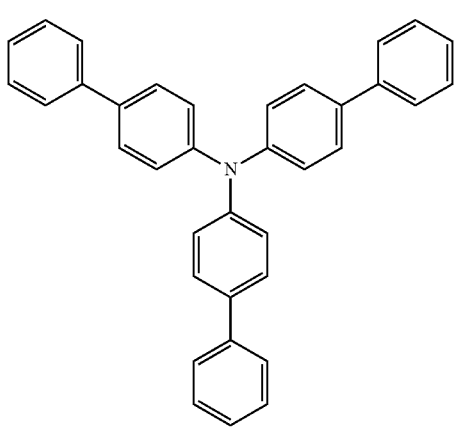

122
-continued

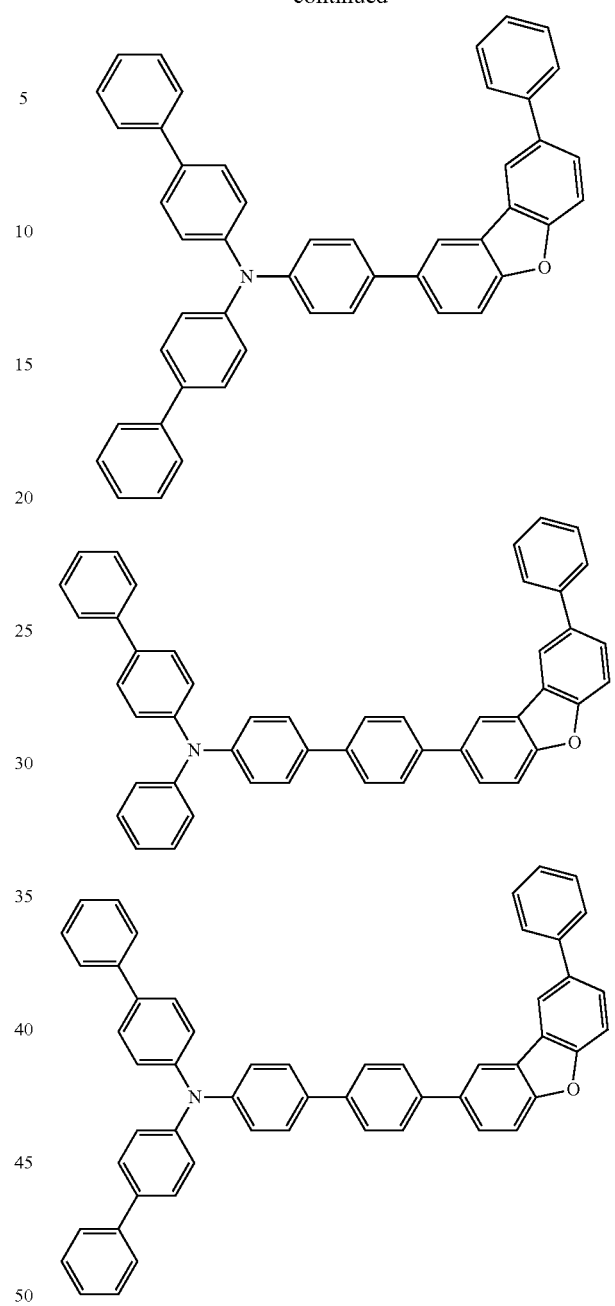

The invention is not limited to the above description, and various modifications are included in the invention as long as they do not deviate from the scope of the invention.

For example, the following modifications are the preferable modification examples of the invention.

In the invention, it is preferred that the emitting layer comprise a carrier injection assisting agent.

If the emitting layer is formed by using a host material having a large energy gap, the difference between the ionization potential (Ip) of the host material and the Ip of the hole-injecting/transporting layer or the like becomes large. As a result, injection of holes to the emitting layer may become difficult, and hence, a driving voltage to obtain a sufficient luminance may be increased.

In such a case, by incorporating a carrier-injection assisting agent having hole-injecting/transporting properties, hole injection to the emitting layer can be facilitated to decrease a driving voltage.

As the carrier-injection assisting agent, common hole-injecting/transporting materials or the like can be used.

Specific examples thereof include a triazole derivative, an oxadiazole derivative, and an imidazole derivative, a polyarylalkane derivative, a pyrazoline derivative, and a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, a polysilane-based copolymer, an aniline-based copolymer and a conductive high-molecular oligomer (a thiophene oligomer, in particular).

Although the above-mentioned materials are used as hole-injecting materials, a porphyrin compound, an aromatic tertiary amine compound and a styrylamine compound are preferable, with an aromatic tertiary amine compound being preferable.

It is preferable to use a compound having two fused aromatic rings in the molecule thereof, for example, 4,4'-bis(N-(1-naphthyl)-N-phenylamino)biphenyl (abbreviated by NPD, hereinafter), and 4,4',4"-tris(N-(3-methylphenyl)-N-phenylamino)triphenylamine (abbreviated by MTDATA, hereinafter) wherein three triphenylamine units are linked in a star-burst form.

A hexazatriphenylene derivative or the like is preferable as a hole-injecting material.

In addition, an inorganic compound such as p-type Si and p-type SiC can also be used as the material of the hole-injecting layer.

The method for forming each of the layers in the organic EL device is not particularly limited, and each layer can be formed by a known method such as a vacuum vapor deposition method, a spin coating method or the like. The organic thin film layer containing the compound represented by the formula (1) used in the organic EL device of the invention can be formed by a known method such as vacuum vapor deposition, molecular beam epitaxy (MBE), or a coating method using a solution in which the compound is dissolved in a solvent, such as dipping, spin coating, casting, bar coating, or roll coating.

The thickness of each organic layer of the organic EL device of the invention is not particularly restricted. In general, if the thickness is too small, defects such as pinholes are likely to occur easily. If the thickness is too large, a high voltage is required to be applied, thereby leading to deterioration in efficiency. Normally, a thickness range of several nm to 1 μm is preferable.

In the compounds described in the specification of the present application, the hydrogen atom contained in the compound includes an isomer differing in number of neutrons, i.e. protium, deuterium and tritium.

EXAMPLES

The invention will be explained in more detail in accordance with Synthesis Examples and Examples, which should not be construed as limiting the scope of the invention.

Synthesis Example 1 (Synthesis of Compound (1))

(1) Synthesis of Compound (1-a)

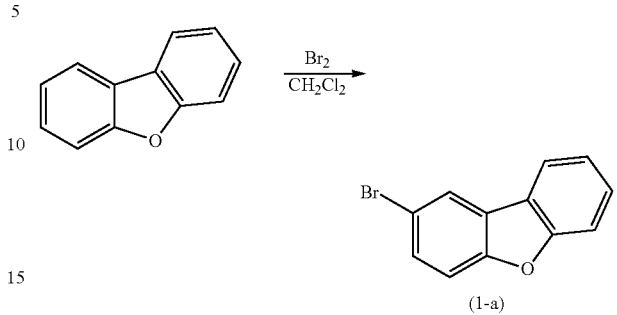

In a three-neck flask, 269.1 g (1600 mmol) of dibenzofuran and 1280 mL of dichloromethane were placed. The reactor was cooled to 0° C. in a nitrogen atmosphere. 100 mL of a dichloromethane solution of 204.6 g of bromine was added dropwise to the reactor over 40 minutes, and the resulting mixture was stirred at room temperature for 12 hours. After completion of the reaction, the reactor was cooled to 0° C. 500 mL of water was added, and further, 100 mL of an aqueous 20% $NaHSO_4$ solution was added. The sample solution was transferred to a separating funnel, and extracted with dichloromethane several times. The resultant was washed with 300 mL of a 1N aqueous solution of sodium hydroxide, dried with anhydrous magnesium sulfate, filtrated and concentrated. The resulting product was washed by dispersing in hexane, whereby white solids were obtained. The yield was 136 g (55%).

(2) Synthesis of Compound (1-b)

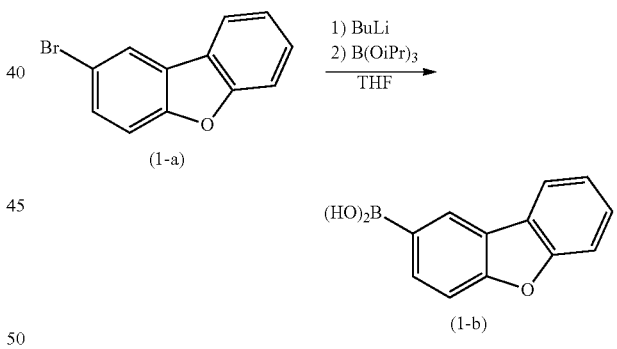

In a three-neck flask, 20.0 g (80.9 mmol) of compound (1-a) and 200 mL of dehydrated tetrahydrofuran were placed. In a nitrogen atmosphere, the reactor was cooled to −70° C. To the reactor, 53 mL (88.9 mmol) of a 1.68M n-butyllithium hexane solution was added dropwise, and the resultant was stirred at −70° C. for 1 hour. To the reactor, 37.3 mL (162 mmol) of triisopropyl borate was added, and the resultant was stirred at room temperature for 6 hours. After completion of the reaction, 100 mL of an aqueous 1N HCl solution was added, followed by stirring for 30 minutes. The sample solution was transferred to a separating funnel, and extracted with dichloromethane several times. The resultant was dried with anhydrous magnesium sulfate, filtrated and concentrated. The resulting product was washed by dispersing in hexane, whereby white solids were obtained. The yield was 15.9 g (93%).

(3) Synthesis of Compound (1-c)

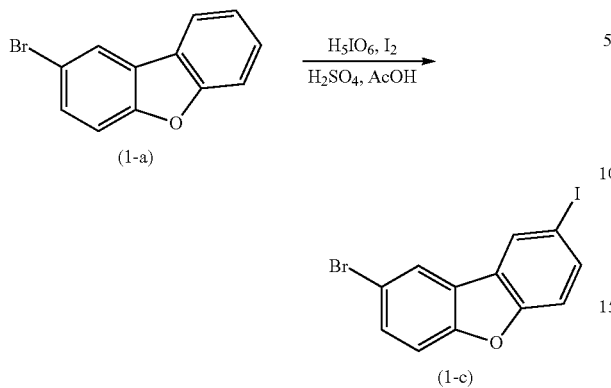

In a three-neck flask, 10.0 g (40.4 mmol) of compound (1-a), 1.96 g (8.60 mmol) of orthoperiodic acid, 4.08 g (16.1 mmol) of iodine, 8 mL of dilute sulfuric acid and 40 mL of acetic acid were placed. The resulting mixture was stirred at 70° C. for 3 hours. After cooling the reactor to room temperature, the reaction solution was added to ice water, and precipitated solids were collected by filtration. The resulting solids were washed with methanol, whereby white solids were obtained. The yield was 6.78 g (45%).

(4) Synthesis of Compound (1-d)

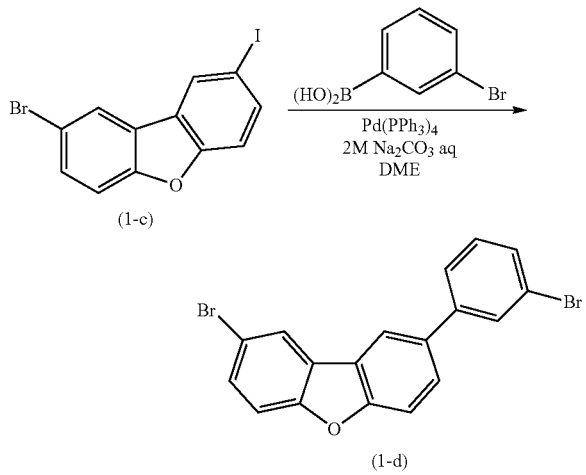

In a three-neck flask, 9.72 g (26.1 mmol) of compound (1-c), 6.02 g (30.0 mmol) of 3-bromophenylboronic acid, 45 mL of a 2M aqueous solution of sodium carbonate, 90 mL of 1,2-dimethoxyethane, and 1.51 g (1.31 mmol) of Pd(PPh$_3$)$_4$ were placed. In a nitrogen atmosphere, the resulting mixture was refluxed for 12 hours.

After completion of the reaction, the sample solution was transferred to a separating funnel, and extracted with ethyl acetate several times. The resultant was dried with anhydrous magnesium sulfate, filtrated and concentrated. The resulting product was purified by silica gel chromatography (hexane:dichloromethane=50:1), whereby white solids were obtained. The yield was 3.65 g (35%).

(5) Synthesis of Compound (1)

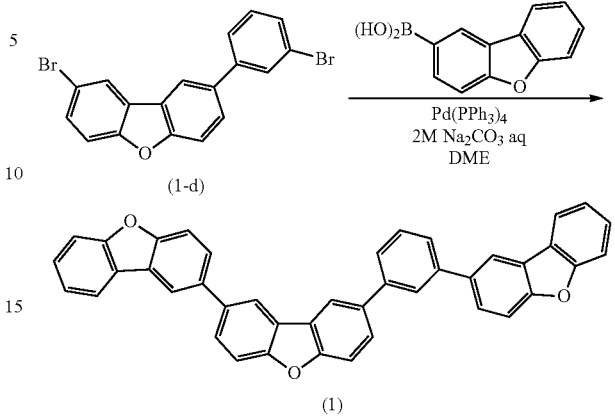

In a three-neck flask, 3.50 g (8.70 mmol) of compound (1-d), 4.39 g (20.7 mmol) of compound (1-b), 30 mL of a 2M aqueous solution of sodium carbonate solution, 60 mL of 1,2-dimethoxyethane and 1.01 g (0.870 mmol) of Pd(PPh$_3$)$_4$ were placed. The resulting mixture was refluxed in a nitrogen atmosphere for 12 hours.

After completion of the reaction, 100 mL of methanol was added to the sample reaction solution, and the resultant was subjected to ultrasonic cleaning for 10 minutes. The precipitated sample was collected by filtration, and washed with methanol, water and hexane. After drying the sample, ethyl acetate was added to conduct washing by dispersion. The resulting solids were re-crystallized from toluene, whereby white solids were obtained. The identification was conducted by the molecular weight measurement by FD/MS. It was found that m/e was 576 relative to the molecular weight 576. The yield was 3.06 g (61%).

Synthesis Example 2 (Synthesis of Compound (81))

(1) Synthesis of Compound (81-a)

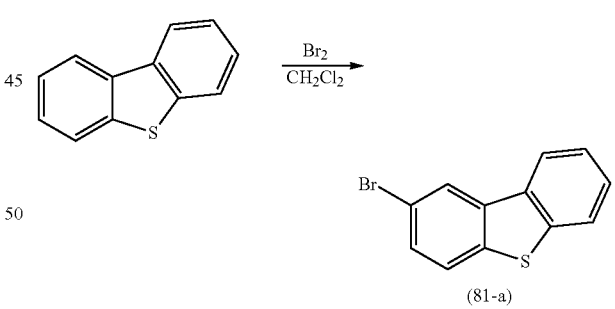

In a three-neck flask, 15.0 g (81.4 mmol) of dibenzothiophene and 90 mL of chloroform were placed. The reactor was cooled to 0° C. in a nitrogen atmosphere. 20 mL of a dichloromethane solution of 13.1 g of bromine was added dropwise to the reactor over 15 minutes, and the resulting mixture was stirred at room temperature for 12 hours. After completion of the reaction, the reactor was cooled to 0° C. 100 mL of water was added, and further, 30 mL of an aqueous 20% NaHSO$_4$ solution was added. The sample solution was transferred to a separating funnel, and extracted with dichloromethane several times. The resultant was washed with 30 mL of a 1N aqueous solution of sodium hydroxide, dried with anhydrous magnesium sulfate, filtrated and concentrated. The resulting product was washed by dispersing in hexane and methanol, whereby white solids were obtained. The yield was 10.7 g (50%).

(2) Synthesis of Compound (81-b)

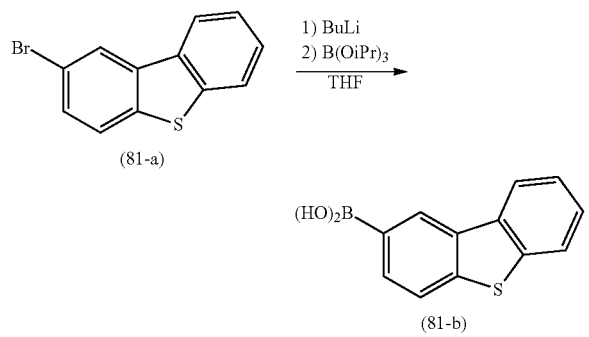

In a three-neck flask, 7.00 g (26.6 mmol) of compound (81-a) and 80 mL of dehydrated tetrahydrofuran were placed. In a nitrogen atmosphere, the reactor was cooled to −70° C. To the reactor, 23 mL (37.2 mmol) of a 1.60M n-butyllithium hexane solution was added dropwise, and the resultant was stirred at −70° C. for 1 hour. To the reactor, 12.3 mL (53.2 mmol) of triisopropyl borate was added, and the resultant was stirred at room temperature for 6 hours. After completion of the reaction, 50 mL of a 1N aqueous HCl solution was added, followed by stirring for 30 minutes. The sample solution was transferred to a separating funnel, and extracted with dichloromethane several times. The resultant was dried with anhydrous magnesium sulfate, filtrated and concentrated. The resulting product was washed by dispersing in hexane, whereby white solids were obtained. The yield was 5.76 g (95%).

(3) Synthesis of Compound (81-c)

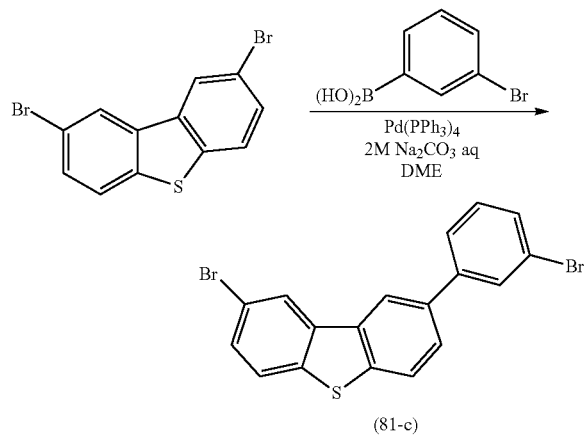

In a three-neck flask, 10.0 g (29.2 mmol) of 2,8-dibromodibenzothiophene, 5.86 g (29.2 mmol) of 3-bromophenylboronic acid, 44 mL of a 2M aqueous sodium carbonate solution, 88 mL of 1,2-dimethoxyethane, and 3.37 g (2.92 mmol) of Pd(PPh$_3$)$_4$ were placed, and the resulting mixture was refluxed for 12 hours in a nitrogen atmosphere.

After completion of the reaction, the mixture was transferred to a separating funnel and the sample solution was extracted several times with ethyl acetate. The resultant was dried with anhydrous magnesium sulfate, and filtrated and concentrated. The resulting product was purified by silica gel chromatography (hexane:dichloromethane=50:1), whereby white solids were obtained. The yield was 2.44 g (20%).

(4) Synthesis of Compound (81)

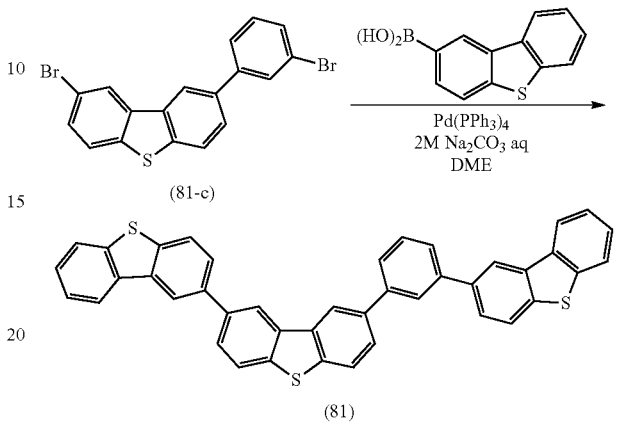

In a three-neck flask, 2.00 g (4.78 mmol) of compound (81-c), 2.61 g (11.4 mmol) of compound (81-b), 17 mL of a 2M aqueous sodium carbonate solution, 34 mL of 1,2-dimethoxyethane and 0.552 g (0.478 mmol) of Pd(PPh$_3$)$_4$ were placed, and the resulting mixture was refluxed in a nitrogen atmosphere for 12 hours.

After completion of the reaction, 100 mL of methanol was added to the sample solution, and the resultant was subjected to ultrasonic cleaning for 10 minutes. The precipitated sample was collected by filtration, and washed with methanol, water and hexane. After drying the sample, a mixed solvent of hexane and ethyl acetate (hexane:ethyl acetate=1:1) was added, and ultrasonic cleaning was conducted for 30 minutes, whereby white solids were obtained. The identification was conducted by the molecular weight measurement by FD/MS. It was found that m/e was 624 relative to the molecular weight 624. The yield was 1.64 g (55%).

Synthesis Example 3 (Synthesis of Compound (17))

(1) Synthesis of Compound (17-a)

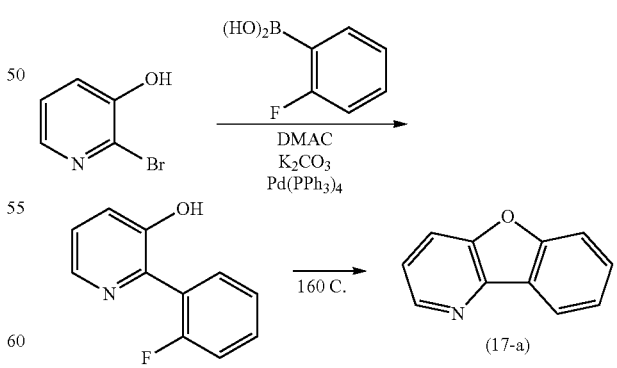

In a three-neck flask, 100.1 g (57.5 mmol) of 2-bronco-3-hydroxypyridine, 88.5 g (032.5 mmol) of 2-fluorophenylboronic acid, 88.5 g (2300 mmol) of potassium carbonate, 1150 mL of N,N-dimethylacetoamide, and 13.3 g (11.5 mmol) of Pd(PPh$_3$)$_4$ were placed, and the resulting mixture was refluxed in a nitrogen atmosphere at 90° C. for 12 hours in a nitrogen atmosphere. Thereafter, the mixture was stirred with heating at 160° C. for 8 hours.

After completion of the reaction, the sample solution was cooled to room temperature. 1 L of toluene and 1 L of water were added to the sample solution, and the resultant was transferred to a separating funnel and shaken sufficiently. A toluene phase was collected, and extraction from an aqueous phase was conducted with toluene several times. This toluene solution was further washed with water several times, dried with anhydrous magnesium sulfate, passed through a silica gel short column, and concentrated. The resulting sample was re-crystallized from 200 mL of hexane, whereby pale yellowish solids were obtained.

The identification was conducted by $^1$H-NMR. The yield was 54.4 g (56%).

(2) Synthesis of Compound (17-b)

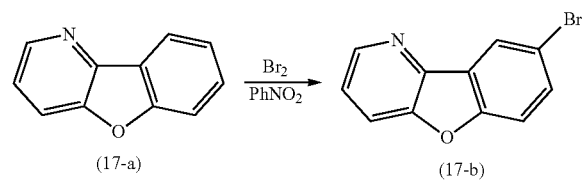

In a three-neck flask, 52.6 g (310 mmol) of compound (17-a), 155 mL of nitrobenzene and 19.1 mL (372 mmol) of bromine were placed. The resulting mixture was stirred with heating in an atmosphere at 140° C. for 12 hours.

After completion of the reaction, the sample solution was cooled to room temperature. While cooling in ice water bath, an aqueous sodium thiosulfate solution was added to the sample solution to allow remaining bromine to be deactivated. Further, an aqueous solution of sodium hydroxide was added to adjust the pH of an aqueous phase to be 10. The solution was transferred to a separating funnel, and extracted with toluene several times. The resultant was dried with anhydrous magnesium sulfate, filtrated and concentrated. The resulting product was purified by silica gel chromatography (dichloromethane:ethyl acetate=8:2), and the sample thus obtained was washed by dispersing in hexane, collected by filtration, and dried in vacuum (40° C., 6 hours), whereby pale yellowish solids were obtained.

The identification was conducted by $^1$H-NMR. The yield was 32.1 g (42%).

(3) Synthesis of Compound (17-c)

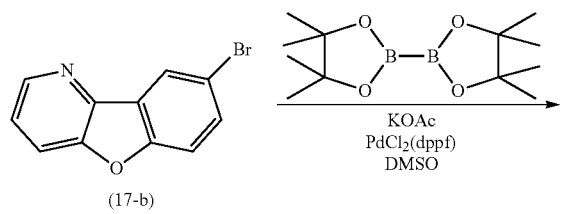

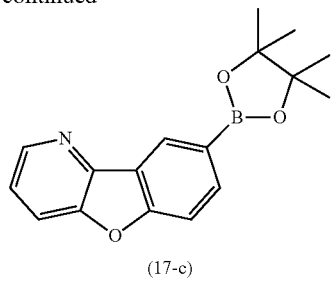

In a three-neck flask, 18.0 g (72.6 mmol) of compound (17-b), 27.6 g (108.9 mmol) of bis(pinacolato)diboron, 21.4 g (217.8 mmol) of potassium acetate, 2.96 g (3.63 mmol) of PdCl$_2$(dppf) and 150 mL of dimethylsulfoxide were placed. The resulting mixture was stirred at 80° C. for 16 hours in a nitrogen atmosphere.

After completion of the reaction, celite filtration was conducted. 300 mL of water was added, and the sample solution was transferred to a separating funnel. The sample solution was extracted several times with toluene, and dried with anhydrous magnesium sulfate, filtrated and concentrated. The resulting product was purified by silica gel chromatography (hexane:ethyl acetate=1:5), and re-crystallized from hexane, whereby white solids were obtained. The yield was 4.20 g (20%).

(4) Synthesis of Compound (17)

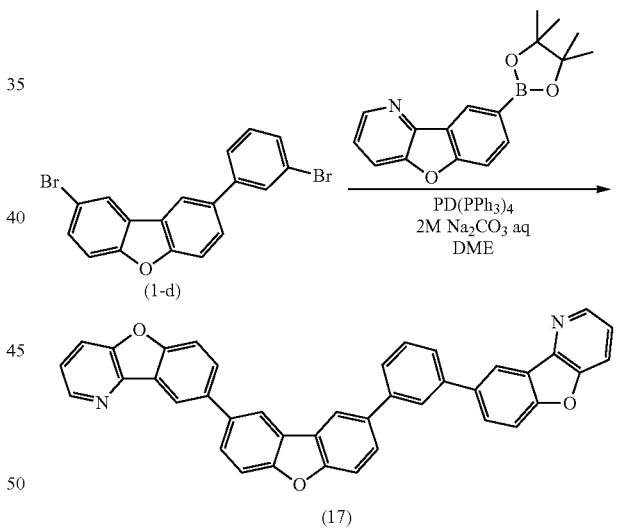

In a three-neck flask, 2.55 g (6.33 mmol) of compound (1-d), 4.50 g (15.2 mmol) of compound (17-c), 25 mL of a 2M aqueous sodium carbonate solution, 50 mL of 1,2-dimethoxyethane and 1.76 g (1.52 mmol) of Pd(PPh$_3$)$_4$ were placed. The resulting mixture was refluxed for 12 hours in a nitrogen atmosphere.

After completion of the reaction, 100 mL of methanol was added to the sample solution, and ultrasonic cleaning was conducted for 10 minutes. The precipitated sample was collected by filtration, and washed with methanol, water and hexane. After drying the sample, dispersion washing was conducted by adding ethyl acetate. The resulting solids were re-crystallized from toluene, whereby white solids were obtained. The identification was conducted by the molecular weight measurement by FD/MS. It was found that m/e was 578 relative to the molecular weight 578. The yield was 2.00 g (55%).

Synthesis Example 4 (Synthesis of Compound (129))

(1) Synthesis of Compound (129-a)

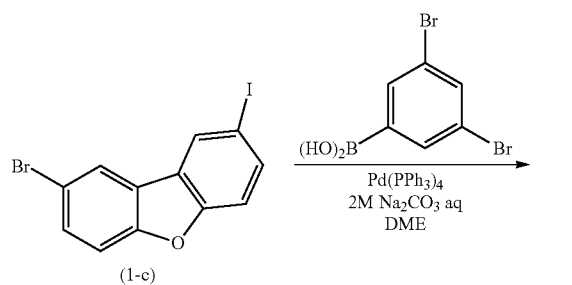

In a three-neck flask, 10.0 g (26.8 mmol) of compound (1-c), 8.62 g (30.8 mmol) of 3,5-dibromophenylboronic acid, 45 mL of a 2M aqueous sodium carbonate solution, 90 of 1,2-dimethoxyethane and 1.55 g (1.34 mmol) of Pd(PPh$_3$)$_4$ were placed. The resulting mixture was refluxed for 16 hours in a nitrogen atmosphere.

After completion of the reaction, 50 ml of hexane and 50 ml of methanol were added to the sample solution, and ultrasonic cleaning was conducted for 10 minutes. Precipitated sample was collected by filtration, and washed with methanol, water and hexane. After drying the sample, ethyl acetate was added to conduct washing by dispersion. The resulting solids were re-crystallized from toluene, whereby white solids were obtained. The identification was conducted by the molecular weight measurement by FD/MS. The yield was 6.50 g (50%).

(2) Synthesis of Compound (129)

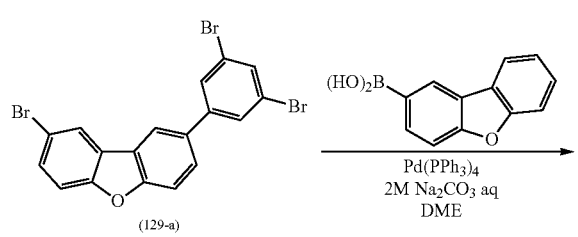

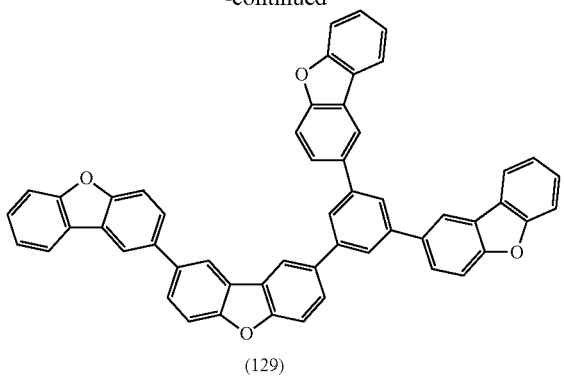

In a three-neck flask, 3.50 g (7.28 mmol) of compound (129-a), 6.95 g (32.8 mmol) of compound (1-b), 50 mL of a 2M aqueous sodium carbonate solution, 100 mL of 1,2-dimethoxyethane and 0.841 g (0.728 mmol) of Pd(PPh$_3$)$_4$ were placed. The resulting mixture was refluxed for 16 hours in a nitrogen atmosphere.

After completion of the reaction, 100 mL of methanol was added to the sample solution, and ultrasonic cleaning was conducted for 10 minutes. The precipitated sample was collected by filtration, and washed with methanol, water and hexane. After drying the sample, a mixed solvent of hexane and ethyl acetate (hexane:ethyl acetate=1:1) was added, and ultrasonic cleaning was conducted for 30 minutes, whereby white solids were obtained. The identification was conducted by the molecular weight measurement by FD/MS. It was found that m/e was 742 relative to the molecular weight 742. The yield was 1.65 g (30%).

Synthesis Example 5 (Synthesis of Compound (135))

(1) Synthesis of Compound (135)

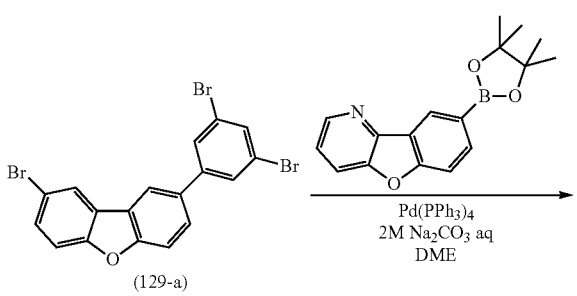

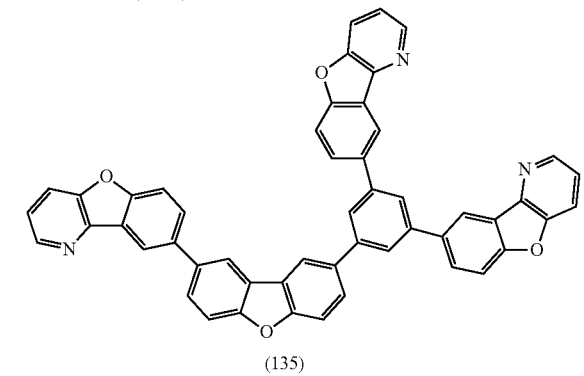

In a three-neck flask, 2.50 g (5.20 mmol) of compound (129-a), 6.44 g (21.8 mmol) of compound (17-c), 30 mL of a 2M aqueous sodium carbonate solution, 60 mL of 1,2-dimethoxyethane and 0.601 g (0.520 mmol) of Pd(PPh$_3$)$_4$ were placed. The resulting mixture was refluxed for 16 hours in a nitrogen atmosphere.

After completion of the reaction, 100 mL of methanol was added to the sample solution, and ultrasonic cleaning was conducted for 10 minutes. The precipitated sample was collected by filtration, and washed with methanol, water and hexane. After drying the sample, a mixed solvent of hexane and ethyl acetate (hexane:ethyl acetate=1:1) was added, and ultrasonic cleaning was conducted for 30 minutes, whereby white solids were obtained. The identification was conducted by the molecular weight measurement by FD/MS. It was found that m/e was 745 relative to the molecular weight 745. The yield was 1.50 g (3096).

Synthesis Example 6 (Synthesis of Compound (144))

(1) Synthesis of Compound (144-a)

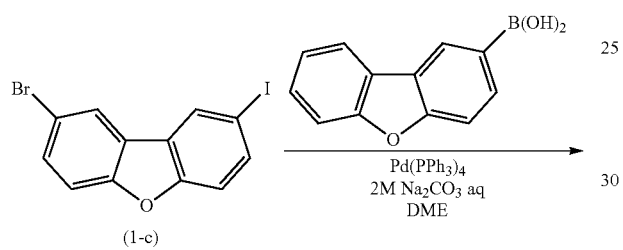

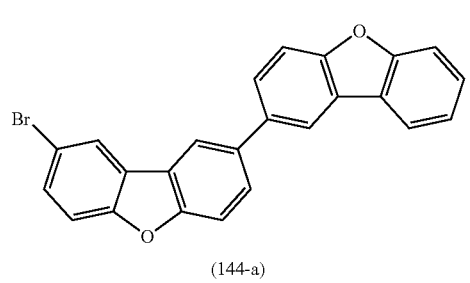

(144-a)

In a three-neck flask, 10.0 g (26.8 mmol) of compound (1-c), 6.82 g (322 mmol) of 3-bromophenylboronic acid, 50 mL of a 2M aqueous sodium carbonate solution, 100 mL of 1,2-dimethoxyethane and 1.55 g (1.34 mmol) of Pd(PPh$_3$)$_4$ were placed. The resulting mixture was refluxed for 12 hours in a nitrogen atmosphere.

After completion of the reaction, the sample solution was transferred to a separating funnel, and extracted with ethyl acetate with several times. The resultant was dried with anhydrous magnesium sulfate, filtrated and concentrated. The resulting product was purified by silica gel chromatography (hexane:ethyl acetate=20:1), whereby white solids were obtained. The yield was 6.32 g (59%).

(2) Synthesis of Compound (144-b)

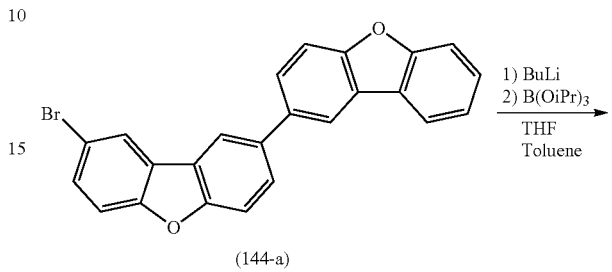

In a three-neck flask, 9.46 g (22.9 mmol) of compound (144-a) and 80 mL of a mixed solution of dehydrated tetrahydrofuran and dehydrated toluene (dehydrated tetrahydrofuran:dehydrated toluene=1:1) were placed. In a nitrogen atmosphere, the reactor was cooled to −70° C. To the reactor, 17 mL (27.5 mmol) of a 1.65M n-butyllithium hexane solution was added dropwise, and the resultant was stirred at −70° C. for 1 hour. To the reactor, 10.6 mL (45.8 mmol) of triisopropyl borate was added, and the resultant was stirred at room temperature for 6 hours. After completion of the reaction, 50 mL of an aqueous 1N HCl solution was added, followed by stirring for 30 minutes. The sample solution was transferred to a separating funnel, and extracted with dichloromethane several times. The resultant was dried with anhydrous magnesium sulfate, filtrated and concentrated. The resulting product was washed by dispersing in hexane, whereby white solids were obtained. The yield was 8.08 g (93%).

(3) Synthesis of Compound (144)

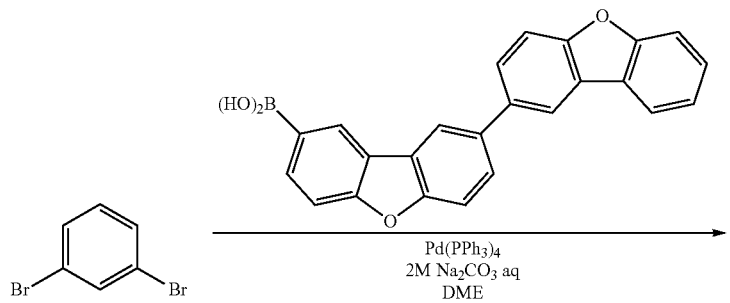

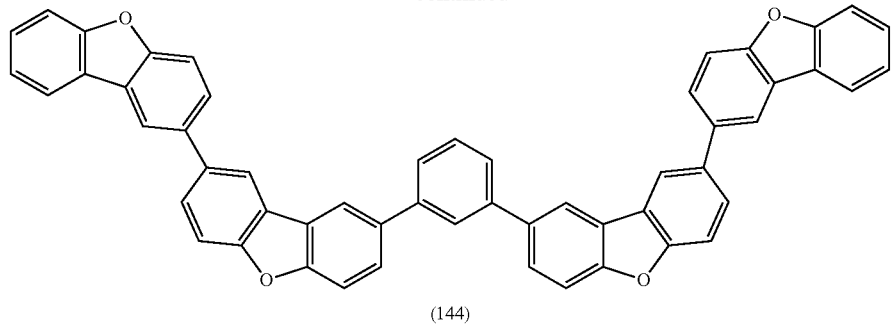

(144)

In a three-neck flask, 2.50 g (10.6 mmol) of 1,3-dibromobenzene, 10.0 g (26.5 mmol) of compound (144-b), 40 mL of a 2M aqueous sodium carbonate solution, 80 of 1,2-dimethoxyethane and 2.45 g (2.12 mmol) of Pd(PPh$_3$)$_4$ were placed. The resulting mixture was refluxed for 16 hours in a nitrogen atmosphere.

After completion of the reaction, 100 mL of methanol was added to the sample solution, and ultrasonic cleaning was conducted for 10 minutes. The precipitated sample was collected by filtration, and washed with methanol, water and hexane. After drying the sample, a mixed solvent of hexane and ethyl acetate (hexane:ethyl acetate=1:1) was added, and ultrasonic cleaning was conducted for 30 minutes, whereby white solids were obtained. The identification was conducted by the molecular weight measurement by FD/MS. It was found that m/e was 742 relative to the molecular weight 742. The yield was 1.74 g (22%).

Synthesis Example 7 (Synthesis of Compound (9))

In a three-neck flask, 5.00 g (12.1 mmol) of compound (144-a), 4.58 g (12.1 mmol) of compound (144-b), 20 of a 2M aqueous solution of sodium carbonate, 40 mL of 1,2-dimethoxyethane and 1.40 g (1.21 mmol) of Pd(PPh$_3$)$_4$ were placed. The resulting mixture was refluxed for 16 hours in a nitrogen atmosphere.

After completion of the reaction, 100 of methanol was added to the sample solution, and ultrasonic cleaning was conducted for 10 minutes. The precipitated sample was collected by filtration, and washed with methanol, water and hexane. After drying the sample, a mixed solvent of hexane and ethyl acetate (hexane:ethyl acetate=1:1) was added, and ultrasonic cleaning was conducted for 30 minutes, whereby white solids were obtained. The identification was conducted by the molecular weight measurement by FD/MS. It was found that m/e was 666 relative to the molecular weight 666. The yield was 6.05 g (75%).

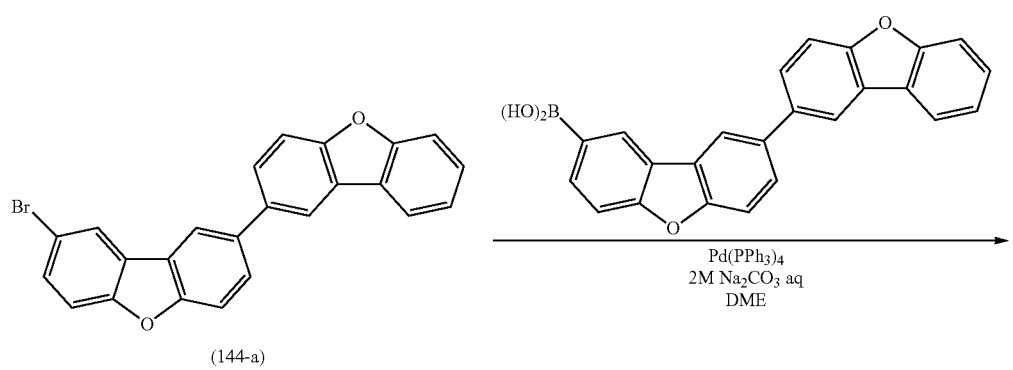

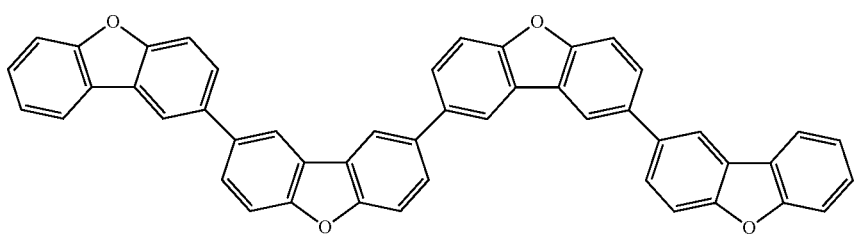

9

Synthesis Example 8 (Synthesis of Compound (140))

(1) Synthesis of Compound (140-a)

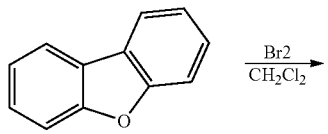

In a three-neck flask, 168.1 g (1000 mmol) of dibenzofuran and 1600 ml of dichloromethane were placed. The reactor was cooled to 0° C. in a nitrogen atmosphere. To the reactor, 125 mL of a dichloromethane solution of 255.8 g of bromine was added dropwise over 40 minutes, and the resultant was stirred at room temperature for 12 hours.

After completion of the reaction, the reactor was cooled to 0° C. 500 mL of water was added, and further, 100 ml of a 20% aqueous NaHSO$_4$ solution was added. The sample solution was transferred to a separating funnel, and extracted with dichloromethane several times. The resultant was washed with 300 ml of a 1N aqueous sodium hydroxide solution and dried with anhydrous magnesium sulfate, filtrated and concentrated. The resulting product was washed by dispersing in hexane, whereby white solids were obtained. The yield was 212 g (65%).

(2) Synthesis of Compound (140-b)

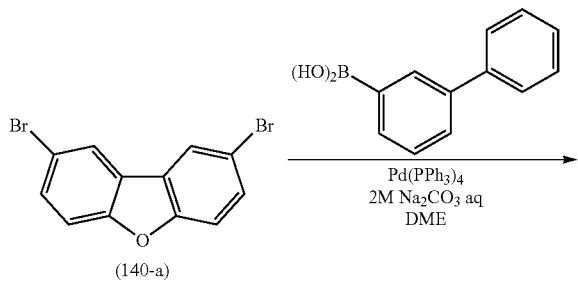

In a three-neck flask, 10.0 g (50.5 mmol) of compound (140-a), 14.8 g (45.5 mmol) of compound (140-b), 75 mL of a 2M aqueous sodium carbonate solution, 150 mL of 1,2-dimethoxyethane and 2.92 g (2.53 mmol) of Pd(PPh$_3$)$_4$ were placed. The resulting mixture was refluxed for 16 hours in a nitrogen atmosphere.

After completion of the reaction, the sample solution was transferred to a separating funnel, and extracted with ethyl acetate several times. The resultant was dried with anhydrous magnesium sulfate, filtrated and concentrated. The resulting product was purified by silica gel chromatography (hexane), whereby white solids were obtained. The yield was 12.0 g (60%).

(2) Synthesis of Compound (140-c)

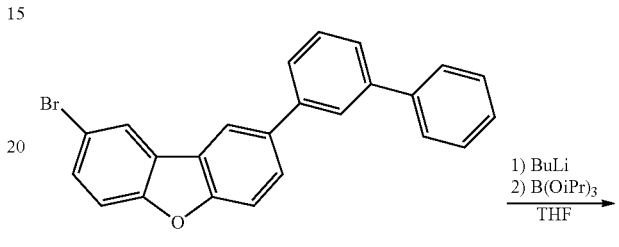

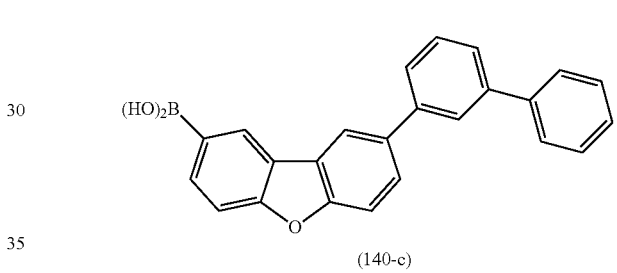

In a three-neck flask, 7.15 g (17.9 mmol) of compound (140-b) and 100 mL of dehydrated tetrahydrofuran were placed. In a nitrogen atmosphere, the reactor was cooled to −70° C. To the reactor, 12 mL (19.7 mmol) of a 1.67M n-butyllithium hexane solution was added dropwise, and the resultant was stirred at −70° C. for 1 hour. To the reactor, 12.4 mL (53.7 mmol) of triisopropyl borate was added, and the resultant was stirred at room temperature for 6 hours. After completion of the reaction, 50 mL of an aqueous 1N HCl solution was added, followed by stirring for 30 minutes. The sample solution was transferred to a separating funnel, and extracted with dichloromethane several times. The resultant was dried with anhydrous magnesium sulfate, filtrated and concentrated. The resulting product was washed by dispersing in hexane, whereby white solids were obtained. The yield was 3.80 g (53%).

(4) Synthesis of Compound (140-d)

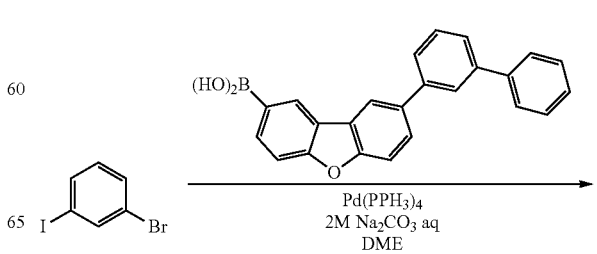

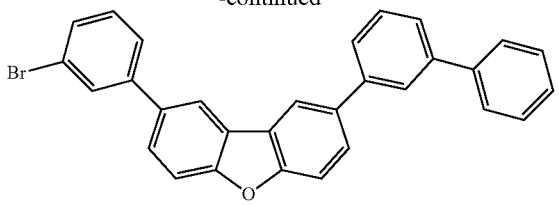

In a three-neck flask, 3.50 g (12.4 mmol) of 1-bromo-3-iodobenzene, 3.00 g (8.25 mmol) of compound (140-c), 13 mL of a 2M aqueous solution of sodium carbonate, 25 mL of 1,2-dimethoxyethane and 0.477 g (0.413 mmol) of Pd(PPh$_3$)$_4$ were placed. The resulting mixture was refluxed for 16 hours in a nitrogen atmosphere. After completion of the reaction, the sample solution was transferred to a separating funnel, and extracted with ethyl acetate several times. The resultant was dried with anhydrous magnesium sulfate, filtrated and concentrated. The resulting product was purified by silica gel chromatography (hexane), whereby white solids were obtained. The yield was 3.10 g (79%).

(5) Synthesis of Compound (140)

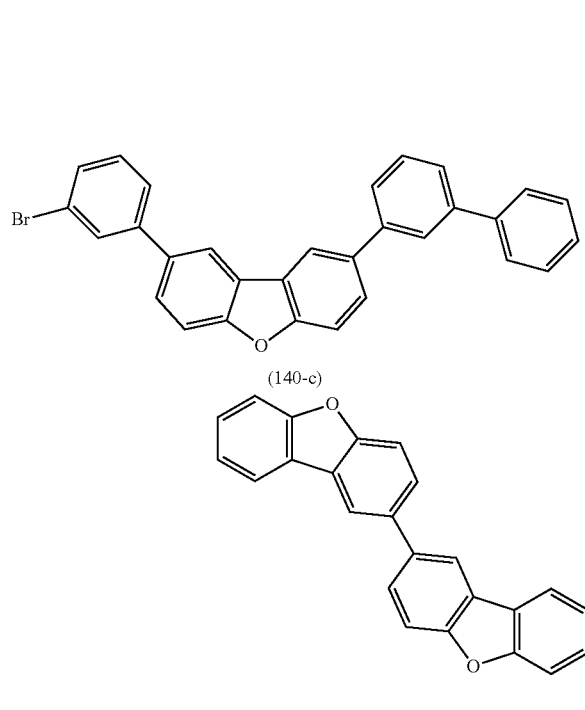

In a three-neck flask, 3.08 g (6.45 mmol) of compound (140-c), 3.67 g (9.70 mmol) of compound (144-b), 15 mL of a 2M aqueous solution of sodium carbonate, 30 mL of 1,2-dimethoxyethane and 0.560 g (0.485 mmol) of Pd(PPh$_3$)$_4$ were placed. The resulting mixture was refluxed for 16 hours in a nitrogen atmosphere.

After completion of the reaction, 100 mL of methanol was added to the sample solution and ultrasonic cleaning was conducted for 10 minutes. The precipitated sample was collected by filtration, and washed with methanol, water and hexane. After drying the sample, a mixed solvent of hexane and ethyl acetate (hexane:ethyl acetate=1:1) was again added to conduct ultrasonic cleaning for 30 minutes, whereby white solids were obtained. The identification was conducted by the molecular weight measurement by FD/MS. It was found that m/e was 728 relative to the molecular weight 728. The yield was 1.28 g (27%).

Synthesis Example 9 (Synthesis of Compound (145))

(1) Synthesis of Compound (145-a)

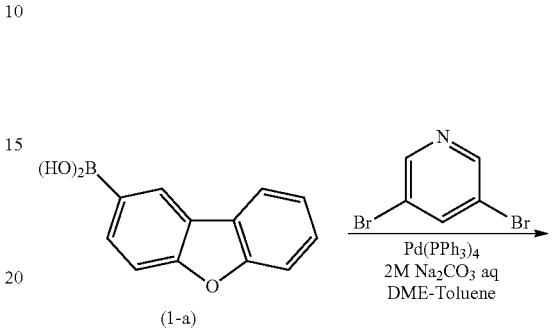

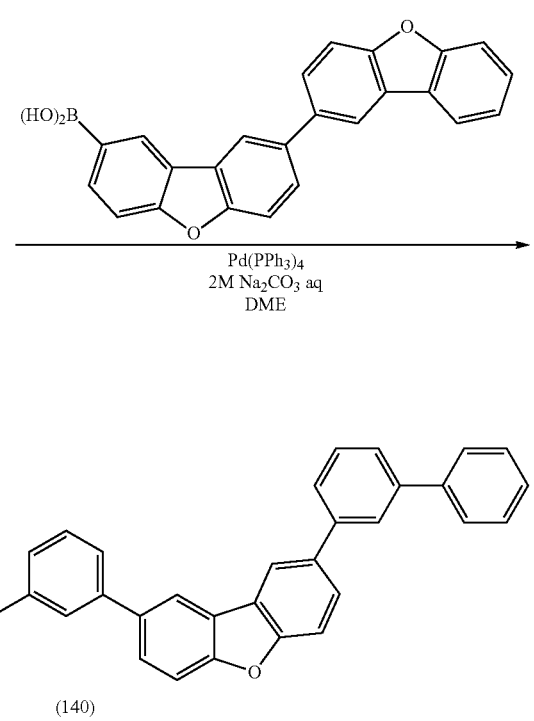

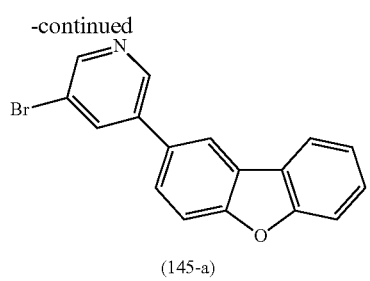

In a three-neck flask, 16.83 g (79.4 mmol) of compound (1-a), 18.81 g (79.4 mmol) of 3,5-dibromopyridine, 119 mL of a 2M aqueous solution of sodium carbonate, 119 mL of 1,2-dimethoxyethane, 119 mL of toluene and 2.75 g (2.38 mmol) of Pd(PPh$_3$)$_4$ were placed. The resulting mixture was refluxed for 8 hours in an argon atmosphere.

After completion of the reaction, the sample solution was transferred to a separating funnel, and extracted with ethyl acetate several times. The resultant was dried with anhydrous magnesium sulfate, filtrated and concentrated. The resulting product was purified by silica gel chromatography (hexane:dichloromethane=1:5), whereby white solids were obtained. The yield was 14.62 g (56%).

(2) Synthesis of Compound (145)

apparatus. First, compound (HI1) and then compound (HT1) were deposited by resistance heating on the surface on which the ITO electrode line has been formed so as to cover the ITO electrode line, whereby a 20 nm thick film and a 60 nm thick film were sequentially formed. The film forming rate was 1 Å/s. These films serve as a hole-injecting layer and an electron-transporting layer, respectively.

Subsequently, compound (1) and compound (BD1) were deposited on the hole-injecting/transporting layer by resistance heating at the same time to form a thin film having a thickness of 50 nm. The deposition was conducted such that the mass ratio of compound (BD1) becomes 20% relative to

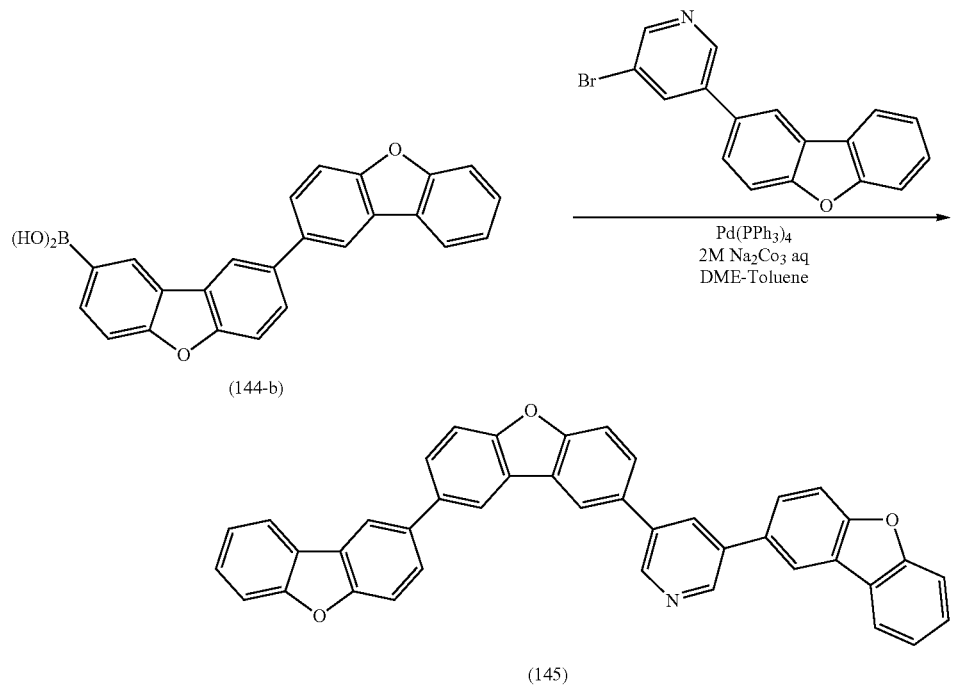

In a three-neck flask, 2.50 g (7.71 mmol) of compound (145-a), 2.92 g (7.71 mmol) of compound (144-b), 12 mL of a 2M aqueous solution of sodium carbonate, 12 mL of 1,2-dimethoxyethane, 12 mL of toluene and 267 mg (0.23 mmol) of Pd(PPh$_3$)$_4$ were placed. The resulting mixture was refluxed for 8 hours in an argon atmosphere.

After completion of the reaction, the sample solution was transferred to a separating funnel, and extracted with ethyl acetate several times. The resultant was dried with anhydrous magnesium sulfate, filtrated and concentrated. The resulting product was purified by silica gel chromatography (hexane:dichloromethane:ethyl acetate=2:20:1), whereby white solids were obtained. The identification was conducted by the molecular weight measurement by FD/MS. It was found that m/e was 577 relative to the molecular weight 577. The yield was 1.29 g (27%).

Example 1

A glass substrate with an ITO electrode line having a film thickness of 130 nm (manufactured by GEOMATIC Co., Ltd.) was subjected to ultrasonic cleaning in isopropyl alcohol for 5 minutes and then UV ozone cleaning for 30 minutes.

The cleaned glass substrate with an ITO electrode line was mounted on a substrate holder in a vacuum deposition the total amount of compound (1) and compound (BD1). The film forming rates for compound (1) and (BD1) were 1.2 Å/s and 0.3 Å/s, respectively. The thin film obtained serves as a phosphorescent emitting layer.

Next, on the phosphorescent emitting layer, compound (H1) was deposited by resistance heating to form a thin film having a thickness of 10 nm. The film forming rate was 1.2 Å/s. The thin film obtained serves as a barrier layer.

Then, on the barrier layer, compound (ET1) was deposited by resistance heating to form a thin film having a thickness of 10 nm. The film forming rate was 1 Å/s. The film obtained serves as an electron-injecting layer.

Next, LiF was deposited on the electron-injecting layer at the film forming rate of 0.1 Å/s to form a 1.0 nm-thick film.

Then, on the LiF film, metal aluminum was deposited at the film forming rate of 8.0 Å/s to form a metal cathode having a film thickness of 80 nm, whereby an organic EL device was obtained.

The organic EL device thus obtained was evaluated by the following method.

(1) External Quantum Efficiency (%)

At 23° C., in a dry nitrogen gas atmosphere, the external quantum efficiency at a luminance of 1000 cd/m$^2$ was measured by using a luminance meter (spectroradiometer CS-1000 manufactured by Konica Minolta, Inc.).

(2) Half Life (Hour(s))

A continuous current test (direct current) was conducted at an initial luminance of 1000 cd/m$^2$ to measure a time that elapses until the initial luminance was reduced by half.

(3) Voltage (V)

At 23° C., in a dry nitrogen gas atmosphere, a voltage was applied to a device in which electric wiring had been done by means of KEITHLY 236 SOURCE MEASURE UNIT, thereby to cause the device to emit light. Then, a voltage applied on the wiring resistance that is uninvolved in the device was deducted, thereby to determine a voltage applied to the device. At the same time of applying and measuring the voltage, the luminance was measured by using a luminance meter (spectroradiometer CS-1000 manufactured by Konica Minolta, Inc.). The voltage at a device luminance of 100 cd/m$^2$ was determined from these measurement results.

Examples 2 to 5, and Comparative Examples 1 and 2

Organic EL devices were fabricated in the same manner as in Example 1, except that, in Example 1, compounds shown in Table 1 were used instead of compound (1) to form an emitting layer. The organic EL devices obtained were evaluated in the same manner as in Example 1. The results are shown in Table 1.

TABLE 1

|  | Emitting layer | Voltage (V) | Half life (hrs) |
| --- | --- | --- | --- |
| Example 1 | Compound (1) | 4.5 | 3,000 |
| Example 2 | Compound (81) | 4.4 | 3,000 |
| Example 3 | Compound (129) | 3.9 | 2,200 |
| Example 4 | Compound (135) | 4.0 | 2,700 |
| Example 5 | Compound (140) | 4.1 | 3,300 |
| Com. Ex. 1 | Compound (H2) | 5.5 | 600 |
| Com. Ex. 2 | Compound (H3) | 4.5 | 2,000 |

Table 1 shows that the organic EL device obtained by using of the compound of the invention in an emitting layer can be driven at a lower voltage and have a longer life as compared with those obtained in Comparative Examples 1 and 2.

Examples 6 to 12 and Comparative Examples 3 and 4

Organic EL devices were fabricated in the same manner as in Example 1, except that, in Example 1, compound (H1) was used instead of compound (1) as a phosphorescent emitting layer material, and compounds shown in Table 2 were used instead of compound (H1) as a hole barrier layer material to form a hole barrier layer.

TABLE 2

|  | Hole barrier layer | Voltage (V) | Half life (hrs) |
| --- | --- | --- | --- |
| Example 6 | Compound (1) | 5.6 | 7,500 |
| Example 7 | Compound (17) | 4.1 | 5,500 |
| Example 8 | Compound (129) | 5.2 | 8,000 |
| Example 9 | Compound (135) | 4.1 | 5,300 |
| Example 10 | Compound (144) | 5.2 | 8,200 |
| Example 11 | Compound (9) | 5.2 | 5,700 |
| Example 12 | Compound (140) | 5.3 | 5,300 |
| Com. Ex. 3 | Compound (H2) | 5.6 | 3,500 |
| Com. Ex. 4 | Compound (H3) | 5.5 | 3,000 |

Table 2 shows that the organic EL device obtained by using the compound of the invention in a hole barrier layer can have a longer life as compared with those obtained in Comparative Examples 3 and 4.

The structural formulas of the compounds used in Examples and Comparative Examples are shown below.

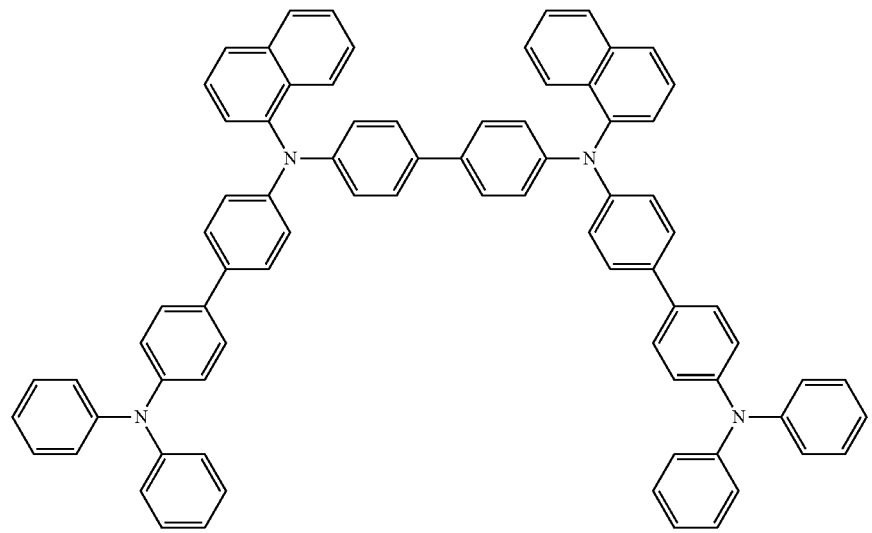

Compound (H1)

-continued
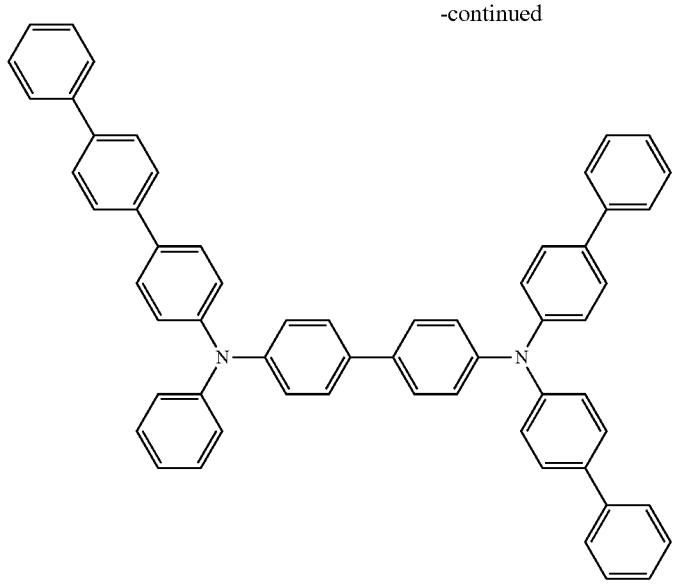
Compound (HT1)
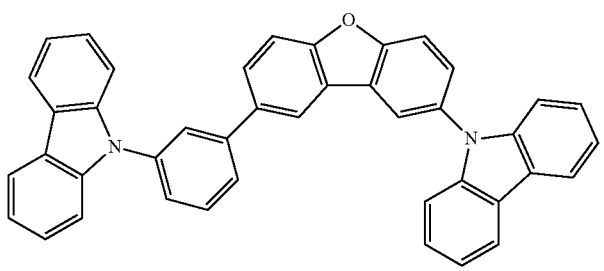
Compound (H1)
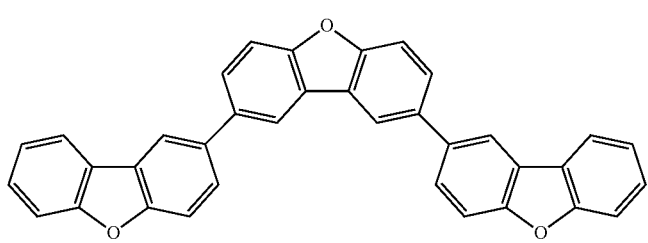
Compound (H2)
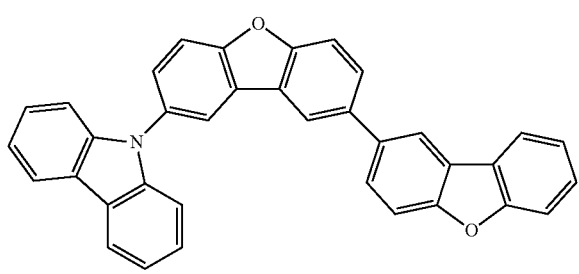
Compound (H3)
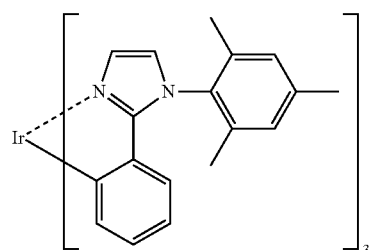
Compound (BD1)

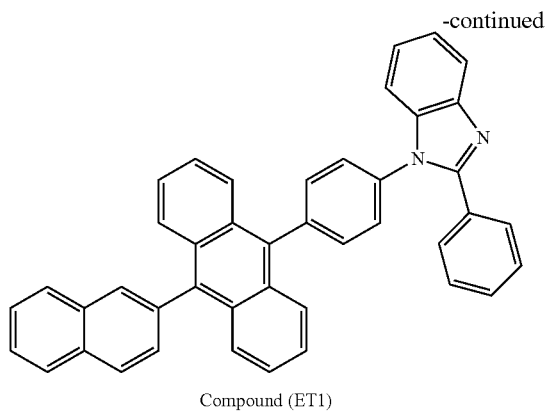

Compound (ET1)

Triplet energies of the materials for an organic EL device used in Examples and Comparative Examples are shown in Table 3. The triplet energy is defined as bellow. An intended material is dissolved in EPA solvent (diethyl ether:isopentane:ethanol=5:5:2 (volume ratio)) at a concentration of 10 μmol/L to prepare a sample for phosphorescence measurement. The sample for phosphorescence measurement is placed in a quartz cell. The sample in the quartz cell was irradiated with excited light at a temperature of 77 K, and the phosphorescence spectrum of the emitted phosphorescent was measured. The triplet energy is obtained by using the conversion equation of $E^T$ (eV)=1239.85/$\lambda_{edge}$ based on the measurement value.

TABLE 3

| Compound | Triplet energy (ev) |
| --- | --- |
| Compound (1) | 2.95 |
| Compound (17) | 3.02 |
| Compound (81) | 2.94 |
| Compound (129) | 3.02 |
| Compound (135) | 3.02 |
| Compound (144) | 3.02 |
| Compound (9) | 2.94 |
| Compound (140) | 2.96 |
| Compound (H1) | 3.03 |
| Compound (H2) | 3.02 |
| Compound (H3) | 2.95 |
| Compound (BD1) | 2.64 |

As shown in Table 3, in the organic EL device of the invention, the difference ($\Delta E^T$) between the triplet energy ($E^T_{TB}$) of compounds (1), (17), (81), (129), (135), (144), (9) or (140) as the material for an organic EL device of the invention and the triplet energy ($E^T_d$) of compound (BD1) as a phosphorescent dopant satisfies the relation of 0.2 eV<$\Delta E^T$=$E^T_{TB}$-$E^T_d$. Therefore, the use of a material for an organic device of the invention can provide a high efficient organic EL device.

INDUSTRIAL APPLICABILITY

The invention is useful as the organic EL device which can be driven at a low voltage, has a long life and has an excellent heat resistance, as well as the material for an organic EL device realizing the same.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in the specification of a Japanese application on the basis of which the present application claims Paris convention priority are incorporated herein by reference in its entirety.

The invention claimed is:

1. A compound represented by the following formula (1):

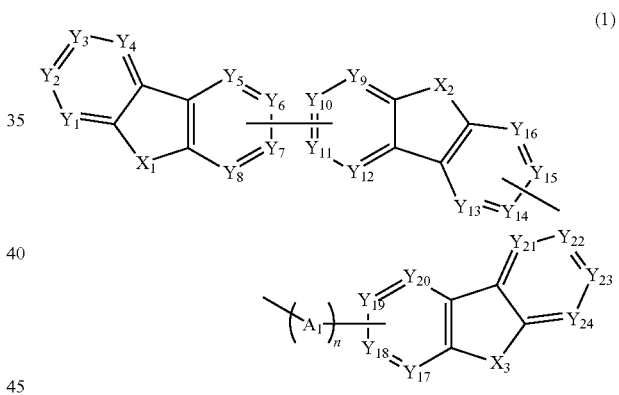

wherein in the formula (1), $X_1$ to $X_3$ are independently O or S;

$Y_1$ to $Y_4$ and $Y_{21}$ to $Y_{24}$ are independently C(Ra$_1$) or N;

of $Y_5$ to $Y_{12}$, one of $Y_5$ to $Y_8$ and one of $Y_9$ to $Y_{12}$ are carbon atoms which are bonded to each other, and the remaining $Y_5$ to $Y_{12}$ are independently C(Ra$_1$) or N;

one of $Y_{13}$ to $Y_{16}$ which bonds to $A_1$ is a carbon atom, and the remaining $Y_{13}$ to $Y_{16}$ are independently C(Ra$_1$) or N;

one of $Y_{17}$ to $Y_{20}$ which bonds to $A_1$ is a carbon atom, and the remaining $Y_{17}$ to $Y_{20}$ are independently C(Ra$_1$) or N, provided that one of (a) to (c) is met:

(a) at least one of $Y_1$ to $Y_4$ is N, (b) at least one of $Y_{21}$ to $Y_{24}$ is N, (c) at least one of $Y_1$ to $Y_4$ is N, and at least one of $Y_{21}$ to $Y_{24}$ is N;

$A_1$ is a substituted or unsubstituted arylene group including 6 to 30 ring carbon atoms, or a divalent group of a substituted or unsubstituted pyrrolyl group, a substituted or unsubstituted pyrazinyl group, a substituted or unsubstituted pyridinyl group, a substituted or unsubstituted pyrimidinyl group, a substituted or unsubstituted pyridazinyl group, a substituted or unsubstituted triazinyl group, a substituted or unsubstituted indolyl group, a substituted or unsubstituted isoindolyl group, a substituted or unsubstituted furyl group, a substituted or unsubstituted benzofuranyl group, a substituted or unsubstituted isobenzofuranyl group, a substituted or unsubstituted quinolyl group, a substituted or unsubstituted isoquinolyl group, a substituted or unsubstituted quinoxalinyl group, a substituted or unsubstituted phenanthridinyl group, a substituted or unsubstituted acridinyl group, a substituted or unsubstituted phenanthrolinyl group, a substituted or unsubstituted thienyl group, a substituted or unsubstituted pyrrolidinyl group, a substituted or unsubstituted dioxanyl group, a substituted or unsubstituted piperidinyl group, a substituted or unsubstituted morpholinyl group, a substituted or unsubstituted piperazinyl group, a substituted or unsubstituted thiophenyl group, a substituted or unsubstituted oxazolyl group, a substituted or unsubstituted oxadiazolyl group, a substituted or unsubstituted benzoxazolyl group, a substituted or unsubstituted thiazolyl group, a substituted or unsubstituted thiadiazolyl group, a substituted or unsubstituted benzothiazolyl group, a substituted or unsubstituted triazolyl group, an substituted or unsubstituted imidazolyl group, a substituted or unsubstituted benzimidazolyl group, a substituted or unsubstituted pyranyl group, or a substituted or unsubstituted benzo[c]dibenzofuranyl group;

group, a substituted or unsubstituted pyrrolidinyl group, a substituted or unsubstituted dioxanyl group, a substituted or unsubstituted piperidinyl group, a substituted or unsubstituted morpholinyl group, a substituted or unsubstituted piperazinyl group, a substituted or unsubstituted thiophenyl group, a substituted or unsubstituted oxazolyl group, a substituted or unsubstituted oxadiazolyl group, a substituted or unsubstituted benzoxazolyl group, a substituted or unsubstituted thiazolyl group, a substituted or unsubstituted thiadiazolyl group, a substituted or unsubstituted benzothiazolyl group, a substituted or unsubstituted triazolyl group, a substituted or unsubstituted imidazolyl group, a substituted or unsubstituted benzimidazolyl group, a substituted or unsubstituted pyranyl group, or a substituted or unsubstituted benzo[c]dibenzofuranyl group, when $Ra_1$ has a substituent the substituent is an alkyl group having 1 to 30 carbon atoms, an alkoxy group having 1 to 30 carbon atoms, a fluoroalkyl group having 1 to 30 carbon atoms, an aryl group having 6 to 30 ring atoms, an aryloxy group having 6 to 30 ring atoms, an aralkyl group having 7 to 30 carbon atoms, a silyl group, an alkylsilyl group having 1 to 6 carbon atoms, a fluoro group or a cyano group; and when $A_1$ has a substituent, the substituent is a heteroaryl group including 3 to 30 ring carbon atoms.

2. The compound according to claim 1, which is represented by the following formula (2):

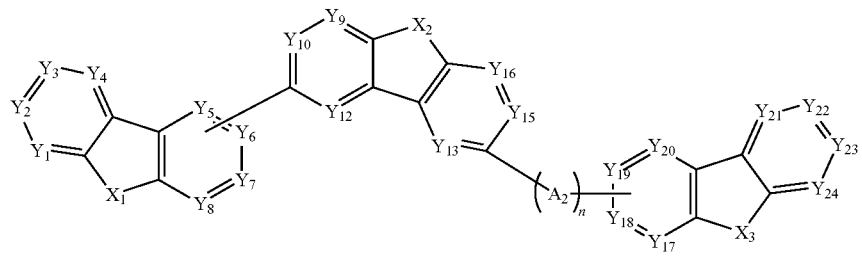

(2)

n is an integer of 1 to 4;

$Ra_1$ is a hydrogen atom, a substituted or unsubstituted aryl group including 6 to 30 ring carbon atoms, a substituted or unsubstituted a pyrrolyl group, a substituted or unsubstituted pyrazinyl group, a substituted or unsubstituted pyridinyl group, a substituted or unsubstituted pyrimidinyl group, a substituted or unsubstituted pyridazinyl group, a substituted or unsubstituted triazinyl group, a substituted or unsubstituted indolyl group, a substituted or unsubstituted isoindolyl group, a substituted or unsubstituted furyl group, a substituted or unsubstituted benzofuranyl group, a substituted or unsubstituted isobenzofuranyl group, a substituted or unsubstituted dibenzofuranyl group, a substituted or unsubstituted dibenzothiophenyl group, a substituted or unsubstituted quinolyl group, a substituted or unsubstituted isoquinolyl group, a substituted or unsubstituted quinoxalinyl group, a substituted or unsubstituted phenanthridinyl group, a substituted or unsubstituted acridinyl group, a substituted or unsubstituted phenanthrolinyl group, a substituted or unsubstituted thienyl wherein in the formula (2),
$X_1$ to $X_3$ are the same as $X_1$ to $X_3$ in the formula (1), respectively;
$Y_1$ to $Y_4$, $Y_9$, $Y_{10}$, $Y_{12}$, $Y_{13}$, $Y_{15}$, $Y_{16}$ and $Y_{21}$ to $Y_{24}$ are independently $C(Ra_2)$ or N;
one of $Y_5$ to $Y_8$ which bonds to the ring comprising $Y_9$, $Y_{10}$ and $Y_{12}$ is a carbon atom, and the remaining $Y_5$ to $Y_8$ are independently $C(Ra_2)$ or N;
one of $Y_{17}$ to $Y_{20}$ which bonds to $A_2$ is a carbon atom, and the remaining $Y_{17}$ to $Y_{20}$ are independently $C(Ra_2)$ or N;
provided that one of (a) to (c) is met:
(a) at least one of $Y_1$ to $Y_4$ is N,
(b) at least one of $Y_{21}$ to $Y_{24}$ is N,
(c) at least one of $Y_1$ to $Y_4$ is N, and at least one of $Y_{21}$ to $Y_{24}$ is N;
$A_2$ is the same as $A_1$ in the formula (1);
n is the same as n in the formula (1); and
$Ra_2$ is the same as $Ra_1$ in the formula (1).

3. The compound according to claim 2, which is represented by the following formula (3):

(3)

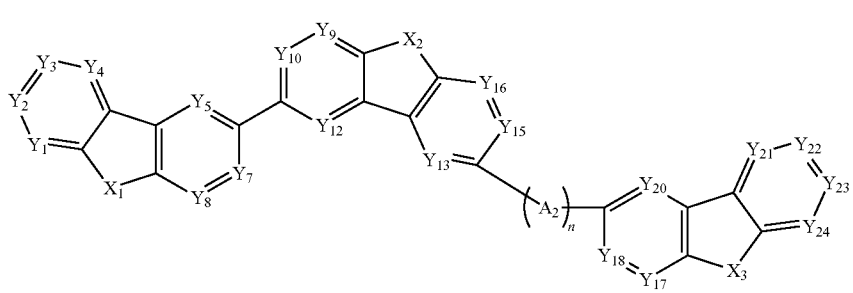

wherein in the formula (3),
$Y_1$ to $Y_5$, $Y_7$ to $Y_{10}$, $Y_{12}$, $Y_{13}$, $Y_{15}$, $Y_{16}$ to $Y_{18}$ and $Y_{20}$ to $Y_{24}$ are independently $C(Ra_2)$ or N;
provided that one of (a) to (c) is met:
(a) at least one of $Y_1$ to $Y_4$ is N,
(b) at least one of $Y_{21}$ to $Y_{24}$ is N,
(c) at least one of $Y_1$ to $Y_4$ is N, and at least one of $Y_{21}$ to $Y_{24}$ is N; and
$X_1$ to $X_3$, $A_2$, n, $Ra_z$ are the same as $X_1$ to $X_3$, $A_2$, n, $Ra_z$ in the formula (2), respectively.

4. The compound according to claim 3, which is represented by the following formula (4):

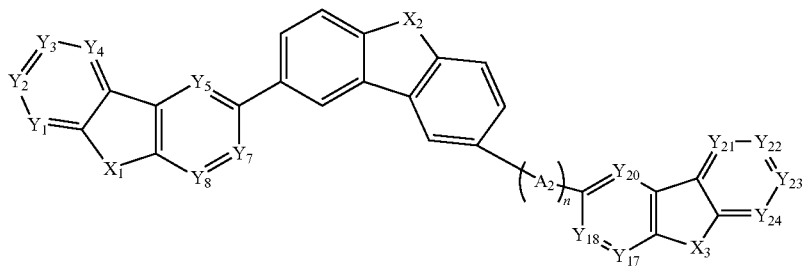

wherein in the formula (4),
$X_1$ to $X_3$, $Y_1$ to $Y_5$, $Y_7$, $Y_8$, $Y_{17}$, $Y_{18}$, $Y_{20}$ to $Y_{24}$, $A_2$ and n are the same as $X_1$ to $X_3$, $Y_1$ to $Y_5$, $Y_7$, $Y_8$, $Y_{17}$, $Y_{18}$, $Y_{20}$ to $Y_{24}$, $A_2$ and n in the formula (3), respectively.

5. The compound according to claim 4, which is represented by the following formula (5):

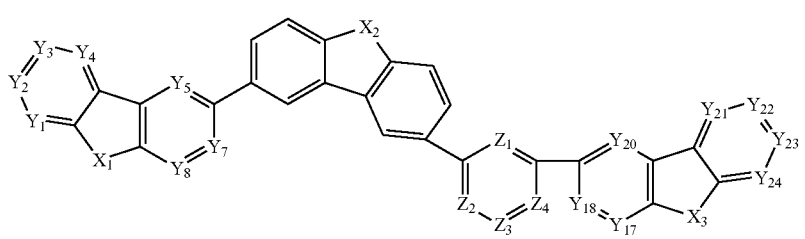

wherein in the formula (5),
$Z_1$ to $Z_4$ are independently $C(Ra_z)$ or N;
$X_1$ to $X_3$, $Y_1$ to $Y_5$, $Y_7$, $Y_8$, $Y_{17}$, $Y_{18}$, and $Y_{20}$ to $Y_{24}$ are the same as $X_1$ to $X_3$, $Y_1$ to $Y_5$, $Y_7$, $Y_8$, $Y_{17}$, $Y_{18}$, and $Y_{20}$ to $Y_{24}$ in the formula (4), respectively; and $Ra_z$ is the same as $Ra_z$ in the formula (2).

6. The compound according to claim 1, wherein $A_1$ is a substituted or unsubstituted arylene group including 6 to 30 ring carbon atoms.

7. The compound according to claim 1, wherein $A_1$ is a divalent group of a substituted or unsubstituted pyrrolyl group, a substituted or unsubstituted pyrazinyl group, a substituted or unsubstituted pyridinyl group, a substituted or unsubstituted pyrimidinyl group, a substituted or unsubstituted pyridazinyl group, a substituted or unsubstituted triazinyl group, a substituted or unsubstituted indolyl group, a substituted or unsubstituted isoindolyl group, a substituted or unsubstituted furyl group a substituted or unsubstituted benzofuranyl group, a substituted or unsubstituted isobenzofuranyl group, a substituted or unsubstituted quinolyl group, a substituted or unsubstituted isoquinolyl group, a substituted or unsubstituted quinoxalinyl group, a substituted or unsubstituted phenanthridinyl group, a substituted or unsubstituted acridinyl group a substituted or unsubstituted phenanthrolinyl group, a substituted or unsubstituted thienyl group, a substituted or unsubstituted pyrrolidinyl group, a substituted or unsubstituted dioxanyl group, a substituted or unsubstituted piperidinyl group, a substituted or unsubstituted morpholinyl group, a substituted or unsubstituted piperazinyl group, a substituted or unsubstituted thiophenyl group, a substituted or unsubstituted oxazolyl group, a substituted or unsubstituted oxadiazolyl group, a substituted or unsubstituted benzoxazolyl group, a substituted or unsubstituted thiazolyl group, a substituted or unsubstituted thiadiazolyl group, a substituted or unsubstituted benzothiazolyl group, a substituted or unsubstituted triazolyl group, an substituted or unsubstituted imidazolyl group, a substituted or unsubstituted benzimidazolyl group, a substituted or unsubstituted pyranyl group, or a substituted or unsubstituted benzo[c]dibenzofuranyl group.

8. The compound according to claim 2, wherein $A_2$ is a substituted or unsubstituted arylene group including 6 to 30 ring carbon atoms.

9. The compound according to claim 2, wherein $A_2$ is a divalent group of a substituted or unsubstituted pyrrolyl group, a substituted or unsubstituted pyrazinyl group, a substituted or unsubstituted pyridinyl group, a substituted or unsubstituted pyrimidinyl group, a substituted or unsubstituted pyridazinyl group, a substituted or unsubstituted triazinyl group, a substituted or unsubstituted indolyl group, a substituted or unsubstituted isoindolyl group, a substituted or unsubstituted furyl group, a substituted or unsubstituted benzofuranyl group, a substituted or unsubstituted isobenzofuranyl group, a substituted or unsubstituted quinolyl group, a substituted or unsubstituted isoquinolyl group, a substituted or unsubstituted quinoxalinyl group, a substituted or unsubstituted phenanthridinyl group, a substituted or unsubstituted acridinyl group, a substituted or unsubstituted phenanthrolinyl group, a substituted or unsubstituted thienyl group, a substituted or unsubstituted pyrrolidinyl group, a substituted or unsubstituted dioxanyl group, a substituted or unsubstituted piperidinyl group, a substituted or unsubstituted morpholinyl group, a substituted or unsubstituted piperazinyl group, a substituted or unsubstituted thiophenyl group, a substituted or unsubstituted oxazolyl group, a substituted or unsubstituted oxadiazolyl group, a substituted or unsubstituted benzoxazolyl group, a substituted or unsubstituted thiazolyl group, a substituted or unsubstituted thiadiazolyl group, a substituted or unsubstituted benzothiazolyl group, a substituted or unsubstituted triazolyl group, an substituted or unsubstituted imidazolyl group, a substituted or unsubstituted benzimidazolyl group, a substituted or unsubstituted pyranyl group, or a substituted or unsubstituted benzo[c]dibenzofuranyl group.

10. The compound according to claim 1, wherein $A_1$ is a substituted or unsubstituted arylene group including 6 to 30 ring carbon atoms and the substituent is a heteroaryl group having 3 to 30 ring carbon atoms.

11. The compound according to claim 1, wherein at least one of $Y_1$ to $Y_4$ and $Y_{21}$ to $Y_{24}$ is N.

12. The compound according to claim 1, wherein at least one of $Y_1$ to $Y_4$ is N.

13. The compound according to claim 1, wherein at least one of $Y_{21}$ to $Y_{24}$ is N.

14. The compound according to claim 1, wherein at least one of $Y_1$ to $Y_4$ is N, and at least one of $Y_{21}$ to $Y_{24}$ is N.

15. A material for an organic electroluminescence device comprising the compound according to claim 1.

16. An organic electroluminescence device comprising one or more organic thin film layers including an emitting layer between a cathode and an anode, wherein at least one of the organic thin film layers comprises the material for an organic electroluminescence device according to claim 15.

17. The organic electroluminescence device according to claim 16, wherein the emitting layer comprises the material for an organic electroluminescence device.

18. The organic electroluminescence device according to claim 17, wherein the emitting layer comprises the material for an organic electroluminescence device as a host material for the emitting layer.

19. The organic electroluminescence device according to claim 16, wherein an electro-transporting region is provided between the emitting layer and the cathode, and the electro-transporting region comprises the material for an organic electroluminescence device.

20. The organic electroluminescence device according to claim 16, wherein the emitting layer comprises a phosphorescent material.

21. The organic electroluminescence device according to claim 20, wherein the phosphorescent material is a compound containing a metal selected from iridium (Ir), osmium (Os) and platinum (Pt).

22. The organic electroluminescence device according to claim 21, wherein the compound containing a metal is an ortho-metalized complex.

23. The organic electroluminescence device according to claim 16, wherein an electron-injecting layer is provided between the emitting layer and the cathode, and the electro-injecting layer comprises a nitrogen-containing heterocyclic derivative.

24. A compound represented by the following formula (11):

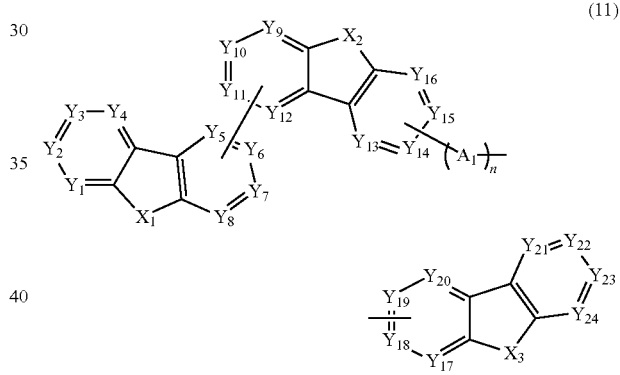

wherein in the formula (11),
$X_1$ to $X_3$ are O;
$Y_1$ to $Y_4$ and $Y_{21}$ to $Y_{24}$ are independently $C(Ra_1)$ or N;
of $Y_5$ to $Y_{12}$, one of $Y_5$ to $Y_8$ and one of $Y_9$ to $Y_{12}$ are carbon atoms which are bonded to each other, and the remaining $Y_5$ to $Y_{12}$ are independently $C(Ra_1)$ or N;
one of $Y_{13}$ to $Y_{16}$ which bonds to $A_1$ is a carbon atom, and the remaining $Y_{13}$ to $Y_{16}$ are independently $C(Ra_1)$ or N;
one of $Y_{17}$ to $Y_{20}$ which bonds to $A_1$ is a carbon atom, and the remaining $Y_{17}$ to $Y_{20}$ are independently $C(Ra_1)$ or N;
$A_1$ is a substituted or unsubstituted phenylene group, an unsubstituted dibenzofuran group or an unsubstituted aza-dibenzofuran group;
n is an integer of 1 to 4;
$Ra_1$ is a hydrogen atom, an unsubstituted phenyl group, an unsubstituted biphenyl group, or an unsubstituted dibenzofuran group; and
when $A_1$ has a substituent, the substituent is a heteroaryl group including 3 to 30 ring carbon atoms.

25. The compound according to claim 24, which is represented by the following formula (12):

(12)

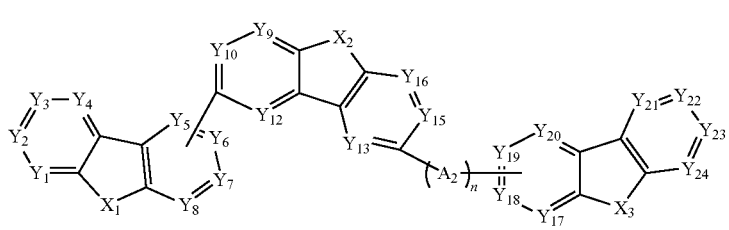

wherein in the formula (12),
$X_1$ to $X_3$ are the same as $X_1$ to $X_3$ in the formula (11), respectively;
$Y_1$ to $Y_4$, $Y_9$, $Y_{10}$, $Y_{12}$, $Y_{13}$, $Y_{15}$, $Y_{16}$ and $Y_{21}$ to $Y_{24}$ are independently $C(Ra_2)$ or N;
one of $Y_5$ to $Y_8$ which bonds to the ring comprising $Y_9$, $Y_{10}$ and $Y_{12}$ is a carbon atom, and the remaining $Y_5$ to $Y_8$ are independently $C(Ra_2)$ or N;
one of $Y_{17}$ to $Y_{20}$ which bonds to $A_2$ is a carbon atom, and the remaining $Y_{17}$ to $Y_{20}$ are independently $C(Ra_2)$ or N;
$A_2$ is the same as $A_1$ in the formula (11);
n is the same as n in the formula (11); and
$Ra_z$ is the same as $Ra_1$ in the formula (11).

26. The compound according to claim 25, which is represented by the following formula (13):

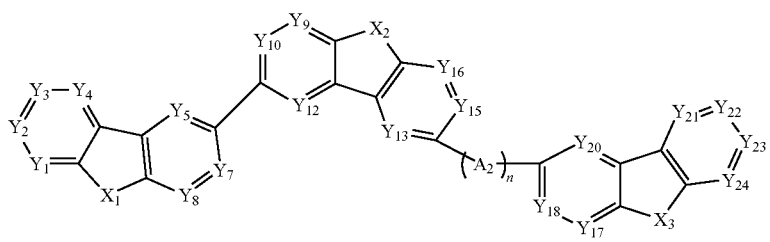

wherein in the formula (13),
$Y_1$ to $Y_5$, $Y_7$ to $Y_{10}$, $Y_{12}$, $Y_{13}$, $Y_{15}$, $Y_{16}$ to $Y_{18}$ and $Y_{20}$ to $Y_{24}$ are independently $C(Ra_2)$ or N; and
$X_1$ to $X_3$, $A_2$, n, $Ra_z$ are the same as $X_1$ to $X_3$, $A_2$, n, $Ra_z$ in the formula (12), respectively.

27. The compound according to claim 26, which is represented by the following formula (14):

28. The compound according to claim 24, wherein at least one of $Y_1$ to $Y_4$ and $Y_{21}$ to $Y_{24}$ is N.
29. The compound according to claim 24, wherein at least one of $Y_1$ to $Y_4$ is N.
30. The compound according to claim 24, wherein at least one of $Y_{21}$ to $Y_{24}$ is N.
31. The compound according to claim 24, wherein at least one of $Y_1$ to $Y_4$ is N, and at least one of $Y_{21}$ to $Y_{24}$ is N.
32. The compound according to claim 24, wherein $Y_1$ to $Y_4$ and each of $Y_5$ to $Y_8$ that is not the carbon atom which is bonded to one of one of $Y_9$ to $Y_{12}$ are independently $C(Ra_1)$.
33. A material for an organic electroluminescence device comprising the compound according to claim 24.
34. An organic electroluminescence device comprising one or more organic thin film layers including an emitting layer between a cathode and an anode, wherein at least one of the organic thin film layers comprises the material for an organic electroluminescence device according to claim 33.
35. The organic electroluminescence device according to claim 34, wherein the emitting layer comprises the material for an organic electroluminescence device.

(14)

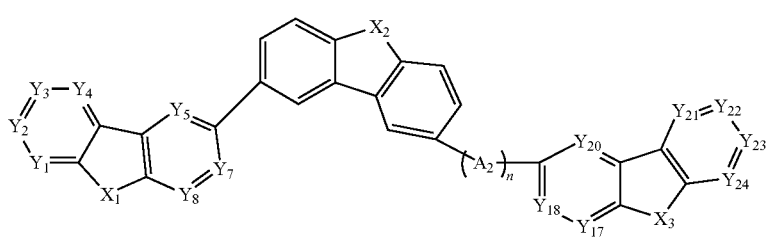

wherein in the formula (14),
$X_1$ to $X_3$, $Y_1$ to $Y_5$, $Y_7$, $Y_8$, $Y_{17}$, $Y_{18}$, $Y_{20}$ to $Y_{24}$, $A_2$ and n are the same as $X_1$ to $X_3$, $Y_1$ to $Y_5$, $Y_7$, $Y_8$, $Y_{17}$, $Y_{18}$, $Y_{20}$ to $Y_{24}$, $A_2$ and n in the formula (13), respectively.

36. The organic electroluminescence device according to claim 35, wherein the emitting layer comprises the material for an organic electroluminescence device as a host material for the emitting layer.

37. The organic electroluminescence device according to claim 34, wherein an electro-transporting region is provided between the emitting layer and the cathode, and the electro-transporting region comprises the material for an organic electroluminescence device.

38. The organic electroluminescence device according to claim 34, wherein the emitting layer comprises a phosphorescent material.

39. The organic electroluminescence device according to claim 38, wherein the phosphorescent material is a compound containing a metal selected from iridium (Ir), osmium (Os) and platinum (Pt).

40. The organic electroluminescence device according to claim 39, wherein the compound containing a metal is an ortho-metalized complex.

41. The organic electroluminescence device according to claim 34, wherein an electron-injecting layer is provided between the emitting layer and the cathode, and the electro-injecting layer comprises a nitrogen-containing heterocyclic derivative.

* * * * *